US012577310B2

(12) United States Patent
Morsey et al.

(10) Patent No.: US 12,577,310 B2
(45) Date of Patent: Mar. 17, 2026

(54) **CANINIZED ANTIBODIES TO CANINE INTERLEUKIN-31 RECEPTOR *ALPHA***

(71) Applicant: Intervet Inc., Rahway, NJ (US)

(72) Inventors: Mohamad Morsey, Omaha, NE (US); Yuanzheng Zhang, Somerset, NJ (US); Anasuya Saha, Fremont, CA (US)

(73) Assignee: INTERVET INC., Rahway, NJ (US)

( * ) Notice: Subject to any disclaimer, the term of this patent is extended or adjusted under 35 U.S.C. 154(b) by 532 days.

(21) Appl. No.: 18/247,653

(22) PCT Filed: Oct. 14, 2021

(86) PCT No.: PCT/EP2021/078386
§ 371 (c)(1),
(2) Date: Apr. 3, 2023

(87) PCT Pub. No.: WO2022/079139
PCT Pub. Date: Apr. 21, 2022

(65) Prior Publication Data
US 2023/0391879 A1 Dec. 7, 2023

Related U.S. Application Data

(60) Provisional application No. 63/235,258, filed on Aug. 20, 2021, provisional application No. 63/235,257, filed on Aug. 20, 2021, provisional application No. 63/127,184, filed on Dec. 18, 2020, provisional application No. 63/092,296, filed on Oct. 15, 2020, provisional application No. 63/092,294, filed on Oct. 15, 2020.

(51) Int. Cl.
*C07K 16/28* (2006.01)
*A61P 17/04* (2006.01)
*C12N 15/63* (2006.01)

(52) U.S. Cl.
CPC .......... *C07K 16/2866* (2013.01); *A61P 17/04* (2018.01); *C12N 15/63* (2013.01); *C07K 2317/20* (2013.01); *C07K 2317/24* (2013.01); *C07K 2317/53* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 2013/0022616 A1 | 1/2013 | Bammert et al. | |
| 2020/0239563 A1 | 7/2020 | Piketty | |

FOREIGN PATENT DOCUMENTS

| | | | |
|---|---|---|---|
| CN | 110563844 A | † | 12/2019 |
| JP | 2014529295 A | | 11/2014 |
| JP | 2021509103 A | | 3/2021 |
| JP | 2023545182 A | | 10/2023 |
| RU | 2016129113 A | | 1/2018 |
| WO | WO 2020157636 A1 | | 8/2020 |

OTHER PUBLICATIONS

Grimstad et al. Anti-interleukin-31-antibodies ameliorate scratching behaviour in NC/Nga mice: a model of atopic dermatitis. Experimental Dermatology, 18, 35-43, 2008. (Year: 2008).*
Li et al. Preparation of anti canine interleukin 31 receptor alpha polyclonal antibody and evaluation of its therapeutic effect in canine atopic dermatitis. Animal Diseases (2023) 3:26. (Year: 2023).*
Siniewicz-Luzenczyk et al. Correlation between serum interleukin-31 level and the severity of disease in children with atopic dermatitis. Postepy Dermatol Alergol . Oct. 2013;30(5):282-5. (Year: 2013).*
Badri et al., 2016, "Optimization of radiation dosing schedules for proneural glioblastoma," J. Math. Biol., 72(5):1301-1336 (Epub 2015).
Baylot et al., 2017, "Chapter 13—TCTP Has a Crucial Role in the Different Stages of Prostate Cancer Malignant Progression," Results Probl. Cell Differ., 64:255-261.
Mariuzza et al., 1987, "The structural basis of antigen-antibody recognition," Annu. Rev. Biophys. Biophys. Chem., 16:139-159.
Roitt et al., 2000, "Humanized antibodies to amyloid beta", in Immunology, Moscow, Mir, pp. 110-111, in Russian with English translation (9 pages).
Singer et al., 1998, "Genes and Genomes," Moscow, Mir, translation from English, 1:63-64, in Russian with machine English translation (8 pages).
Venereau et al., 2010, "Definition and characterization of an inhibitor for interleukin-31," J. Biol. Chem., 285(20):14955-14963.
Zhang et al., 2008, "Structures and biological functions of IL-31 and IL-31 receptors," Cytokine Growth Factor Rev., 19(5-6):347-356.
Kabashima et al., 2020, "Trial of Nemolizumab and Topical Agents for Atopic Dermatitis with Pruritus," N. Engl. J. Med., 383(2):141-150 and Supplementary Appendix (37 pages).
Ruzicka et al., 2017, "Anti-Interleukin-31 Receptor A Antibody for Atopic Dermatitis," N. Engl. J. Med., 376(9):826-835 and Supplementary Appendix (32 pages).
Venereau et al., "Definition and Characterization of an Inhibitor for Interleukin-31," Journal of Biological Chemistry, vol. 285, No. 20, May 14, 2010, pp. 14955-14963.†
Zhang et al., "Structures and biological functions of IL-31 and IL-31 receptors," Cytokine Growth Factor Rev., vol. 19, Issue 5-6, 2008, pp. 347-356.†

* cited by examiner
† cited by third party

*Primary Examiner* — Maher M Haddad
(74) *Attorney, Agent, or Firm* — JONES DAY

(57) ABSTRACT

The present invention provides caninized rat antibodies to canine IL-31 receptor alpha that have a high binding affinity for canine IL-31 receptor alpha, and that can block the binding of canine IL-31 to canine IL-31 receptor alpha. The present invention further provides the use of the antibodies for the treatment of atopic dermatitis in dogs.

19 Claims, 10 Drawing Sheets

Specification includes a Sequence Listing.

IL31Ra/IL31 ELISA

Binding of xIL31R mAbs to IL31RA

Blocking of IL-31 binding by anti-IL-31RA antibodies

Induction of STAT-3 phosphorylation by IL-31

| | Baf3 | Baf3-OI |
|---|---|---|
| EC50 | ~ 0.000 | 29.16 |

Inhibition of cIL-31 mediated STAT-3 phosphorylation in Ba/F3-OI cells by the selected xIL-31R1a antibodies

Binding of caninized xIL-31R mAbs to cIL31-RA

Binding of caninized xIL-31R mAbs to cIL31-RA

Binding of caninized xIL-31R mAbs to cIL31-RA

Inhibition of cIL-31 mediated STAT-3 phosphorylation
by caninized xIL-31RA mAbs to cIL-31RA

SEQUENCE LISTING

<160> NUMBER OF SEQ ID NOS: 105

<210> SEQ ID NO 1
<211> LENGTH: 1521
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="Canine with HisTag"

<400> SEQUENCE: 1
gtgctgcccg ccaagcccga gaacatcagc tgcatcttct actacgagga gaacttcacc        60
tgcacctgga gccccgagaa ggaggccagc tacacctggt acaaggtgaa gagaacctac       120
agctacggct acaagagcga catctgcagc accgacaaca gcaccagagg caaccacgcc       180
agctgcagct tcctgccccc caccatcacc aaccccgaca actacaccat ccaggtggag       240
gcccagaacg ccgacggcat catgaagagc gacatcacct actggaacct ggacgccatc       300
atgaagatcg agcccccga gatcttcagc gtgaagagcg tgctgggcat caagagaatg       360
ctgcagatca agtggatcag acccgtgctg gcccccaca gcagcaccct gaagtacacc       420
ctgagattca gaaccatcaa cagcgcctac tggatggagg tgaacttcac caaggaggac       480
atcgacagag acgagaccta caacctgacc gagctgcagg ccttcaccga gtacgtgatg       540
accctgagat gcgcccccgc cgagagcatg ttctggagcg gctggagcca ggagaaggtg       600
ggcaccaccg aggaggaggc cccctacggc ctggacctgt ggagagtgct gaagcccgcc       660
atggtggacg gcagaagacc cgtgcagctg atgtggaaga aggccaccgg cgcccccgtg       720
ctggagaagg ccctgggcta caacatctgg tacttccccg agaacaacac caacctgacc       780
gagaccgtga acaccaccaa ccagacccac gagctgtacc tgggcggcaa gacctactgg       840
gtgtacgtgg tgagctacaa cagcctgggc gagagccccg tggccaccct gagaatcccc       900
gccctgaacg agaagaccct tccagtgcatc gaggccatgc aggcctgcct gacccaggac       960
cagctggtgg tggagtggca gagcagcgcc cccgaggtgg acacctggat ggtggagtgg      1020
ttccccgacg tggacagcga gcccagcagc ttcagctggg agagcgtgag ccaggccaga      1080
aactggacca tccagaagga cgagctgaag cccctgtggt gctacaacat cagcgtgtac      1140
cccgtgctga gagacagagt gggccagccc tacagcaccc aggcctacgt gcaggagggc      1200
atccccagcg ccggcccgt gacccaggcc gacagcatcg gcgtgaagac cgtgaccatc      1260
acctggaagg agatccccaa gagcaagaga aacggcttca tcaagaacta caccatcttc      1320
taccaggccg aggacggcaa ggagttcagc aagaccgtga acagcaacat cctgcagtac      1380
agactggaga gcctgaccag aagaaccagc tacagcctgc aggtgatggc cagcaccaac      1440
gccggcggca ccaacggcac caagatcaac ttcaagaccc tgagcatcag ccaccaccac      1500
caccaccacc accaccacca c                                                1521

<210> SEQ ID NO 2
<211> LENGTH: 507
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:

-continued

<221> NAME/KEY: source
<223> OTHER INFORMATION: /note="Canine with His Tag"

<400> SEQUENCE: 2

```
Val Leu Pro Ala Lys Pro Glu Asn Ile Ser Cys Ile Phe Tyr Tyr Glu
1               5                   10                  15

Glu Asn Phe Thr Cys Thr Trp Ser Pro Glu Lys Glu Ala Ser Tyr Thr
            20                  25                  30

Trp Tyr Lys Val Lys Arg Thr Tyr Ser Tyr Gly Tyr Lys Ser Asp Ile
        35                  40                  45

Cys Ser Thr Asp Asn Ser Thr Arg Gly Asn His Ala Ser Cys Ser Phe
    50                  55                  60

Leu Pro Pro Thr Ile Thr Asn Pro Asp Asn Tyr Thr Ile Gln Val Glu
65                  70                  75                  80

Ala Gln Asn Ala Asp Gly Ile Met Lys Ser Asp Ile Thr Tyr Trp Asn
                85                  90                  95

Leu Asp Ala Ile Met Lys Ile Glu Pro Pro Glu Ile Phe Ser Val Lys
            100                 105                 110

Ser Val Leu Gly Ile Lys Arg Met Leu Gln Ile Lys Trp Ile Arg Pro
        115                 120                 125

Val Leu Ala Pro His Ser Ser Thr Leu Lys Tyr Thr Leu Arg Phe Arg
    130                 135                 140

Thr Ile Asn Ser Ala Tyr Trp Met Glu Val Asn Phe Thr Lys Glu Asp
145                 150                 155                 160

Ile Asp Arg Asp Glu Thr Tyr Asn Leu Thr Glu Leu Gln Ala Phe Thr
                165                 170                 175

Glu Tyr Val Met Thr Leu Arg Cys Ala Pro Ala Glu Ser Met Phe Trp
            180                 185                 190

Ser Gly Trp Ser Gln Glu Lys Val Gly Thr Thr Glu Glu Glu Ala Pro
        195                 200                 205

Tyr Gly Leu Asp Leu Trp Arg Val Leu Lys Pro Ala Met Val Asp Gly
    210                 215                 220

Arg Arg Pro Val Gln Leu Met Trp Lys Lys Ala Thr Gly Ala Pro Val
225                 230                 235                 240

Leu Glu Lys Ala Leu Gly Tyr Asn Ile Trp Tyr Phe Pro Glu Asn Asn
                245                 250                 255

Thr Asn Leu Thr Glu Thr Val Asn Thr Thr Asn Gln Thr His Glu Leu
            260                 265                 270

Tyr Leu Gly Gly Lys Thr Tyr Trp Val Tyr Val Val Ser Tyr Asn Ser
        275                 280                 285

Leu Gly Glu Ser Pro Val Ala Thr Leu Arg Ile Pro Ala Leu Asn Glu
    290                 295                 300

Lys Thr Phe Gln Cys Ile Glu Ala Met Gln Ala Cys Leu Thr Gln Asp
305                 310                 315                 320

Gln Leu Val Val Glu Trp Gln Ser Ser Ala Pro Glu Val Asp Thr Trp
                325                 330                 335

Met Val Glu Trp Phe Pro Asp Val Asp Ser Glu Pro Ser Ser Phe Ser
            340                 345                 350

Trp Glu Ser Val Ser Gln Ala Arg Asn Trp Thr Ile Gln Lys Asp Glu
        355                 360                 365

Leu Lys Pro Leu Trp Cys Tyr Asn Ile Ser Val Tyr Pro Val Leu Arg
    370                 375                 380

Asp Arg Val Gly Gln Pro Tyr Ser Thr Gln Ala Tyr Val Gln Glu Gly
385                 390                 395                 400
```

-continued

```
Ile Pro Ser Ala Gly Pro Val Thr Gln Ala Asp Ser Ile Gly Val Lys
            405                 410                 415

Thr Val Thr Ile Thr Trp Lys Glu Ile Pro Lys Ser Lys Arg Asn Gly
            420                 425                 430

Phe Ile Lys Asn Tyr Thr Ile Phe Tyr Gln Ala Glu Asp Gly Lys Glu
            435                 440                 445

Phe Ser Lys Thr Val Asn Ser Asn Ile Leu Gln Tyr Arg Leu Glu Ser
        450                 455                 460

Leu Thr Arg Arg Thr Ser Tyr Ser Leu Gln Val Met Ala Ser Thr Asn
465                 470                 475                 480

Ala Gly Gly Thr Asn Gly Thr Lys Ile Asn Phe Lys Thr Leu Ser Ile
            485                 490                 495

Ser His His His His His His His His His
            500                 505
```

```
<210> SEQ ID NO 3
<211> LENGTH: 5
<212> TYPE: PRT
<213> ORGANISM: Rattus norvegicus

<400> SEQUENCE: 3

Asn Tyr Trp Met Thr
1                 5
```

```
<210> SEQ ID NO 4
<211> LENGTH: 17
<212> TYPE: PRT
<213> ORGANISM: Rattus norvegicus

<400> SEQUENCE: 4

Ser Ile Thr Asn Thr Gly Gly Ser Thr Tyr Tyr Pro Asp Ser Val Lys
1                 5                 10                  15

Gly
```

```
<210> SEQ ID NO 5
<211> LENGTH: 12
<212> TYPE: PRT
<213> ORGANISM: Rattus norvegicus

<400> SEQUENCE: 5

Gly Pro Thr Thr Val Val Gly Gly Trp Phe Ala Tyr
1                 5                 10
```

```
<210> SEQ ID NO 6
<211> LENGTH: 11
<212> TYPE: PRT
<213> ORGANISM: Rattus norvegicus

<400> SEQUENCE: 6

Lys Ala Ser Gln Asn Val Gly Ser Asn Val Asp
1                 5                 10
```

```
<210> SEQ ID NO 7
<211> LENGTH: 7
<212> TYPE: PRT
<213> ORGANISM: Rattus norvegicus

<400> SEQUENCE: 7

Arg Pro Ser Asn Arg Tyr Thr
1                 5
```

```
<210> SEQ ID NO 8
<211> LENGTH: 9
<212> TYPE: PRT
<213> ORGANISM: Rattus norvegicus

<400> SEQUENCE: 8

Met Gln Ser Asn Ser Tyr Pro Pro Thr
1               5

<210> SEQ ID NO 9
<211> LENGTH: 7
<212> TYPE: PRT
<213> ORGANISM: Rattus norvegicus

<400> SEQUENCE: 9

Arg Ala Ser Ser Arg Ser Thr
1               5

<210> SEQ ID NO 10
<211> LENGTH: 17
<212> TYPE: PRT
<213> ORGANISM: Rattus norvegicus

<400> SEQUENCE: 10

Ser Ile Thr Asn Thr Gly Gly Ser Thr Phe Tyr Pro Asp Ser Val Lys
1               5                   10                  15

Gly

<210> SEQ ID NO 11
<211> LENGTH: 13
<212> TYPE: PRT
<213> ORGANISM: Rattus norvegicus

<400> SEQUENCE: 11

Gly Pro Asp Tyr Gly Gly His Leu Asn Trp Phe Ala Tyr
1               5                   10

<210> SEQ ID NO 12
<211> LENGTH: 7
<212> TYPE: PRT
<213> ORGANISM: Rattus norvegicus

<400> SEQUENCE: 12

Lys Ala Ser Asn Arg Tyr Thr
1               5

<210> SEQ ID NO 13
<211> LENGTH: 5
<212> TYPE: PRT
<213> ORGANISM: Rattus norvegicus

<400> SEQUENCE: 13

Ser Asn Gly Val Ser
1               5

<210> SEQ ID NO 14
<211> LENGTH: 16
<212> TYPE: PRT
<213> ORGANISM: Rattus norvegicus

<400> SEQUENCE: 14

Ala Ile Ser Ser Gly Gly Ser Thr Tyr Tyr Asn Ser Val Leu Lys Ser
1               5                   10                  15
```

```
<210> SEQ ID NO 15
<211> LENGTH: 12
<212> TYPE: PRT
<213> ORGANISM: Rattus norvegicus

<400> SEQUENCE: 15

Arg Leu Ser Gly Tyr Asn Tyr Val Pro Phe Ala Tyr
1               5                   10

<210> SEQ ID NO 16
<211> LENGTH: 11
<212> TYPE: PRT
<213> ORGANISM: Rattus norvegicus

<400> SEQUENCE: 16

Lys Ala Ser Gln Asn Ile Tyr Lys His Leu Ala
1               5                   10

<210> SEQ ID NO 17
<211> LENGTH: 7
<212> TYPE: PRT
<213> ORGANISM: Rattus norvegicus

<400> SEQUENCE: 17

Asn Ala Asn Ser Leu Gln Thr
1               5

<210> SEQ ID NO 18
<211> LENGTH: 8
<212> TYPE: PRT
<213> ORGANISM: Rattus norvegicus

<400> SEQUENCE: 18

Gln Gln Tyr Tyr Ser Gly Asp Thr
1               5

<210> SEQ ID NO 19
<211> LENGTH: 5
<212> TYPE: PRT
<213> ORGANISM: Rattus norvegicus

<400> SEQUENCE: 19

Ser Thr Phe Met His
1               5

<210> SEQ ID NO 20
<211> LENGTH: 17
<212> TYPE: PRT
<213> ORGANISM: Rattus norvegicus

<400> SEQUENCE: 20

Arg Ile Asp Pro Val Asn Gly Asn Thr Ile Tyr Ser Glu Lys Phe Lys
1               5                   10                  15

Ser

<210> SEQ ID NO 21
<211> LENGTH: 10
<212> TYPE: PRT
<213> ORGANISM: Rattus norvegicus

<400> SEQUENCE: 21

Phe Asn Tyr Ala Gly His Ser Gly Asp Tyr
1               5                   10
```

-continued

```
<210> SEQ ID NO 22
<211> LENGTH: 11
<212> TYPE: PRT
<213> ORGANISM: Rattus norvegicus

<400> SEQUENCE: 22

Arg Ala Ser Gln Asp Val Gly Ile Tyr Val Asn
1               5                   10

<210> SEQ ID NO 23
<211> LENGTH: 7
<212> TYPE: PRT
<213> ORGANISM: Rattus norvegicus

<400> SEQUENCE: 23

Arg Ala Thr Asn Leu Ala Asp
1               5

<210> SEQ ID NO 24
<211> LENGTH: 9
<212> TYPE: PRT
<213> ORGANISM: Rattus norvegicus

<400> SEQUENCE: 24

Leu Gln Tyr Asp Glu Tyr Pro Tyr Thr
1               5

<210> SEQ ID NO 25
<211> LENGTH: 5
<212> TYPE: PRT
<213> ORGANISM: Rattus norvegicus

<400> SEQUENCE: 25

Asp Tyr Tyr Met Ala
1               5

<210> SEQ ID NO 26
<211> LENGTH: 17
<212> TYPE: PRT
<213> ORGANISM: Rattus norvegicus

<400> SEQUENCE: 26

Thr Ile Ser Tyr Asp Gly Ser Ser Thr Tyr Tyr Arg Asp Ser Val Arg
1               5                   10                  15

Gly

<210> SEQ ID NO 27
<211> LENGTH: 13
<212> TYPE: PRT
<213> ORGANISM: Rattus norvegicus

<400> SEQUENCE: 27

Gly Pro Leu Thr Asp Trp Ala Pro Asn Trp Phe Ala Tyr
1               5                   10

<210> SEQ ID NO 28
<211> LENGTH: 11
<212> TYPE: PRT
<213> ORGANISM: Rattus norvegicus

<400> SEQUENCE: 28

Gln Thr Ser Glu Asp Ile Tyr Ser Gly Leu Ala
1               5                   10
```

<210> SEQ ID NO 29
<211> LENGTH: 7
<212> TYPE: PRT
<213> ORGANISM: Rattus norvegicus

<400> SEQUENCE: 29

Gly Ala Ser Arg Leu Glu Asp
1               5

<210> SEQ ID NO 30
<211> LENGTH: 9
<212> TYPE: PRT
<213> ORGANISM: Rattus norvegicus

<400> SEQUENCE: 30

Gln Gln Gly Leu Lys Tyr Pro Asn Thr
1               5

<210> SEQ ID NO 31
<211> LENGTH: 5
<212> TYPE: PRT
<213> ORGANISM: Rattus norvegicus

<400> SEQUENCE: 31

Asn Tyr Tyr Met Ala
1               5

<210> SEQ ID NO 32
<211> LENGTH: 17
<212> TYPE: PRT
<213> ORGANISM: Rattus norvegicus

<400> SEQUENCE: 32

Ser Ile Ser Thr Gly Gly Gly Asn Thr Tyr Tyr Arg Asp Ser Val Lys
1               5                   10                  15

Gly

<210> SEQ ID NO 33
<211> LENGTH: 8
<212> TYPE: PRT
<213> ORGANISM: Rattus norvegicus

<400> SEQUENCE: 33

His Gly Thr Leu Tyr Phe Asp Tyr
1               5

<210> SEQ ID NO 34
<211> LENGTH: 13
<212> TYPE: PRT
<213> ORGANISM: Rattus norvegicus

<400> SEQUENCE: 34

Glu Arg Ser Ser Gly Asp Ile Gly Asp Ser Tyr Val Ser
1               5                   10

<210> SEQ ID NO 35
<211> LENGTH: 7
<212> TYPE: PRT
<213> ORGANISM: Rattus norvegicus

<400> SEQUENCE: 35

Ala Asp Asp Gln Arg Pro Ser
1               5

<210> SEQ ID NO 36
<211> LENGTH: 11
<212> TYPE: PRT
<213> ORGANISM: Rattus norvegicus

<400> SEQUENCE: 36

Gln Ser Tyr Asp Ser Asn Ile Asp Gly Pro Val
1               5                   10

<210> SEQ ID NO 37
<211> LENGTH: 7
<212> TYPE: PRT
<213> ORGANISM: Rattus norvegicus

<400> SEQUENCE: 37

Val Asp Asp Gln Arg Pro Ser
1               5

<210> SEQ ID NO 38
<211> LENGTH: 13
<212> TYPE: PRT
<213> ORGANISM: Rattus norvegicus

<400> SEQUENCE: 38

Glu Arg Ser Ser Gly Asp Ile Gly Asn Thr Tyr Val Ser
1               5                   10

<210> SEQ ID NO 39
<211> LENGTH: 9
<212> TYPE: PRT
<213> ORGANISM: Rattus norvegicus

<400> SEQUENCE: 39

His Gly Thr Ile Ala Ala Met Asp Tyr
1               5

<210> SEQ ID NO 40
<211> LENGTH: 13
<212> TYPE: PRT
<213> ORGANISM: Rattus norvegicus

<400> SEQUENCE: 40

Glu Arg Asn Asn Gly Asp Ile Gly Asp Ser Tyr Val Ser
1               5                   10

<210> SEQ ID NO 41
<211> LENGTH: 17
<212> TYPE: PRT
<213> ORGANISM: Rattus norvegicus

<400> SEQUENCE: 41

Ser Ile Ser Thr Gly Gly Gly Asn Thr Phe Tyr Arg Asp Ser Val Lys
1               5                   10                  15

Gly

<210> SEQ ID NO 42
<211> LENGTH: 13
<212> TYPE: PRT
<213> ORGANISM: Rattus norvegicus

<400> SEQUENCE: 42

Glu Arg Thr Ser Gly Asp Ile Gly Asp Asn Tyr Val Ser
1               5                   10

```
<210> SEQ ID NO 43
<211> LENGTH: 8
<212> TYPE: PRT
<213> ORGANISM: Rattus norvegicus

<400> SEQUENCE: 43

His Thr Met Gly Tyr Phe Asp Tyr
1               5

<210> SEQ ID NO 44
<211> LENGTH: 13
<212> TYPE: PRT
<213> ORGANISM: Rattus norvegicus

<400> SEQUENCE: 44

Glu Arg Ser Ser Gly Asp Ile Gly Asp Asn Tyr Val Ser
1               5                   10

<210> SEQ ID NO 45
<211> LENGTH: 11
<212> TYPE: PRT
<213> ORGANISM: Rattus norvegicus

<400> SEQUENCE: 45

Gln Ser Tyr Asp Gly Lys Ile Glu Ile Pro Val
1               5                   10

<210> SEQ ID NO 46
<211> LENGTH: 13
<212> TYPE: PRT
<213> ORGANISM: Rattus norvegicus

<400> SEQUENCE: 46

Gly Pro Asp Tyr Gly Gly His Leu Asn Trp Phe Val Tyr
1               5                   10

<210> SEQ ID NO 47
<211> LENGTH: 5
<212> TYPE: PRT
<213> ORGANISM: Rattus norvegicus

<400> SEQUENCE: 47

Lys Tyr Trp Met Thr
1               5

<210> SEQ ID NO 48
<211> LENGTH: 17
<212> TYPE: PRT
<213> ORGANISM: Rattus norvegicus

<400> SEQUENCE: 48

Ser Ile Thr Asn Thr Gly Gly Ser Ser Tyr Tyr Ser Asp Ser Val Lys
1               5                   10                  15

Gly

<210> SEQ ID NO 49
<211> LENGTH: 117
<212> TYPE: PRT
<213> ORGANISM: Rattus norvegicus

<400> SEQUENCE: 49

Glu Val Gln Leu Val Glu Ser Gly Gly Gly Leu Val Gln Pro Gly Arg
1               5                   10                  15
```

-continued

---

Ser Met Lys Leu Ser Cys Ala Ala Ser Gly Phe Thr Phe Ser Asn Tyr
            20                  25                  30

Tyr Met Ala Trp Val Arg Gln Ala Pro Thr Lys Gly Leu Glu Trp Val
        35                  40                  45

Ala Ser Ile Ser Thr Gly Gly Gly Asn Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Thr Leu Tyr Phe Asp Tyr Trp Gly Gln Gly Val Met
            100                 105                 110

Val Thr Val Ser Ser
        115

<210> SEQ ID NO 50
<211> LENGTH: 112
<212> TYPE: PRT
<213> ORGANISM: Rattus norvegicus

<400> SEQUENCE: 50

Gln Phe Thr Leu Thr Gln Pro Lys Ser Val Ser Gly Ser Leu Arg Ser
1               5                   10                  15

Thr Ile Thr Ile Pro Cys Glu Arg Ser Ser Gly Asp Ile Gly Asp Ser
            20                  25                  30

Tyr Val Ser Trp Tyr Gln Gln His Leu Gly Arg Pro Pro Ile Asn Val
        35                  40                  45

Ile Tyr Ala Asp Asp Gln Arg Pro Ser Glu Val Ser Asp Arg Phe Ser
    50                  55                  60

Gly Ser Ile Asp Ser Ser Ser Asn Ser Ala Ser Leu Thr Ile Thr Asn
65                  70                  75                  80

Leu Gln Met Asp Asp Glu Ala Asp Tyr Phe Cys Gln Ser Tyr Asp Ser
                85                  90                  95

Asn Ile Asp Gly Pro Val Phe Gly Gly Gly Thr Lys Leu Thr Val Leu
            100                 105                 110

<210> SEQ ID NO 51
<211> LENGTH: 117
<212> TYPE: PRT
<213> ORGANISM: Rattus norvegicus

<400> SEQUENCE: 51

Glu Val Gln Leu Val Glu Ser Gly Gly Gly Leu Val Lys Pro Gly Arg
1               5                   10                  15

Ser Met Lys Leu Ser Cys Ala Ala Ser Gly Phe Thr Phe Ser Asn Tyr
            20                  25                  30

Tyr Met Ala Trp Val Arg Gln Ala Pro Thr Lys Gly Leu Glu Trp Val
        35                  40                  45

Ala Ser Ile Ser Thr Gly Gly Gly Asn Thr Tyr Tyr Arg Asp Ser Val
    50                  55                  60

Lys Gly Arg Phe Thr Ile Ser Arg Asp Asn Ala Lys Arg Thr Leu Tyr
65                  70                  75                  80

Leu Gln Met Asp Ser Leu Arg Ser Glu Asp Thr Ala Thr Tyr Tyr Cys
                85                  90                  95

Gly Arg His Gly Thr Leu Tyr Phe Asp Tyr Trp Gly Gln Gly Val Met
            100                 105                 110

-continued

```
Val Thr Val Ser Ser
        115

<210> SEQ ID NO 52
<211> LENGTH: 112
<212> TYPE: PRT
<213> ORGANISM: Rattus norvegicus

<400> SEQUENCE: 52

Gln Phe Thr Leu Thr Gln Pro Lys Ser Val Ser Gly Ser Leu Arg Ser
1               5                   10                  15

Thr Ile Thr Ile Pro Cys Glu Arg Ser Ser Gly Asp Ile Gly Asp Ser
            20                  25                  30

Tyr Val Ser Trp Tyr Gln Gln His Leu Gly Arg Pro Pro Ile Asn Val
        35                  40                  45

Ile Tyr Val Asp Asp Gln Arg Pro Ser Glu Val Ser Asp Arg Phe Ser
    50                  55                  60

Gly Ser Ile Asp Ser Ser Ser Asn Ser Ala Ser Leu Thr Ile Thr Asp
65                  70                  75                  80

Leu Gln Met Asp Asp Glu Ala Asp Tyr Phe Cys Gln Ser Tyr Asp Ser
                85                  90                  95

Asn Ile Asp Gly Pro Val Phe Gly Gly Gly Thr Lys Leu Thr Val Leu
            100                 105                 110

<210> SEQ ID NO 53
<211> LENGTH: 116
<212> TYPE: PRT
<213> ORGANISM: Rattus norvegicus

<400> SEQUENCE: 53

Glu Val Gln Leu Val Glu Ser Gly Gly Gly Leu Val Gln Pro Gly Arg
1               5                   10                  15

Ser Met Lys Leu Ser Cys Val Ala Ser Gly Phe Thr Phe Ser Asn Tyr
            20                  25                  30

Tyr Met Ala Trp Val Arg Gln Ala Pro Thr Lys Gly Leu Glu Trp Val
        35                  40                  45

Ala Ser Ile Ser Thr Gly Gly Gly Asn Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Thr Leu Tyr Phe Asp Tyr Trp Gly Gln Gly Val Met
            100                 105                 110

Val Thr Val Ser
        115

<210> SEQ ID NO 54
<211> LENGTH: 112
<212> TYPE: PRT
<213> ORGANISM: Rattus norvegicus

<400> SEQUENCE: 54

Gln Phe Thr Leu Thr Gln Pro Lys Ser Val Ser Gly Ser Leu Arg Ser
1               5                   10                  15

Thr Ile Thr Ile Pro Cys Glu Arg Ser Ser Gly Asp Ile Gly Asn Thr
            20                  25                  30

Tyr Val Ser Trp Tyr Gln Gln His Leu Gly Arg Pro Pro Ile Asn Val
```

-continued

```
            35                  40                  45

Ile Tyr Ala Asp Asp Gln Arg Pro Ser Glu Val Ser Asp Arg Phe Ser
    50                  55                  60

Gly Ser Ile Asp Ser Ser Ser Asn Ser Ala Ser Leu Thr Ile Thr Asn
65                  70                  75                  80

Leu Gln Met Asp Asp Glu Ala Asp Tyr Phe Cys Gln Ser Tyr Asp Ser
                85                  90                  95

Asn Ile Asp Gly Pro Val Phe Gly Gly Gly Thr Lys Leu Thr Val Leu
            100                 105                 110

<210> SEQ ID NO 55
<211> LENGTH: 118
<212> TYPE: PRT
<213> ORGANISM: Rattus norvegicus

<400> SEQUENCE: 55

Glu Val Gln Leu Val Glu Ser Gly Gly Gly Leu Val Gln Pro Gly Arg
1               5                   10                  15

Ser Met Lys Leu Ser Cys Ala Ala Leu Gly Phe Thr Phe Ser Asn Tyr
                20                  25                  30

Tyr Met Ala Trp Val Arg Gln Ala Pro Thr Lys Gly Leu Glu Trp Val
            35                  40                  45

Ala Ser Ile Ser Thr Gly Gly Gly Asn Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Thr Ile Ala Ala Met Asp Tyr Trp Gly Gln Gly Val
            100                 105                 110

Met Val Thr Val Ser Ser
        115

<210> SEQ ID NO 56
<211> LENGTH: 112
<212> TYPE: PRT
<213> ORGANISM: Rattus norvegicus

<400> SEQUENCE: 56

Gln Phe Thr Leu Thr Gln Pro Lys Ser Val Ser Gly Ser Leu Arg Ser
1               5                   10                  15

Thr Ile Thr Ile Pro Cys Glu Arg Asn Asn Gly Asp Ile Gly Asp Ser
                20                  25                  30

Tyr Val Ser Trp Tyr Gln Gln His Leu Gly Arg Pro Pro Ile Ile Val
            35                  40                  45

Ile Tyr Ala Asp Asp Gln Arg Pro Ser Glu Val Ser Asp Arg Phe Ser
    50                  55                  60

Gly Ser Ile Asp Ser Ser Ser Asn Ser Ala Ser Leu Thr Ile Thr Asn
65                  70                  75                  80

Leu Gln Met Asp Asp Glu Ala Asp Tyr Phe Cys Gln Ser Tyr Asp Ser
                85                  90                  95

Asn Ile Asp Gly Pro Val Phe Gly Gly Gly Thr Lys Leu Thr Val Leu
            100                 105                 110

<210> SEQ ID NO 57
<211> LENGTH: 118
<212> TYPE: PRT
```

<213> ORGANISM: Rattus norvegicus

<400> SEQUENCE: 57

```
Glu Val Gln Leu Val Glu Ser Gly Gly Gly Leu Val Gln Pro Gly Arg
1               5                   10                  15

Ser Met Lys Leu Ser Cys Ala Ala Phe Gly Phe Thr Phe Asn Asn Tyr
            20                  25                  30

Tyr Met Ala Trp Val Arg Gln Ala Pro Thr Lys Gly Leu Glu Trp Val
        35                  40                  45

Ala Ser Ile Ser Thr Gly Gly Gly Asn Thr Phe Tyr Arg Asp Ser Val
    50                  55                  60

Lys Gly Arg Phe Thr Ile Ser Arg Asp Asn Val Lys Ser Ile Leu Ser
65                  70                  75                  80

Leu Gln Met Asp Ser Leu Arg Ser Glu Asp Thr Ala Thr Tyr Tyr Cys
                85                  90                  95

Ala Arg His Gly Thr Ile Ala Ala Met Asp Tyr Trp Gly Gln Gly Val
            100                 105                 110

Met Val Thr Val Ser Ser
        115
```

<210> SEQ ID NO 58
<211> LENGTH: 112
<212> TYPE: PRT
<213> ORGANISM: Rattus norvegicus

<400> SEQUENCE: 58

```
Gln Phe Thr Leu Thr Gln Pro Lys Ser Val Ser Gly Ser Leu Arg Ser
1               5                   10                  15

Thr Ile Thr Ile Pro Cys Glu Arg Thr Ser Gly Asp Ile Gly Asp Asn
            20                  25                  30

Tyr Val Ser Trp Tyr Gln Gln His Leu Gly Arg Pro Pro Ile Asn Val
        35                  40                  45

Ile Tyr Ala Asp Asp Gln Arg Pro Ser Glu Val Ser Asp Arg Phe Ser
    50                  55                  60

Gly Ser Ile Asp Ser Ser Ser Asn Ser Ala Ser Leu Thr Ile Thr Asn
65                  70                  75                  80

Leu Gln Met Asp Asp Glu Ala Asp Tyr Phe Cys Gln Ser Tyr Asp Ser
                85                  90                  95

Asn Ile Asp Gly Pro Val Phe Gly Gly Gly Thr Lys Leu Thr Val Leu
            100                 105                 110
```

<210> SEQ ID NO 59
<211> LENGTH: 117
<212> TYPE: PRT
<213> ORGANISM: Rattus norvegicus

<400> SEQUENCE: 59

```
Glu Val Gln Leu Val Glu Ser Gly Gly Gly Leu Val Gln Pro Gly Arg
1               5                   10                  15

Ser Met Lys Leu Ser Cys Thr Ala Ser Gly Phe Thr Phe Ser Asn Tyr
            20                  25                  30

Tyr Met Ala Trp Val Arg Gln Ala Pro Thr Lys Gly Leu Glu Trp Val
        35                  40                  45

Ala Ser Ile Ser Thr Gly Gly Gly Asn Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80
```

-continued

```
Leu Gln Met Asp Ser Leu Arg Ala Glu Asp Thr Ala Thr Tyr Tyr Cys
                85                  90                  95

Ala Arg His Thr Met Gly Tyr Phe Asp Tyr Trp Gly Gln Gly Val Met
            100                 105                 110

Val Thr Val Ser Ser
        115

<210> SEQ ID NO 60
<211> LENGTH: 112
<212> TYPE: PRT
<213> ORGANISM: Rattus norvegicus

<400> SEQUENCE: 60

Gln Phe Thr Leu Thr Gln Pro Lys Ser Val Ser Gly Ser Leu Arg Ser
1               5                   10                  15

Thr Ile Thr Ile Pro Cys Glu Arg Ser Ser Gly Asp Ile Gly Asp Asn
            20                  25                  30

Tyr Val Ser Trp Tyr Gln Gln His Leu Gly Arg Pro Pro Ile Asn Val
        35                  40                  45

Ile Tyr Ala Asp Asp Gln Arg Pro Ser Glu Val Ser Asp Arg Phe Ser
    50                  55                  60

Gly Ser Ile Asp Ser Ser Ser Asn Ser Ala Ser Leu Thr Ile Thr Asn
65                  70                  75                  80

Leu Gln Met Asp Asp Glu Ala Asp Tyr Phe Cys Gln Ser Tyr Asp Gly
                85                  90                  95

Lys Ile Glu Ile Pro Val Phe Gly Gly Gly Thr Lys Leu Thr Val Leu
            100                 105                 110

<210> SEQ ID NO 61
<211> LENGTH: 120
<212> TYPE: PRT
<213> ORGANISM: Rattus norvegicus

<400> SEQUENCE: 61

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Asn
            20                  25                  30

Gly Val Ser Trp Val Arg Gln Pro Pro Gly Lys Gly Leu Glu Trp Ile
        35                  40                  45

Ala Ala Ile Ser Ser Gly Gly Ser Thr Tyr Tyr Asn Ser Val Leu Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Ile Tyr Phe Cys Thr
                85                  90                  95

Arg Arg Leu Ser Gly Tyr Asn Tyr Val Pro Phe Ala Tyr Trp Gly Gln
            100                 105                 110

Gly Thr Leu Val Thr Val Ser Ser
        115                 120

<210> SEQ ID NO 62
<211> LENGTH: 106
<212> TYPE: PRT
<213> ORGANISM: Rattus norvegicus

<400> SEQUENCE: 62
```

Asp Ile Gln Met Thr Gln Ser Pro Ser Leu Leu Ser Ala Ser Val Gly
1               5                   10                  15

Asp Arg Val Thr Leu Asn Cys Lys Ala Ser Gln Asn Ile Tyr Lys His
            20                  25                  30

Leu Ala Trp Cys Gln Gln Lys Leu Gly Glu Pro Pro Asn Leu Leu Ile
        35                  40                  45

Ser Asn Ala Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln Tyr Tyr Ser Gly Asp Thr
                85                  90                  95

Phe Gly Ala Gly Thr Lys Leu Glu Leu Lys
            100                 105

<210> SEQ ID NO 63
<211> LENGTH: 119
<212> TYPE: PRT
<213> ORGANISM: Rattus norvegicus

<400> SEQUENCE: 63

Glu Val Gln Leu Gln Gln Tyr Gly Ala Glu Leu Gly Lys Pro Gly Thr
1               5                   10                  15

Ser Val Lys Leu Ser Cys Lys Val Ser Gly Tyr Asn Ile Arg Ser Thr
            20                  25                  30

Phe Met His Trp Val Asn Gln Arg Pro Gly Lys Gly Leu Glu Trp Ile
        35                  40                  45

Gly Arg Ile Asp Pro Val Asn Gly Asn Thr Ile Tyr Ser Glu Lys Phe
    50                  55                  60

Lys Ser Lys Ala Thr Leu Thr Ala Asp Thr Ser Ser Asn Thr Ala Tyr
65                  70                  75                  80

Met Gln Leu Ser Gln Leu Lys Ser Asp Asp Thr Ala Ile Tyr Phe Cys
                85                  90                  95

Ala Met Phe Asn Tyr Ala Gly His Ser Gly Asp Tyr Trp Gly Gln Gly
            100                 105                 110

Val Met Val Thr Val Ser Ser
        115

<210> SEQ ID NO 64
<211> LENGTH: 107
<212> TYPE: PRT
<213> ORGANISM: Rattus norvegicus

<400> SEQUENCE: 64

Asp Ile Gln Met Thr Gln Ser Pro Ser Ser Met Ser Val Ser Leu Gly
1               5                   10                  15

Asp Thr Val Thr Ile Thr Cys Arg Ala Ser Gln Asp Val Gly Ile Tyr
            20                  25                  30

Val Asn Trp Phe Gln Gln Lys Pro Gly Lys Ser Pro Arg Arg Met Ile
        35                  40                  45

Tyr Arg Ala Thr Asn Leu Ala Asp Gly Val Pro Ser Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Val Ala Asp Tyr His Cys Leu Gln Tyr Asp Glu Tyr Pro Tyr
                85                  90                  95

```
Thr Phe Gly Ala Gly Thr Lys Leu Glu Leu Lys
            100                 105
```

```
<210> SEQ ID NO 65
<211> LENGTH: 122
<212> TYPE: PRT
<213> ORGANISM: Rattus norvegicus

<400> SEQUENCE: 65

Glu Val Gln Leu Val Glu Ser Asp Gly Gly Leu Ala Gln Pro Gly Arg
1               5                   10                  15

Ser Leu Lys Leu Ser Cys Ala Ala Ser Gly Phe Thr Phe Ser Asp Tyr
            20                  25                  30

Tyr Met Ala Trp Val Arg Gln Ala Pro Thr Lys Gly Leu Glu Trp Val
        35                  40                  45

Ala Thr Ile Ser Tyr Asp Gly Ser Ser Thr Tyr Tyr Arg Asp Ser Val
        50                  55                  60

Arg Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg Gly Pro Leu Thr Asp Trp Ala Pro Asn Trp Phe Ala Tyr Trp
            100                 105                 110

Gly Gln Gly Thr Leu Val Thr Val Ser Ser
        115                 120
```

```
<210> SEQ ID NO 66
<211> LENGTH: 107
<212> TYPE: PRT
<213> ORGANISM: Rattus norvegicus

<400> SEQUENCE: 66

Asp Ile Gln Met Thr Gln Ser Pro Ala Ser Leu Ser Ala Ser Leu Gly
1               5                   10                  15

Glu Thr Val Thr Ile Gln Cys Gln Thr Ser Glu Asp Ile Tyr Ser Gly
            20                  25                  30

Leu Ala Trp Tyr Gln Gln Lys Pro Gly Lys Ser Pro Gln Phe Leu Ile
        35                  40                  45

Tyr Gly Ala Ser Arg Leu Glu Asp Gly Val Pro Ser Arg Phe Ser Gly
        50                  55                  60

Ser Gly Ser Gly Thr Gln Tyr Ser Leu Lys Ile Ser Ser Met Gln Thr
65                  70                  75                  80

Glu Asp Glu Gly Val Tyr Phe Cys Gln Gln Gly Leu Lys Tyr Pro Asn
                85                  90                  95

Thr Phe Gly Ala Gly Thr Lys Leu Glu Leu Lys
            100                 105
```

```
<210> SEQ ID NO 67
<211> LENGTH: 121
<212> TYPE: PRT
<213> ORGANISM: Rattus norvegicus

<400> SEQUENCE: 67

Glu Val Gln Leu Val Glu Ser Gly Gly Gly Leu Val Gln Pro Gly Arg
1               5                   10                  15

Ser Leu Lys Leu Ser Cys Val Ala Ser Gly Phe Thr Phe Asn Asn Tyr
            20                  25                  30

Trp Met Thr Trp Ile Arg Gln Ala Pro Gly Lys Gly Leu Glu Trp Val
```

-continued

```
            35                  40                  45

Ala Ser Ile Thr Asn Thr Gly Gly Thr Thr Tyr Tyr Pro Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Thr Arg Gly Pro Thr Thr Val Val Gly Gly Trp Phe Ala Tyr Trp Gly
                100                 105                 110

Gln Gly Thr Leu Val Thr Val Ser Ser
        115                 120
```

<210> SEQ ID NO 68
<211> LENGTH: 107
<212> TYPE: PRT
<213> ORGANISM: Rattus norvegicus

<400> SEQUENCE: 68

```
Asp Ile Val Met Thr Gln Ser Pro Thr Ser Met Ser Ile Ser Val Gly
1               5                   10                  15

Asp Arg Val Thr Met Asn Cys Lys Ala Ser Gln Asn Val Gly Ser Asn
                20                  25                  30

Val Asp Trp Tyr Gln Gln Lys Thr Gly Gln Ser Pro Lys Val Leu Ile
            35                  40                  45

Tyr Arg Ala Ser Ser Arg Ser Thr Gly Val Pro Asp Arg Phe Thr Gly
    50                  55                  60

Ser Gly Ser Gly Thr Asp Phe Thr Phe Thr Ile Ser Asn Met Gln Ala
65                  70                  75                  80

Glu Asp Leu Ala Val Tyr Tyr Cys Met Gln Ser Asn Ser Tyr Pro Pro
                85                  90                  95

Thr Phe Gly Gly Gly Thr Lys Leu Glu Leu Lys
                100                 105
```

<210> SEQ ID NO 69
<211> LENGTH: 121
<212> TYPE: PRT
<213> ORGANISM: Rattus norvegicus

<400> SEQUENCE: 69

```
Glu Val Gln Leu Val Glu Ser Gly Gly Gly Leu Val Gln Pro Gly Arg
1               5                   10                  15

Ser Leu Lys Leu Ser Cys Val Ala Ser Gly Phe Thr Phe Asn Asn Tyr
                20                  25                  30

Trp Met Thr Trp Ile Arg Gln Ala Pro Gly Lys Gly Leu Glu Trp Val
            35                  40                  45

Ala Ser Ile Thr Asn Thr Gly Gly Ser Thr Tyr Tyr Pro Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Thr Arg Gly Pro Thr Thr Val Val Gly Gly Trp Phe Ala Tyr Trp Gly
                100                 105                 110

Gln Gly Thr Leu Val Thr Val Ser Ser
        115                 120
```

<210> SEQ ID NO 70
<211> LENGTH: 107
<212> TYPE: PRT
<213> ORGANISM: Rattus norvegicus

<400> SEQUENCE: 70

```
Asp Ile Val Met Thr Gln Ser Pro Thr Ser Met Ser Ile Ser Val Gly
1               5                   10                  15

Asp Arg Val Thr Met Asn Cys Lys Ala Ser Gln Asn Val Gly Ser Asn
            20                  25                  30

Val Asp Trp Tyr Gln Gln Lys Thr Gly Gln Ser Pro Lys Leu Leu Ile
        35                  40                  45

Tyr Arg Pro Ser Asn Arg Tyr Thr Gly Val Pro Asp Arg Phe Thr Gly
    50                  55                  60

Ser Gly Ser Gly Thr Asp Phe Thr Phe Thr Ile Ser Asn Met Gln Ala
65                  70                  75                  80

Glu Asp Leu Ala Val Tyr Tyr Cys Met Gln Ser Asn Ser Tyr Pro Pro
                85                  90                  95

Thr Phe Gly Gly Gly Thr Lys Leu Glu Leu Lys
            100                 105
```

<210> SEQ ID NO 71
<211> LENGTH: 122
<212> TYPE: PRT
<213> ORGANISM: Rattus norvegicus

<400> SEQUENCE: 71

```
Glu Val Gln Leu Val Glu Ser Gly Gly Gly Leu Val Gln Pro Gly Arg
1               5                   10                  15

Ser Leu Lys Leu Ser Cys Val Ala Ser Gly Phe Thr Phe Asn Asn Tyr
            20                  25                  30

Trp Met Thr Trp Ile Arg Gln Ala Pro Gly Lys Gly Leu Glu Trp Val
        35                  40                  45

Ala Ser Ile Thr Asn Thr Gly Gly Ser Thr Phe Tyr Pro Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Thr Arg Gly Pro Asp Tyr Gly Gly His Leu Asn Trp Phe Ala Tyr Trp
            100                 105                 110

Gly Gln Gly Thr Leu Val Thr Val Ser Ser
        115                 120
```

<210> SEQ ID NO 72
<211> LENGTH: 107
<212> TYPE: PRT
<213> ORGANISM: Rattus norvegicus

<400> SEQUENCE: 72

```
Asp Ile Val Met Thr Gln Ser Pro Thr Ser Met Ser Ile Ser Ala Gly
1               5                   10                  15

Asp Arg Val Thr Met Asn Cys Lys Ala Ser Gln Asn Val Gly Ser Asn
            20                  25                  30

Val Asp Trp Tyr Gln Gln Lys Thr Gly Gln Ser Pro Lys Leu Leu Ile
        35                  40                  45

Tyr Lys Ala Ser Asn Arg Tyr Thr Gly Val Pro Asp Arg Cys Thr Gly
    50                  55                  60
```

-continued

```
Ser Gly Ser Gly Thr Asp Phe Thr Phe Thr Ile Ser Asn Met Gln Ala
65                  70                  75                  80

Glu Asp Leu Ala Val Tyr Tyr Cys Met Gln Ser Asn Ser Tyr Pro Pro
                85                  90                  95

Thr Phe Gly Gly Gly Thr Lys Leu Glu Leu Lys
            100                 105
```

<210> SEQ ID NO 73
<211> LENGTH: 122
<212> TYPE: PRT
<213> ORGANISM: Rattus norvegicus

<400> SEQUENCE: 73

```
Glu Val Gln Leu Val Glu Ser Gly Gly Gly Leu Val Gln Pro Gly Arg
1               5                   10                  15

Ser Leu Lys Leu Ser Cys Val Ala Ser Gly Phe Thr Phe Asn Lys Tyr
                20                  25                  30

Trp Met Thr Trp Ile Arg Gln Ala Pro Gly Lys Gly Leu Glu Trp Val
            35                  40                  45

Ala Ser Ile Thr Asn Thr Gly Gly Ser Ser Tyr Tyr Ser Asp Ser Val
        50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ser Glu Glu Thr Ala Thr Tyr Tyr Cys
                85                  90                  95

Thr Arg Gly Pro Asp Tyr Gly Gly His Leu Asn Trp Phe Ala Tyr Trp
            100                 105                 110

Gly Gln Gly Thr Leu Val Thr Val Ser Ser
        115                 120
```

<210> SEQ ID NO 74
<211> LENGTH: 107
<212> TYPE: PRT
<213> ORGANISM: Rattus norvegicus

<400> SEQUENCE: 74

```
Asp Ile Val Met Thr Gln Ser Pro Thr Ser Met Ser Ile Ser Val Gly
1               5                   10                  15

Asp Arg Val Thr Met Asn Cys Lys Ala Ser Gln Asn Val Gly Ser Asn
                20                  25                  30

Val Asp Trp Tyr Gln Glu Lys Thr Gly Gln Ser Pro Lys Leu Val Ile
            35                  40                  45

Tyr Lys Ala Ser Asn Arg Tyr Thr Gly Val Pro Asp Arg Phe Thr Gly
        50                  55                  60

Ser Gly Ser Gly Thr Asp Phe Thr Phe Thr Ile Ser Asn Met Gln Ala
65                  70                  75                  80

Glu Asp Leu Ala Val Tyr Tyr Cys Met Gln Ser Asn Ser Tyr Pro Pro
                85                  90                  95

Thr Phe Gly Gly Gly Thr Lys Leu Glu Leu Lys
            100                 105
```

<210> SEQ ID NO 75
<211> LENGTH: 122
<212> TYPE: PRT
<213> ORGANISM: Rattus norvegicus

<400> SEQUENCE: 75

Glu Val Gln Leu Val Glu Ser Gly Gly Gly Leu Val Gln Pro Gly Arg
1               5                   10                  15

Thr Leu Lys Leu Phe Cys Val Ala Ser Gly Phe Thr Phe Asn Asn Tyr
            20                  25                  30

Trp Met Thr Trp Ile Arg Gln Ala Pro Gly Lys Gly Leu Glu Trp Val
            35                  40                  45

Ala Ser Ile Thr Asn Thr Gly Gly Ser Thr Tyr Tyr Pro Asp Ser Val
        50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Thr Arg Gly Pro Asp Tyr Gly Gly His Leu Asn Trp Phe Val Tyr Trp
            100                 105                 110

Gly Gln Gly Thr Leu Val Thr Val Ser Ser
            115                 120

<210> SEQ ID NO 76
<211> LENGTH: 107
<212> TYPE: PRT
<213> ORGANISM: Rattus norvegicus

<400> SEQUENCE: 76

Asp Ile Val Met Thr Gln Ser Pro Thr Ser Met Ser Ile Ser Val Gly
1               5                   10                  15

Asp Arg Val Thr Met Asn Cys Lys Ala Ser Gln Asn Val Gly Ser Asn
            20                  25                  30

Val Asp Trp Tyr Gln Gln Lys Thr Gly Gln Ser Pro Lys Leu Leu Ile
            35                  40                  45

Tyr Lys Ala Ser Asn Arg Tyr Thr Gly Val Pro Asp Arg Phe Thr Gly
        50                  55                  60

Ser Gly Ser Gly Thr Asp Phe Thr Phe Thr Ile Ser Asn Met Gln Ala
65                  70                  75                  80

Glu Asp Leu Ala Val Tyr Tyr Cys Met Gln Ser Asn Ser Tyr Pro Pro
                85                  90                  95

Thr Phe Gly Gly Gly Thr Lys Leu Glu Leu Lys
            100                 105

<210> SEQ ID NO 77
<211> LENGTH: 215
<212> TYPE: PRT
<213> ORGANISM: Canis lupus familiaris

<400> SEQUENCE: 77

Leu Gly Gly Pro Ser Val Phe Ile Phe Pro Pro Lys Pro Lys Asp Thr
1               5                   10                  15

Leu Leu Ile Ala Arg Thr Pro Glu Val Thr Cys Val Val Val Asp Leu
            20                  25                  30

Asp Pro Glu Asp Pro Glu Val Gln Ile Ser Trp Phe Val Asp Gly Lys
            35                  40                  45

Gln Met Gln Thr Ala Lys Thr Gln Pro Arg Glu Glu Gln Phe Asn Gly
        50                  55                  60

Thr Tyr Arg Val Val Ser Val Leu Pro Ile Gly His Gln Asp Trp Leu
65                  70                  75                  80

Lys Gly Lys Gln Phe Thr Cys Lys Val Asn Asn Lys Ala Leu Pro Ser
                85                  90                  95

```
Pro Ile Glu Arg Thr Ile Ser Lys Ala Arg Gly Gln Ala His Gln Pro
        100                 105                 110

Ser Val Tyr Val Leu Pro Pro Ser Arg Glu Glu Leu Ser Lys Asn Thr
        115                 120                 125

Val Ser Leu Thr Cys Leu Ile Lys Asp Phe Phe Pro Pro Asp Ile Asp
        130                 135                 140

Val Glu Trp Gln Ser Asn Gly Gln Gln Glu Pro Glu Ser Lys Tyr Arg
145                 150                 155                 160

Thr Thr Pro Pro Gln Leu Asp Glu Asp Gly Ser Tyr Phe Leu Tyr Ser
                165                 170                 175

Lys Leu Ser Val Asp Lys Ser Arg Trp Gln Arg Gly Asp Thr Phe Ile
        180                 185                 190

Cys Ala Val Met His Glu Ala Leu His Asn His Tyr Thr Gln Lys Ser
        195                 200                 205

Leu Ser His Ser Pro Gly Lys
        210                 215
```

```
<210> SEQ ID NO 78
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Modified canine"

<400> SEQUENCE: 78
```

```
Leu Gly Gly Pro Ser Val Phe Ile Phe Pro Pro Lys Pro Lys Asp Thr
1               5                   10                  15

Leu Leu Ile Ala Arg Thr Pro Glu Val Thr Cys Val Val Val Ala Leu
        20                  25                  30

Asp Pro Glu Asp Pro Glu Val Gln Ile Ser Trp Phe Val Asp Gly Lys
        35                  40                  45

Gln Met Gln Thr Ala Lys Thr Gln Pro Arg Glu Glu Gln Phe Ala Gly
        50                  55                  60

Thr Tyr Arg Val Val Ser Val Leu Pro Ile Gly His Gln Asp Trp Leu
65                  70                  75                  80

Lys Gly Lys Gln Phe Thr Cys Lys Val Asn Asn Lys Ala Leu Pro Ser
                85                  90                  95

Pro Ile Glu Arg Thr Ile Ser Lys Ala Arg Gly Gln Ala His Gln Pro
        100                 105                 110

Ser Val Tyr Val Leu Pro Pro Ser Arg Glu Glu Leu Ser Lys Asn Thr
        115                 120                 125

Val Ser Leu Thr Cys Leu Ile Lys Asp Phe Phe Pro Pro Asp Ile Asp
        130                 135                 140

Val Glu Trp Gln Ser Asn Gly Gln Gln Glu Pro Glu Ser Lys Tyr Arg
145                 150                 155                 160

Thr Thr Pro Pro Gln Leu Asp Glu Asp Gly Ser Tyr Phe Leu Tyr Ser
                165                 170                 175

Lys Leu Ser Val Asp Lys Ser Arg Trp Gln Arg Gly Asp Thr Phe Ile
        180                 185                 190

Cys Ala Val Met His Glu Ala Leu His Asn His Tyr Thr Gln Glu Ser
        195                 200                 205

Leu Ser His Ser Pro Gly
```

-continued

210

```
<210> SEQ ID NO 79
<211> LENGTH: 17
<212> TYPE: PRT
<213> ORGANISM: Canis lupus familiaris

<400> SEQUENCE: 79

Phe Asn Glu Cys Arg Cys Thr Asp Thr Pro Pro Cys Pro Val Pro Glu
1               5                   10                  15

Pro

<210> SEQ ID NO 80
<211> LENGTH: 22
<212> TYPE: PRT
<213> ORGANISM: Canis lupus familiaris

<400> SEQUENCE: 80

Pro Lys Arg Glu Asn Gly Arg Val Pro Arg Pro Pro Asp Cys Pro Lys
1               5                   10                  15

Cys Pro Ala Pro Glu Met
            20

<210> SEQ ID NO 81
<211> LENGTH: 20
<212> TYPE: PRT
<213> ORGANISM: Canis lupus familiaris

<400> SEQUENCE: 81

Ala Lys Glu Cys Glu Cys Lys Cys Asn Cys Asn Asn Cys Pro Cys Pro
1               5                   10                  15

Gly Cys Gly Leu
            20

<210> SEQ ID NO 82
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Modified canine"

<400> SEQUENCE: 82

Pro Lys Glu Ser Thr Cys Lys Cys Ile Pro Pro Cys Pro Val Pro Glu
1               5                   10                  15

Ser

<210> SEQ ID NO 83
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Gln Pro Val Leu Thr Gln Pro Pro Ser Leu Ser Ala Ser Leu Gly Thr
1               5                   10                  15

Thr Ala Arg Leu Thr Cys Glu Arg Ser Ser Gly Asp Ile Gly Asp Ser
```

-continued

```
                20                 25                 30

Tyr Val Ser Trp Tyr Gln Gln Lys Pro Gly Ser Pro Pro Arg Asp Leu
            35                 40                 45

Leu Tyr Val Asp Asp Gln Arg Pro Ser Gly Val Ser Lys Ser Phe Ser
        50                 55                 60

Gly Ser Lys Asp Thr Ser Ala Asn Ala Gly Leu Leu Leu Ile Ser Gly
65                 70                 75                 80

Leu Gln Pro Glu Asp Glu Ala Asp Tyr Tyr Cys Gln Ser Tyr Asp Ser
                85                 90                 95

Asn Ile Asp Gly Pro Val Phe Gly Gly Gly Thr His Leu Thr Val Leu
            100                105                110

Gly Gln Pro Lys Ala Ser Pro Ser Val Thr Leu Phe Pro Pro Ser Ser
        115                120                125

Glu Glu Leu Gly Ala Asn Lys Ala Thr Leu Val Cys Leu Ile Ser Asp
        130                135                140

Phe Tyr Pro Ser Gly Val Thr Val Ala Trp Lys Ala Asp Gly Ser Pro
145                150                155                160

Val Thr Gln Gly Val Glu Thr Thr Lys Pro Ser Lys Gln Ser Asn Asn
                165                170                175

Lys Tyr Ala Ala Ser Ser Tyr Leu Ser Leu Thr Pro Asp Lys Trp Lys
            180                185                190

Ser His Ser Ser Phe Ser Cys Leu Val Thr His Glu Gly Ser Thr Val
            195                200                205

Glu Lys Lys Val Ala Pro Ala Glu Cys Ser
        210                215
```

<210> SEQ ID NO 84
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Caninized rat"

<400> SEQUENCE: 84

```
Glu Val Gln Leu Val Glu Ser Gly Gly Asp Leu Val Lys Pro Gly Gly
1               5                  10                 15

Ser Leu Arg Leu Ser Cys Val Ala Ser Gly Phe Thr Phe Ser Asn Tyr
            20                 25                 30

Tyr Met Ala Trp Val Arg Gln Ala Pro Gly Lys Gly Leu Gln Trp Val
            35                 40                 45

Ala Ser Ile Ser Thr Gly Gly Gly Asn Thr Tyr Tyr Arg Asp Ser Val
        50                 55                 60

Lys Gly Arg Phe Thr Ile Ser Arg Asp Asn Ala Lys Asn Thr Leu Tyr
65                 70                 75                 80

Leu Gln Met Asn Ser Leu Arg Ala Glu Asp Thr Ala Met Tyr Tyr Cys
                85                 90                 95

Ala Lys His Gly Thr Leu Tyr Phe Asp Tyr Trp Gly Gln Gly Thr Leu
            100                105                110

Val Thr Val Ser Ser Ala Ser Thr Thr Ala Pro Ser Val Phe Pro Leu
        115                120                125

Ala Pro Ser Cys Gly Ser Thr Ser Gly Ser Thr Val Ala Leu Ala Cys
        130                135                140
```

-continued

```
Leu Val Ser Gly Tyr Phe Pro Glu Pro Val Thr Val Ser Trp Asn Ser
145                 150                 155                 160

Gly Ser Leu Thr Ser Gly Val His Thr Phe Pro Ser Val Leu Gln Ser
                165                 170                 175

Ser Gly Leu Tyr Ser Leu Ser Ser Met Val Thr Val Pro Ser Ser Arg
                180                 185                 190

Trp Pro Ser Glu Thr Phe Thr Cys Asn Val Ala His Pro Ala Ser Lys
            195                 200                 205

Thr Lys Val Asp Lys Pro Val Pro Lys Arg Glu Asn Gly Arg Val Pro
        210                 215                 220

Arg Pro Pro Asp Cys Pro Lys Cys Pro Ala Pro Glu Met Leu Gly Gly
225                 230                 235                 240

Pro Ser Val Phe Ile Phe Pro Pro Lys Pro Lys Asp Thr Leu Leu Ile
                245                 250                 255

Ala Arg Thr Pro Glu Val Thr Cys Val Val Val Ala Leu Asp Pro Glu
                260                 265                 270

Asp Pro Glu Val Gln Ile Ser Trp Phe Val Asp Gly Lys Gln Met Gln
            275                 280                 285

Thr Ala Lys Thr Gln Pro Arg Glu Glu Gln Phe Ala Gly Thr Tyr Arg
        290                 295                 300

Val Val Ser Val Leu Pro Ile Gly His Gln Asp Trp Leu Lys Gly Lys
305                 310                 315                 320

Gln Phe Thr Cys Lys Val Asn Asn Lys Ala Leu Pro Ser Pro Ile Glu
                325                 330                 335

Arg Thr Ile Ser Lys Ala Arg Gly Gln Ala His Gln Pro Ser Val Tyr
            340                 345                 350

Val Leu Pro Pro Ser Arg Glu Glu Leu Ser Lys Asn Thr Val Ser Leu
            355                 360                 365

Thr Cys Leu Ile Lys Asp Phe Phe Pro Pro Asp Ile Asp Val Glu Trp
    370                 375                 380

Gln Ser Asn Gly Gln Gln Glu Pro Glu Ser Lys Tyr Arg Thr Thr Pro
385                 390                 395                 400

Pro Gln Leu Asp Glu Asp Gly Ser Tyr Phe Leu Tyr Ser Lys Leu Ser
                405                 410                 415

Val Asp Lys Ser Arg Trp Gln Arg Gly Asp Thr Phe Ile Cys Ala Val
            420                 425                 430

Met His Glu Ala Leu His Asn His Tyr Thr Gln Glu Ser Leu Ser His
        435                 440                 445

Ser Pro Gly Lys
    450

<210> SEQ ID NO 85
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Glu Val Gln Leu Val Glu Ser Gly Gly Asp Leu Val Lys Pro Gly Gly
1               5                   10                  15

Ser Leu Arg Leu Ser Cys Ala Ala Ser Gly Phe Thr Phe Ser Asn Tyr
                20                  25                  30
```

-continued

Tyr Met Ala Trp Val Arg Gln Ala Pro Gly Lys Gly Leu Gln Trp Val
    35             40             45

Ala Ser Ile Ser Thr Gly Gly Gly Asn Thr Tyr Tyr Arg Asp Ser Val
    50             55             60

Lys Gly Arg Phe Thr Ile Ser Arg Asp Asn Ala Lys Asn Thr Leu Tyr
65             70             75             80

Leu Gln Met Asn Ser Leu Arg Ala Glu Asp Thr Ala Met Tyr Tyr Cys
            85            90            95

Ala Arg His Gly Thr Leu Tyr Phe Asp Tyr Trp Gly Gln Gly Thr Leu
        100           105          110

Val Thr Val Ser Ser Ala Ser Thr Thr Ala Pro Ser Val Phe Pro Leu
        115           120          125

Ala Pro Ser Cys Gly Ser Thr Ser Gly Ser Thr Val Ala Leu Ala Cys
    130          135           140

Leu Val Ser Gly Tyr Phe Pro Glu Pro Val Thr Val Ser Trp Asn Ser
145          150          155           160

Gly Ser Leu Thr Ser Gly Val His Thr Phe Pro Ser Val Leu Gln Ser
        165           170          175

Ser Gly Leu Tyr Ser Leu Ser Ser Met Val Thr Val Pro Ser Ser Arg
        180           185          190

Trp Pro Ser Glu Thr Phe Thr Cys Asn Val Ala His Pro Ala Ser Lys
        195           200          205

Thr Lys Val Asp Lys Pro Val Pro Lys Arg Glu Asn Gly Arg Val Pro
    210          215          220

Arg Pro Pro Asp Cys Pro Lys Cys Pro Ala Pro Glu Met Leu Gly Gly
225          230          235           240

Pro Ser Val Phe Ile Phe Pro Pro Lys Pro Lys Asp Thr Leu Leu Ile
        245           250          255

Ala Arg Thr Pro Glu Val Thr Cys Val Val Val Ala Leu Asp Pro Glu
        260           265          270

Asp Pro Glu Val Gln Ile Ser Trp Phe Val Asp Gly Lys Gln Met Gln
        275           280          285

Thr Ala Lys Thr Gln Pro Arg Glu Glu Gln Phe Ala Gly Thr Tyr Arg
    290          295          300

Val Val Ser Val Leu Pro Ile Gly His Gln Asp Trp Leu Lys Gly Lys
305          310          315          320

Gln Phe Thr Cys Lys Val Asn Asn Lys Ala Leu Pro Ser Pro Ile Glu
        325           330          335

Arg Thr Ile Ser Lys Ala Arg Gly Gln Ala His Gln Pro Ser Val Tyr
        340           345          350

Val Leu Pro Pro Ser Arg Glu Glu Leu Ser Lys Asn Thr Val Ser Leu
        355           360          365

Thr Cys Leu Ile Lys Asp Phe Phe Pro Pro Asp Ile Asp Val Glu Trp
    370          375          380

Gln Ser Asn Gly Gln Gln Glu Pro Glu Ser Lys Tyr Arg Thr Thr Pro
385          390          395           400

Pro Gln Leu Asp Glu Asp Gly Ser Tyr Phe Leu Tyr Ser Lys Leu Ser
        405           410          415

Val Asp Lys Ser Arg Trp Gln Arg Gly Asp Thr Phe Ile Cys Ala Val
        420           425          430

Met His Glu Ala Leu His Asn His Tyr Thr Gln Glu Ser Leu Ser His
        435           440          445

Ser Pro Gly Lys

-continued

450

```
<210> SEQ ID NO 86
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Gln Ser Val Leu Thr Gln Pro Ala Ser Val Ser Gly Ser Leu Gly Gln
1               5                   10                  15

Arg Val Thr Ile Ser Cys Glu Arg Ser Ser Gly Asp Ile Gly Asp Ser
            20                  25                  30

Tyr Val Ser Trp Tyr Gln Gln Leu Pro Gly Lys Ala Pro Ser Leu Leu
            35                  40                  45

Ile Tyr Val Asp Asp Gln Arg Pro Ser Gly Val Pro Glu Arg Phe Ser
        50                  55                  60

Gly Ser Lys Ser Gly Ser Ser Asn Ser Ala Thr Leu Thr Ile Thr Gly
65                  70                  75                  80

Leu Gln Ala Glu Asp Glu Ala Asp Tyr Tyr Cys Gln Ser Tyr Asp Ser
                85                  90                  95

Asn Ile Asp Gly Pro Val Phe Gly Gly Gly Thr His Leu Thr Val Leu
            100                 105                 110

Gly Gln Pro Lys Ala Ser Pro Ser Val Thr Leu Phe Pro Pro Ser Ser
            115                 120                 125

Glu Glu Leu Gly Ala Asn Lys Ala Thr Leu Val Cys Leu Ile Ser Asp
        130                 135                 140

Phe Tyr Pro Ser Gly Val Thr Val Ala Trp Lys Ala Asp Gly Ser Pro
145                 150                 155                 160

Val Thr Gln Gly Val Glu Thr Thr Lys Pro Ser Lys Gln Ser Asn Asn
                165                 170                 175

Lys Tyr Ala Ala Ser Ser Tyr Leu Ser Leu Thr Pro Asp Lys Trp Lys
                180                 185                 190

Ser His Ser Ser Phe Ser Cys Leu Val Thr His Glu Gly Ser Thr Val
                195                 200                 205

Glu Lys Lys Val Ala Pro Ala Glu Cys Ser
        210                 215

<210> SEQ ID NO 87
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Gln Pro Val Leu Thr Gln Pro Pro Ser Leu Ser Ala Ser Leu Gly Thr
1               5                   10                  15

Thr Ala Arg Leu Thr Cys Glu Arg Ser Ser Gly Asp Ile Gly Asp Ser
            20                  25                  30

Tyr Val Ser Trp Tyr Gln Gln Lys Pro Gly Ser Pro Pro Arg Asp Val
            35                  40                  45

Ile Tyr Val Asp Asp Gln Arg Pro Ser Glu Val Ser Lys Ser Phe Ser
        50                  55                  60
```

```
Gly Ser Lys Asp Thr Ser Ala Asn Ala Gly Leu Leu Leu Ile Ser Gly
65                  70                  75                  80

Leu Gln Pro Glu Asp Glu Ala Asp Tyr Phe Cys Gln Ser Tyr Asp Ser
                85                  90                  95

Asn Ile Asp Gly Pro Val Phe Gly Gly Gly Thr His Leu Thr Val Leu
                100                 105                 110

Gly Gln Pro Lys Ala Ser Pro Ser Val Thr Leu Phe Pro Pro Ser Ser
            115                 120                 125

Glu Glu Leu Gly Ala Asn Lys Ala Thr Leu Val Cys Leu Ile Ser Asp
    130                 135                 140

Phe Tyr Pro Ser Gly Val Thr Val Ala Trp Lys Ala Asp Gly Ser Pro
145                 150                 155                 160

Val Thr Gln Gly Val Glu Thr Thr Lys Pro Ser Lys Gln Ser Asn Asn
                165                 170                 175

Lys Tyr Ala Ala Ser Ser Tyr Leu Ser Leu Thr Pro Asp Lys Trp Lys
                180                 185                 190

Ser His Ser Ser Phe Ser Cys Leu Val Thr His Glu Gly Ser Thr Val
        195                 200                 205

Glu Lys Lys Val Ala Pro Ala Glu Cys Ser
    210                 215
```

```
<210> SEQ ID NO 88
<211> LENGTH: 457
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88
```

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asp Tyr
                20                  25                  30

Tyr Met Ala Trp Val Arg Gln Ala Pro Gly Lys Gly Leu Gln Trp Val
            35                  40                  45

Ala Thr Ile Ser Tyr Asp Gly Ser Ser Thr Tyr Tyr Arg Asp Ser Val
    50                  55                  60

Arg Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Lys Gly Pro Leu Thr Asp Trp Ala Pro Asn Trp Phe Ala Tyr Trp
            100                 105                 110

Gly Gln Gly Thr Leu Val Thr Val Ser Ser Ala Ser Thr Thr Ala Pro
            115                 120                 125

Ser Val Phe Pro Leu Ala Pro Ser Cys Gly Ser Thr Ser Gly Ser Thr
        130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu Tyr Ser Leu Ser Ser Met Val Thr
        180                 185                 190
```

-continued

```
Val Pro Ser Ser Arg Trp Pro Ser Glu Thr Phe Thr Cys Asn Val Ala
        195                 200                 205

His Pro Ala Ser Lys Thr Lys Val Asp Lys Pro Val Pro Lys Arg Glu
    210                 215                 220

Asn Gly Arg Val Pro Arg Pro Pro Asp Cys Pro Lys Cys Pro Ala Pro
225                 230                 235                 240

Glu Met Leu Gly Gly Pro Ser Val Phe Ile Phe Pro Pro Lys Pro Lys
            245                 250                 255

Asp Thr Leu Leu Ile Ala Arg Thr Pro Glu Val Thr Cys Val Val Val
            260                 265                 270

Ala Leu Asp Pro Glu Asp Pro Glu Val Gln Ile Ser Trp Phe Val Asp
            275                 280                 285

Gly Lys Gln Met Gln Thr Ala Lys Thr Gln Pro Arg Glu Glu Gln Phe
    290                 295                 300

Ala Gly Thr Tyr Arg Val Val Ser Val Leu Pro Ile Gly His Gln Asp
305                 310                 315                 320

Trp Leu Lys Gly Lys Gln Phe Thr Cys Lys Val Asn Asn Lys Ala Leu
            325                 330                 335

Pro Ser Pro Ile Glu Arg Thr Ile Ser Lys Ala Arg Gly Gln Ala His
            340                 345                 350

Gln Pro Ser Val Tyr Val Leu Pro Pro Ser Arg Glu Glu Leu Ser Lys
    355                 360                 365

Asn Thr Val Ser Leu Thr Cys Leu Ile Lys Asp Phe Phe Pro Pro Asp
    370                 375                 380

Ile Asp Val Glu Trp Gln Ser Asn Gly Gln Gln Glu Pro Glu Ser Lys
385                 390                 395                 400

Tyr Arg Thr Thr Pro Pro Gln Leu Asp Glu Asp Gly Ser Tyr Phe Leu
            405                 410                 415

Tyr Ser Lys Leu Ser Val Asp Lys Ser Arg Trp Gln Arg Gly Asp Thr
            420                 425                 430

Phe Ile Cys Ala Val Met His Glu Ala Leu His Asn His Tyr Thr Gln
            435                 440                 445

Glu Ser Leu Ser His Ser Pro Gly Lys
    450                 455
```

```
<210> SEQ ID NO 89
<211> LENGTH: 457
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89
```

```
Glu Val Gln Leu Val Glu Ser Gly Gly Asp Leu Val Lys Pro Gly Gly
1               5                   10                  15

Ser Leu Arg Leu Ser Cys Ala Ala Ser Gly Phe Thr Phe Ser Asp Tyr
        20                  25                  30

Tyr Met Ala Trp Val Arg Gln Ala Pro Gly Lys Gly Leu Gln Trp Val
        35                  40                  45

Ala Thr Ile Ser Tyr Asp Gly Ser Ser Thr Tyr Tyr Arg Asp Ser Val
    50                  55                  60

Arg Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
```

-continued

```
              85              90              95

Ala Arg Gly Pro Leu Thr Asp Trp Ala Pro Asn Trp Phe Ala Tyr Trp
            100             105             110

Gly Gln Gly Thr Leu Val Thr Val Ser Ser Ala Ser Thr Thr Ala Pro
            115             120             125

Ser Val Phe Pro Leu Ala Pro Ser Cys Gly Ser Thr Ser Gly Ser Thr
            130             135             140

Val Ala Leu Ala Cys Leu Val Ser Gly Tyr Phe Pro Glu Pro Val Thr
145             150             155             160

Val Ser Trp Asn Ser Gly Ser Leu Thr Ser Gly Val His Thr Phe Pro
            165             170             175

Ser Val Leu Gln Ser Ser Gly Leu Tyr Ser Leu Ser Ser Met Val Thr
            180             185             190

Val Pro Ser Ser Arg Trp Pro Ser Glu Thr Phe Thr Cys Asn Val Ala
            195             200             205

His Pro Ala Ser Lys Thr Lys Val Asp Lys Pro Val Pro Lys Arg Glu
            210             215             220

Asn Gly Arg Val Pro Arg Pro Pro Asp Cys Pro Lys Cys Pro Ala Pro
225             230             235             240

Glu Met Leu Gly Gly Pro Ser Val Phe Ile Phe Pro Pro Lys Pro Lys
            245             250             255

Asp Thr Leu Leu Ile Ala Arg Thr Pro Glu Val Thr Cys Val Val Val
            260             265             270

Ala Leu Asp Pro Glu Asp Pro Glu Val Gln Ile Ser Trp Phe Val Asp
            275             280             285

Gly Lys Gln Met Gln Thr Ala Lys Thr Gln Pro Arg Glu Glu Gln Phe
            290             295             300

Ala Gly Thr Tyr Arg Val Val Ser Val Leu Pro Ile Gly His Gln Asp
305             310             315             320

Trp Leu Lys Gly Lys Gln Phe Thr Cys Lys Val Asn Asn Lys Ala Leu
            325             330             335

Pro Ser Pro Ile Glu Arg Thr Ile Ser Lys Ala Arg Gly Gln Ala His
            340             345             350

Gln Pro Ser Val Tyr Val Leu Pro Pro Ser Arg Glu Glu Leu Ser Lys
            355             360             365

Asn Thr Val Ser Leu Thr Cys Leu Ile Lys Asp Phe Phe Pro Pro Asp
            370             375             380

Ile Asp Val Glu Trp Gln Ser Asn Gly Gln Gln Glu Pro Glu Ser Lys
385             390             395             400

Tyr Arg Thr Thr Pro Pro Gln Leu Asp Glu Asp Gly Ser Tyr Phe Leu
            405             410             415

Tyr Ser Lys Leu Ser Val Asp Lys Ser Arg Trp Gln Arg Gly Asp Thr
            420             425             430

Phe Ile Cys Ala Val Met His Glu Ala Leu His Asn His Tyr Thr Gln
            435             440             445

Glu Ser Leu Ser His Ser Pro Gly Lys
            450             455
```

<210> SEQ ID NO 90
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 90

```
Asp Ile Val Met Thr Gln Thr Pro Leu Ser Leu Ser Val Ser Pro Gly
1               5                   10                  15

Glu Thr Ala Ser Ile Ser Cys Gln Thr Ser Glu Asp Ile Tyr Ser Gly
            20                  25                  30

Leu Ala Trp Phe Arg Gln Lys Pro Gly Gln Ser Pro Gln Arg Leu Ile
        35                  40                  45

Tyr Gly Ala Ser Arg Leu Glu Asp Gly Val Pro Asp Arg Phe Ser Gly
    50                  55                  60

Ser Gly Ser Gly Thr Asp Phe Thr Leu Arg Ile Ser Thr Val Glu Ala
65                  70                  75                  80

Asp Asp Thr Gly Val Tyr Tyr Cys Gln Gln Gly Leu Lys Tyr Pro Asn
                85                  90                  95

Thr Phe Gly Ala Gly Thr Lys Val Glu Leu Lys Arg Asn Asp Ala Gln
            100                 105                 110

Pro Ala Val Tyr Leu Phe Gln Pro Ser Pro Asp Gln Leu His Thr Gly
            115                 120                 125

Ser Ala Ser Val Val Cys Leu Leu Asn Ser Phe Tyr Pro Lys Asp Ile
    130                 135                 140

Asn Val Lys Trp Lys Val Asp Gly Val Ile Gln Asp Thr Gly Ile Gln
145                 150                 155                 160

Glu Ser Val Thr Glu Gln Asp Lys Asp Ser Thr Tyr Ser Leu Ser Ser
            165                 170                 175

Thr Leu Thr Met Ser Ser Thr Glu Tyr Leu Ser His Glu Leu Tyr Ser
            180                 185                 190

Cys Glu Ile Thr His Lys Ser Leu Pro Ser Thr Leu Ile Lys Ser Phe
            195                 200                 205

Gln Arg Ser Glu Cys Gln Arg Val Asp
    210                 215
```

<210> SEQ ID NO 91
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

```
Glu Ile Val Met Thr Gln Ser Pro Ala Ser Leu Ser Leu Ser Gln Glu
1               5                   10                  15

Glu Lys Val Thr Ile Thr Cys Gln Thr Ser Glu Asp Ile Tyr Ser Gly
            20                  25                  30

Leu Ala Trp Tyr Gln Gln Lys Pro Gly Gln Ala Pro Lys Leu Leu Ile
        35                  40                  45

Tyr Gly Ala Ser Arg Leu Glu Asp Gly Val Pro Ser Arg Phe Ser Gly
    50                  55                  60

Ser Gly Ser Gly Thr Asp Phe Ser Phe Thr Ile Ser Ser Leu Glu Pro
65                  70                  75                  80

Glu Asp Val Ala Val Tyr Tyr Cys Gln Gln Gly Leu Lys Tyr Pro Asn
                85                  90                  95

Thr Phe Gly Ala Gly Thr Lys Val Glu Leu Lys Arg Asn Asp Ala Gln
            100                 105                 110
```

```
Pro Ala Val Tyr Leu Phe Gln Pro Ser Pro Asp Gln Leu His Thr Gly
        115                 120                 125

Ser Ala Ser Val Val Cys Leu Leu Asn Ser Phe Tyr Pro Lys Asp Ile
    130                 135                 140

Asn Val Lys Trp Lys Val Asp Gly Val Ile Gln Asp Thr Gly Ile Gln
145                 150                 155                 160

Glu Ser Val Thr Glu Gln Asp Lys Asp Ser Thr Tyr Ser Leu Ser Ser
                165                 170                 175

Thr Leu Thr Met Ser Ser Thr Glu Tyr Leu Ser His Glu Leu Tyr Ser
            180                 185                 190

Cys Glu Ile Thr His Lys Ser Leu Pro Ser Thr Leu Ile Lys Ser Phe
        195                 200                 205

Gln Arg Ser Glu Cys Gln Arg Val Asp
    210                 215
```

```
<210> SEQ ID NO 92
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92
```

```
Asp Ile Val Met Thr Gln Ser Pro Ala Ser Leu Ser Leu Ser Gln Glu
1               5                   10                  15

Glu Lys Val Thr Ile Thr Cys Gln Thr Ser Glu Asp Ile Tyr Ser Gly
            20                  25                  30

Leu Ala Trp Tyr Gln Gln Lys Pro Gly Gln Ala Pro Lys Leu Leu Ile
        35                  40                  45

Tyr Gly Ala Ser Arg Leu Glu Asp Gly Val Pro Ser Arg Phe Ser Gly
    50                  55                  60

Ser Gly Ser Gly Thr Asp Phe Ser Phe Thr Ile Ser Ser Leu Glu Pro
65                  70                  75                  80

Glu Asp Val Ala Val Tyr Phe Cys Gln Gln Gly Leu Lys Tyr Pro Asn
                85                  90                  95

Thr Phe Gly Ala Gly Thr Lys Val Glu Leu Lys Arg Asn Asp Ala Gln
            100                 105                 110

Pro Ala Val Tyr Leu Phe Gln Pro Ser Pro Asp Gln Leu His Thr Gly
        115                 120                 125

Ser Ala Ser Val Val Cys Leu Leu Asn Ser Phe Tyr Pro Lys Asp Ile
    130                 135                 140

Asn Val Lys Trp Lys Val Asp Gly Val Ile Gln Asp Thr Gly Ile Gln
145                 150                 155                 160

Glu Ser Val Thr Glu Gln Asp Lys Asp Ser Thr Tyr Ser Leu Ser Ser
                165                 170                 175

Thr Leu Thr Met Ser Ser Thr Glu Tyr Leu Ser His Glu Leu Tyr Ser
            180                 185                 190

Cys Glu Ile Thr His Lys Ser Leu Pro Ser Thr Leu Ile Lys Ser Phe
        195                 200                 205

Gln Arg Ser Glu Cys Gln Arg Val Asp
    210                 215
```

```
<210> SEQ ID NO 93
<211> LENGTH: 217
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Asp Ile Val Met Thr Gln Thr Pro Leu Ser Leu Ser Val Ser Pro Gly
1               5                   10                  15

Glu Thr Ala Ser Ile Ser Cys Gln Thr Ser Glu Asp Ile Tyr Ser Gly
            20                  25                  30

Leu Ala Trp Phe Arg Gln Lys Pro Gly Gln Ser Pro Gln Leu Leu Ile
        35                  40                  45

Tyr Gly Ala Ser Arg Leu Glu Asp Gly Val Pro Asp Arg Phe Ser Gly
    50                  55                  60

Ser Gly Ser Gly Thr Asp Phe Thr Leu Arg Ile Ser Thr Val Glu Ala
65                  70                  75                  80

Asp Asp Thr Gly Val Tyr Phe Cys Gln Gln Gly Leu Lys Tyr Pro Asn
                85                  90                  95

Thr Phe Gly Ala Gly Thr Lys Val Glu Leu Lys Arg Asn Asp Ala Gln
            100                 105                 110

Pro Ala Val Tyr Leu Phe Gln Pro Ser Pro Asp Gln Leu His Thr Gly
            115                 120                 125

Ser Ala Ser Val Val Cys Leu Leu Asn Ser Phe Tyr Pro Lys Asp Ile
        130                 135                 140

Asn Val Lys Trp Lys Val Asp Gly Val Ile Gln Asp Thr Gly Ile Gln
145                 150                 155                 160

Glu Ser Val Thr Glu Gln Asp Lys Asp Ser Thr Tyr Ser Leu Ser Ser
            165                 170                 175

Thr Leu Thr Met Ser Ser Thr Glu Tyr Leu Ser His Glu Leu Tyr Ser
            180                 185                 190

Cys Glu Ile Thr His Lys Ser Leu Pro Ser Thr Leu Ile Lys Ser Phe
        195                 200                 205

Gln Arg Ser Glu Cys Gln Arg Val Asp
    210                 215

<210> SEQ ID NO 94
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Glu Val Gln Leu Val Glu Ser Gly Gly Asp Leu Val Lys Pro Glu Gly
1               5                   10                  15

Ser Leu Arg Leu Ser Cys Val Val Ser Gly Phe Thr Phe Ser Ser Asn
            20                  25                  30

Gly Val Ser Trp Val Arg Gln Ala Pro Gly Lys Gly Leu Gln Trp Val
        35                  40                  45

Ala Ala Ile Ser Ser Gly Gly Ser Thr Tyr Tyr Asn Ser Val Leu Lys
    50                  55                  60

Ser Arg Phe Thr Ile Ser Arg Asp Asn Ala Lys Asn Thr Leu Tyr Leu
65                  70                  75                  80

Gln Met Asn Ser Leu Arg Thr Glu Asp Thr Ala Val Tyr Tyr Cys Ala
            85                  90                  95
```

```
Lys Arg Leu Ser Gly Tyr Asn Tyr Val Pro Phe Ala Tyr Trp Gly Gln
            100                 105                 110

Gly Thr Leu Val Thr Val Ser Ser Ala Ser Thr Thr Ala Pro Ser Val
            115                 120                 125

Phe Pro Leu Ala Pro Ser Cys Gly Ser Thr Ser Gly Ser Thr Val Ala
            130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu Tyr Ser Leu Ser Ser Met Val Thr Val Pro
            180                 185                 190

Ser Ser Arg Trp Pro Ser Glu Thr Phe Thr Cys Asn Val Ala His Pro
            195                 200                 205

Ala Ser Lys Thr Lys Val Asp Lys Pro Val Pro Lys Arg Glu Asn Gly
            210                 215                 220

Arg Val Pro Arg Pro Pro Asp Cys Pro Lys Cys Pro Ala Pro Glu Met
225                 230                 235                 240

Leu Gly Gly Pro Ser Val Phe Ile Phe Pro Pro Lys Pro Lys Asp Thr
                245                 250                 255

Leu Leu Ile Ala Arg Thr Pro Glu Val Thr Cys Val Val Val Ala Leu
            260                 265                 270

Asp Pro Glu Asp Pro Glu Val Gln Ile Ser Trp Phe Val Asp Gly Lys
            275                 280                 285

Gln Met Gln Thr Ala Lys Thr Gln Pro Arg Glu Glu Gln Phe Ala Gly
            290                 295                 300

Thr Tyr Arg Val Val Ser Val Leu Pro Ile Gly His Gln Asp Trp Leu
305                 310                 315                 320

Lys Gly Lys Gln Phe Thr Cys Lys Val Asn Asn Lys Ala Leu Pro Ser
                325                 330                 335

Pro Ile Glu Arg Thr Ile Ser Lys Ala Arg Gly Gln Ala His Gln Pro
            340                 345                 350

Ser Val Tyr Val Leu Pro Pro Ser Arg Glu Glu Leu Ser Lys Asn Thr
            355                 360                 365

Val Ser Leu Thr Cys Leu Ile Lys Asp Phe Phe Pro Pro Asp Ile Asp
370                 375                 380

Val Glu Trp Gln Ser Asn Gly Gln Gln Glu Pro Glu Ser Lys Tyr Arg
385                 390                 395                 400

Thr Thr Pro Pro Gln Leu Asp Glu Asp Gly Ser Tyr Phe Leu Tyr Ser
                405                 410                 415

Lys Leu Ser Val Asp Lys Ser Arg Trp Gln Arg Gly Asp Thr Phe Ile
            420                 425                 430

Cys Ala Val Met His Glu Ala Leu His Asn His Tyr Thr Gln Glu Ser
            435                 440                 445

Leu Ser His Ser Pro Gly Lys
    450                 455
```

<210> SEQ ID NO 95
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

-continued

<400> SEQUENCE: 95

Glu Leu Thr Leu Gln Glu Ser Gly Pro Gly Leu Val Lys Pro Ser Gln
1               5                   10                  15

Thr Leu Ser Leu Thr Cys Val Val Ser Gly Gly Ser Val Thr Ser Asn
            20                  25                  30

Gly Val Ser Trp Ile Arg Gln Arg Pro Gly Arg Gly Leu Glu Trp Met
        35                  40                  45

Gly Ala Ile Ser Ser Gly Gly Ser Thr Tyr Tyr Asn Ser Val Leu Lys
    50                  55                  60

Ser Arg Ile Ser Ile Thr Ala Asp Thr Ala Lys Asn Gln Phe Ser Leu
65                  70                  75                  80

Gln Leu Ser Ser Met Thr Thr Glu Asp Thr Ala Val Tyr Tyr Cys Ala
                85                  90                  95

Arg Arg Leu Ser Gly Tyr Asn Tyr Val Pro Phe Ala Tyr Trp Gly Gln
            100                 105                 110

Gly Thr Leu Val Thr Val Ser Ser Ala Ser Thr Thr Ala Pro Ser Val
            115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu Tyr Ser Leu Ser Ser Met Val Thr Val Pro
            180                 185                 190

Ser Ser Arg Trp Pro Ser Glu Thr Phe Thr Cys Asn Val Ala His Pro
            195                 200                 205

Ala Ser Lys Thr Lys Val Asp Lys Pro Val Pro Lys Arg Glu Asn Gly
    210                 215                 220

Arg Val Pro Arg Pro Pro Asp Cys Pro Lys Cys Pro Ala Pro Glu Met
225                 230                 235                 240

Leu Gly Gly Pro Ser Val Phe Ile Phe Pro Pro Lys Pro Lys Asp Thr
                245                 250                 255

Leu Leu Ile Ala Arg Thr Pro Glu Val Thr Cys Val Val Val Ala Leu
            260                 265                 270

Asp Pro Glu Asp Pro Glu Val Gln Ile Ser Trp Phe Val Asp Gly Lys
    275                 280                 285

Gln Met Gln Thr Ala Lys Thr Gln Pro Arg Glu Glu Gln Phe Ala Gly
    290                 295                 300

Thr Tyr Arg Val Val Ser Val Leu Pro Ile Gly His Gln Asp Trp Leu
305                 310                 315                 320

Lys Gly Lys Gln Phe Thr Cys Lys Val Asn Asn Lys Ala Leu Pro Ser
                325                 330                 335

Pro Ile Glu Arg Thr Ile Ser Lys Ala Arg Gly Gln Ala His Gln Pro
            340                 345                 350

Ser Val Tyr Val Leu Pro Pro Ser Arg Glu Glu Leu Ser Lys Asn Thr
            355                 360                 365

Val Ser Leu Thr Cys Leu Ile Lys Asp Phe Phe Pro Pro Asp Ile Asp
    370                 375                 380

Val Glu Trp Gln Ser Asn Gly Gln Gln Glu Pro Glu Ser Lys Tyr Arg
385                 390                 395                 400

Thr Thr Pro Pro Gln Leu Asp Glu Asp Gly Ser Tyr Phe Leu Tyr Ser

-continued

```
                    405                    410                    415

Lys Leu Ser Val Asp Lys Ser Arg Trp Gln Arg Gly Asp Thr Phe Ile
            420                    425                    430

Cys Ala Val Met His Glu Ala Leu His Asn His Tyr Thr Gln Glu Ser
        435                    440                    445

Leu Ser His Ser Pro Gly Lys
    450                    455

<210> SEQ ID NO 96
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Glu Leu Thr Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Ser Asn
            20                  25                  30

Gly Val Ser Trp Ile Arg Gln Arg Pro Gly Arg Gly Leu Glu Trp Met
        35                  40                  45

Gly Ala Ile Ser Ser Gly Gly Ser Thr Tyr Tyr Asn Ser Val Leu Lys
    50                  55                  60

Ser Arg Ile Ser Ile Thr Ala Asp Thr Ala Lys Asn Gln Phe Ser Leu
65                  70                  75                  80

Gln Leu Ser Ser Met Thr Thr Glu Asp Thr Ala Val Tyr Tyr Cys Ala
            85                  90                  95

Arg Arg Leu Ser Gly Tyr Asn Tyr Val Pro Phe Ala Tyr Trp Gly Gln
        100                 105                 110

Gly Thr Leu Val Thr Val Ser Ser Ala Ser Thr Thr Ala Pro Ser Val
        115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
            165                 170                 175

Leu Gln Ser Ser Gly Leu Tyr Ser Leu Ser Ser Met Val Thr Val Pro
            180                 185                 190

Ser Ser Arg Trp Pro Ser Glu Thr Phe Thr Cys Asn Val Ala His Pro
        195                 200                 205

Ala Ser Lys Thr Lys Val Asp Lys Pro Val Pro Lys Arg Glu Asn Gly
    210                 215                 220

Arg Val Pro Arg Pro Pro Asp Cys Pro Lys Cys Pro Ala Pro Glu Met
225                 230                 235                 240

Leu Gly Gly Pro Ser Val Phe Ile Phe Pro Pro Lys Pro Lys Asp Thr
            245                 250                 255

Leu Leu Ile Ala Arg Thr Pro Glu Val Thr Cys Val Val Val Ala Leu
            260                 265                 270

Asp Pro Glu Asp Pro Glu Val Gln Ile Ser Trp Phe Val Asp Gly Lys
        275                 280                 285

Gln Met Gln Thr Ala Lys Thr Gln Pro Arg Glu Glu Gln Phe Ala Gly
    290                 295                 300
```

-continued

```
Thr Tyr Arg Val Val Ser Val Leu Pro Ile Gly His Gln Asp Trp Leu
305             310             315             320

Lys Gly Lys Gln Phe Thr Cys Lys Val Asn Asn Lys Ala Leu Pro Ser
                325             330             335

Pro Ile Glu Arg Thr Ile Ser Lys Ala Arg Gly Gln Ala His Gln Pro
            340             345             350

Ser Val Tyr Val Leu Pro Pro Ser Arg Glu Glu Leu Ser Lys Asn Thr
            355             360             365

Val Ser Leu Thr Cys Leu Ile Lys Asp Phe Phe Pro Pro Asp Ile Asp
        370             375             380

Val Glu Trp Gln Ser Asn Gly Gln Gln Glu Pro Glu Ser Lys Tyr Arg
385             390             395             400

Thr Thr Pro Pro Gln Leu Asp Glu Asp Gly Ser Tyr Phe Leu Tyr Ser
            405             410             415

Lys Leu Ser Val Asp Lys Ser Arg Trp Gln Arg Gly Asp Thr Phe Ile
            420             425             430

Cys Ala Val Met His Glu Ala Leu His Asn His Tyr Thr Gln Glu Ser
        435             440             445

Leu Ser His Ser Pro Gly Lys
    450             455
```

```
<210> SEQ ID NO 97
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Glu Ile Val Met Thr Gln Ser Pro Ala Ser Leu Ser Leu Ser Gln Glu
1               5               10              15

Glu Lys Val Thr Ile Thr Cys Lys Ala Ser Gln Asn Ile Tyr Lys His
                20              25              30

Leu Ala Trp Tyr Gln Gln Lys Pro Gly Gln Ala Pro Lys Leu Leu Ile
            35              40              45

Tyr Asn Ala Asn Ser Leu Gln Thr Gly Val Pro Ser Arg Phe Ser Gly
        50              55              60

Ser Gly Ser Gly Thr Asp Phe Ser Phe Thr Ile Ser Ser Leu Glu Pro
65              70              75              80

Glu Asp Val Ala Val Tyr Tyr Cys Gln Gln Tyr Tyr Ser Gly Asp Thr
            85              90              95

Phe Gly Ala Gly Thr Lys Val Glu Leu Lys Arg Asn Asp Ala Gln Pro
            100             105             110

Ala Val Tyr Leu Phe Gln Pro Ser Pro Asp Gln Leu His Thr Gly Ser
            115             120             125

Ala Ser Val Val Cys Leu Leu Asn Ser Phe Tyr Pro Lys Asp Ile Asn
        130             135             140

Val Lys Trp Lys Val Asp Gly Val Ile Gln Asp Thr Gly Ile Gln Glu
145             150             155             160

Ser Val Thr Glu Gln Asp Lys Asp Ser Thr Tyr Ser Leu Ser Ser Thr
            165             170             175

Leu Thr Met Ser Ser Thr Glu Tyr Leu Ser His Glu Leu Tyr Ser Cys
            180             185             190
```

```
Glu Ile Thr His Lys Ser Leu Pro Ser Thr Leu Ile Lys Ser Phe Gln
        195                 200                 205

Arg Ser Glu Cys Gln Arg Val Asp
    210                 215

<210> SEQ ID NO 98
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Glu Ile Val Met Thr Gln Ser Pro Ala Ser Leu Ser Leu Ser Gln Glu
1               5                   10                  15

Glu Lys Val Thr Ile Thr Cys Lys Ala Ser Gln Asn Ile Tyr Lys His
            20                  25                  30

Leu Ala Trp Tyr Gln Gln Lys Pro Gly Gln Ala Pro Lys Leu Leu Ile
        35                  40                  45

Tyr Asn Ala Asn Ser Leu Gln Thr Gly Ile Pro Ser Arg Phe Ser Gly
    50                  55                  60

Ser Gly Ser Gly Thr Asp Phe Ser Phe Thr Ile Ser Ser Leu Glu Pro
65                  70                  75                  80

Glu Asp Val Ala Val Tyr Phe Cys Gln Gln Tyr Tyr Ser Gly Asp Thr
                85                  90                  95

Phe Gly Ala Gly Thr Lys Val Glu Leu Lys Arg Asn Asp Ala Gln Pro
            100                 105                 110

Ala Val Tyr Leu Phe Gln Pro Ser Pro Asp Gln Leu His Thr Gly Ser
        115                 120                 125

Ala Ser Val Val Cys Leu Leu Asn Ser Phe Tyr Pro Lys Asp Ile Asn
    130                 135                 140

Val Lys Trp Lys Val Asp Gly Val Ile Gln Asp Thr Gly Ile Gln Glu
145                 150                 155                 160

Ser Val Thr Glu Gln Asp Lys Asp Ser Thr Tyr Ser Leu Ser Ser Thr
                165                 170                 175

Leu Thr Met Ser Ser Thr Glu Tyr Leu Ser His Glu Leu Tyr Ser Cys
            180                 185                 190

Glu Ile Thr His Lys Ser Leu Pro Ser Thr Leu Ile Lys Ser Phe Gln
        195                 200                 205

Arg Ser Glu Cys Gln Arg Val Asp
    210                 215

<210> SEQ ID NO 99
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Glu Ile Val Met Thr Gln Ser Pro Gly Ser Leu Ala Gly Ser Ala Gly
1               5                   10                  15

Glu Ser Val Ser Ile Asn Cys Lys Ala Ser Gln Asn Ile Tyr Lys His
            20                  25                  30

Leu Ala Trp Tyr Gln Gln Lys Pro Gly Glu Arg Pro Lys Leu Leu Ile
```

```
              35                  40                  45

Tyr Asn Ala Asn Ser Leu Gln Thr Gly Val Pro Ala Arg Phe Ser Ser
    50                  55                  60

Ser Gly Ser Gly Thr Asp Phe Thr Leu Thr Ile Asn Asn Leu Gln Ala
65                  70                  75                  80

Glu Asp Val Gly Asp Tyr Tyr Cys Gln Gln Tyr Tyr Ser Gly Asp Thr
                85                  90                  95

Phe Gly Ala Gly Thr Lys Val Glu Leu Lys Arg Asn Asp Ala Gln Pro
            100                 105                 110

Ala Val Tyr Leu Phe Gln Pro Ser Pro Asp Gln Leu His Thr Gly Ser
            115                 120                 125

Ala Ser Val Val Cys Leu Leu Asn Ser Phe Tyr Pro Lys Asp Ile Asn
    130                 135                 140

Val Lys Trp Lys Val Asp Gly Val Ile Gln Asp Thr Gly Ile Gln Glu
145                 150                 155                 160

Ser Val Thr Glu Gln Asp Lys Asp Ser Thr Tyr Ser Leu Ser Ser Thr
                165                 170                 175

Leu Thr Met Ser Ser Thr Glu Tyr Leu Ser His Glu Leu Tyr Ser Cys
                180                 185                 190

Glu Ile Thr His Lys Ser Leu Pro Ser Thr Leu Ile Lys Ser Phe Gln
            195                 200                 205

Arg Ser Glu Cys Gln Arg Val Asp
    210                 215

<210> SEQ ID NO 100
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Glu Val Gln Leu Val Glu Ser Gly Gly Asp Leu Val Lys Pro Glu Gly
1                   5                   10                  15

Ser Leu Arg Leu Ser Cys Val Val Ser Gly Phe Ser Leu Thr Ser Asn
                20                  25                  30

Gly Val Ser Trp Val Arg Gln Ala Pro Gly Lys Gly Leu Gln Trp Ile
            35                  40                  45

Ala Ala Ile Ser Ser Gly Gly Ser Thr Tyr Tyr Asn Ser Val Leu Lys
    50                  55                  60

Ser Arg Leu Thr Ile Ser Arg Asp Asn Ala Lys Asn Thr Leu Tyr Leu
65                  70                  75                  80

Gln Met Asn Ser Leu Arg Thr Glu Asp Thr Ala Val Tyr Tyr Cys Ala
                85                  90                  95

Arg Arg Leu Ser Gly Tyr Asn Tyr Val Pro Phe Ala Tyr Trp Gly Gln
            100                 105                 110

Gly Thr Leu Val Thr Val Ser Ser Ala Ser Thr Thr Ala Pro Ser Val
            115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175
```

```
Leu Gln Ser Ser Gly Leu Tyr Ser Leu Ser Ser Met Val Thr Val Pro
            180                 185                 190

Ser Ser Arg Trp Pro Ser Glu Thr Phe Thr Cys Asn Val Ala His Pro
            195                 200                 205

Ala Ser Lys Thr Lys Val Asp Lys Pro Val Pro Lys Arg Glu Asn Gly
            210                 215                 220

Arg Val Pro Arg Pro Pro Asp Cys Pro Lys Cys Pro Ala Pro Glu Met
225                 230                 235                 240

Leu Gly Gly Pro Ser Val Phe Ile Phe Pro Pro Lys Pro Lys Asp Thr
                245                 250                 255

Leu Leu Ile Ala Arg Thr Pro Glu Val Thr Cys Val Val Val Ala Leu
            260                 265                 270

Asp Pro Glu Asp Pro Glu Val Gln Ile Ser Trp Phe Val Asp Gly Lys
            275                 280                 285

Gln Met Gln Thr Ala Lys Thr Gln Pro Arg Glu Glu Gln Phe Ala Gly
            290                 295                 300

Thr Tyr Arg Val Val Ser Val Leu Pro Ile Gly His Gln Asp Trp Leu
305                 310                 315                 320

Lys Gly Lys Gln Phe Thr Cys Lys Val Asn Asn Lys Ala Leu Pro Ser
                325                 330                 335

Pro Ile Glu Arg Thr Ile Ser Lys Ala Arg Gly Gln Ala His Gln Pro
                340                 345                 350

Ser Val Tyr Val Leu Pro Pro Ser Arg Glu Glu Leu Ser Lys Asn Thr
                355                 360                 365

Val Ser Leu Thr Cys Leu Ile Lys Asp Phe Phe Pro Pro Asp Ile Asp
            370                 375                 380

Val Glu Trp Gln Ser Asn Gly Gln Gln Glu Pro Glu Ser Lys Tyr Arg
385                 390                 395                 400

Thr Thr Pro Pro Gln Leu Asp Glu Asp Gly Ser Tyr Phe Leu Tyr Ser
                405                 410                 415

Lys Leu Ser Val Asp Lys Ser Arg Trp Gln Arg Gly Asp Thr Phe Ile
                420                 425                 430

Cys Ala Val Met His Glu Ala Leu His Asn His Tyr Thr Gln Glu Ser
                435                 440                 445

Leu Ser His Ser Pro Gly Lys
    450                 455

<210> SEQ ID NO 101
<211> LENGTH: 31
<212> TYPE: PRT
<213> ORGANISM: Canis lupus familiaris

<400> SEQUENCE: 101

Gly Leu Asp Leu Trp Arg Val Leu Lys Pro Ala Met Val Asp Gly Arg
1               5                   10                  15

Arg Pro Val Gln Leu Met Trp Lys Lys Ala Thr Gly Ala Pro Val
            20                  25                  30

<210> SEQ ID NO 102
<211> LENGTH: 26
<212> TYPE: PRT
<213> ORGANISM: Canis lupus familiaris

<400> SEQUENCE: 102

Gly Ile Pro Ser Ala Gly Pro Val Thr Gln Ala Asp Ser Ile Gly Val
1               5                   10                  15
```

-continued

```
Lys Thr Val Thr Ile Thr Trp Lys Glu Ile
            20                  25

<210> SEQ ID NO 103
<211> LENGTH: 48
<212> TYPE: PRT
<213> ORGANISM: Canis lupus familiaris

<400> SEQUENCE: 103

Ser Lys Thr Val Asn Ser Asn Ile Leu Gln Tyr Arg Leu Glu Ser Leu
1               5                   10                  15

Thr Arg Arg Thr Ser Tyr Ser Leu Gln Val Met Ala Ser Thr Asn Ala
            20                  25                  30

Gly Gly Thr Asn Gly Thr Lys Ile Asn Phe Lys Thr Leu Ser Ile Ser
        35                  40                  45

<210> SEQ ID NO 104
<211> LENGTH: 21
<212> TYPE: PRT
<213> ORGANISM: Canis lupus familiaris

<400> SEQUENCE: 104

Ser Tyr Thr Trp Tyr Lys Val Lys Arg Thr Tyr Ser Tyr Gly Tyr Lys
1               5                   10                  15

Ser Asp Ile Cys Ser
            20

<210> SEQ ID NO 105
<211> LENGTH: 51
<212> TYPE: PRT
<213> ORGANISM: Canis lupus familiaris

<400> SEQUENCE: 105

Glu Ala Gln Asn Ala Asp Gly Ile Met Lys Ser Asp Ile Thr Tyr Trp
1               5                   10                  15

Asn Leu Asp Ala Ile Met Lys Ile Glu Pro Pro Glu Ile Phe Ser Val
            20                  25                  30

Lys Ser Val Leu Gly Ile Lys Arg Met Leu Gln Ile Lys Trp Ile Arg
        35                  40                  45

Pro Val Leu
    50
```

CANINIZED ANTIBODIES TO CANINE INTERLEUKIN-31 RECEPTOR *ALPHA*

CROSS-REFERENCE TO RELATED APPLICATIONS

This application is a National Stage application of International Patent Application No. PCT/EP2021/078386, filed Oct. 14, 2022, which claims priority to U.S. Provisional Patent Application Nos. 63/092,294, filed Oct. 15, 2020, 63/092,296, filed Oct. 15, 2020, 63/127,184, filed Dec. 18, 2020, 63/235,258, filed Aug. 20, 2021, and 63/235,257, filed Aug. 20, 2021, the contents of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Oct. 1, 2021, is named 25071-WO-PCT-_SL.txt and is 103,453 bytes in size.

FIELD OF THE INVENTION

The present invention relates to antibodies to canine IL-31 receptor alpha that have a high binding affinity for the canine IL-31 receptor alpha and that can block the binding of canine IL-31 to the canine IL-31 receptor alpha. The present invention also relates to use of the antibodies of the present invention in the treatment of atopic dermatitis in dogs.

BACKGROUND OF THE INVENTION

The immune system comprises a network of resident and recirculating specialized cells that function collaboratively to protect the host against infectious diseases and cancer. The ability of the immune system to perform this function depends to a large extent on the biological activities of a group of proteins secreted by leukocytes and collectively referred to as interleukins. Among the well-studied interleukins are four important molecules identified as interleukin-31 (IL-31), interleukin-4 (IL-4), interleukin-13 (IL-13), and interleukin-22 (IL-22). Although IL-4, IL-13, IL-22, and IL-31, are critical cytokines for the development of immune responses that are required for protection against extracellular pathogens (e.g., tissue or lumen dwelling parasites), these cytokines also have been implicated in the pathogenesis of allergic diseases in humans and animals, including atopic dermatitis.

Atopic dermatitis (AD) is a relapsing pruritic and chronic inflammatory skin disease, that is characterized by immune system dysregulation and epidermal barrier abnormalities in humans. The pathological and immunological attributes of atopic dermatitis have been the subject of extensive investigations [reviewed in Rahman et al. Inflammation & Allergy-drug target 10:486-496 (2011) and Harskamp et al., Seminar in Cutaneous Medicine and Surgery 32:132-139 (2013)]. Atopic dermatitis is also a common condition in companion animals, especially dogs, where its prevalence has been estimated to be approximately 10-15% of the canine population. The pathogenesis of atopic dermatitis in dogs and cats [reviewed in Nuttall et al., Veterinary Records 172(8):201-207 (2013)] shows significant similarities to that of atopic dermatitis in man including skin infiltration by a variety of immune cells and CD4+ Th2 polarized cytokine milieu including the preponderance of IL-31, IL-4, and IL-13. In addition, IL-22 has been implicated in the exaggerated epithelial proliferation leading to epidermal hyperplasia that is characteristic of atopic dermatitis.

For example, antibodies against canine IL-31 have been shown to have an effect on pruritus associated with atopic dermatitis in dogs [U.S. Pat. No. 8,790,651 B2; U.S. Pat. No. 10,093,731 B2]. In addition, an antibody against human IL-31 receptor alpha (IL-31RA) has been tested and found to have an effect on pruritus associated with atopic dermatitis in humans [Ruzicka, et al., New England Journal of Medicine, 376(9),826-835 (2017)].

IL-4 and IL-13 are closely related proteins that can be secreted by many cell types including CD4 +Th2 cells, natural killer T cells (NKT), macrophages, mast cells, and basophils. IL-4 and IL-13 display many overlapping functions and are critical to the development of T cell-dependent humoral immune responses. It is known that IL-4 binds with high affinity to two receptors i.e., type-I and type-II IL-4 receptors. Monoclonal antibodies raised against human IL-4 receptor alpha (IL-4 $R_\alpha$) have been developed and some of these antibodies have been extensively tested for their therapeutic effects for treating atopic dermatitis in humans [see, e.g., US2015/0017176 A1]. More recently, caninized antibodies to canine IL-4 $R_\alpha$ that block the binding of canine IL-4 to canine IL-4 $R_\alpha$ also have been disclosed [US2018/0346580A1, hereby incorporated by reference in its entirety]. Because the Type II IL-4 receptor consists of the IL-4 receptor a chain and the IL-13 receptor al chain, antibodies to canine IL-4 $R_\alpha$ have been obtained that can block both canine IL-4 and canine IL-13 from binding the Type II canine IL-4 receptor, thereby serving to help block the inflammation associated with atopic dermatitis [US2018/0346580A1].

Interleukin-22 (IL-22), also known as IL-10-related T cell-derived inducible factor (IL-TIF), belongs to the IL-10 cytokine family. IL-22 is produced by normal T cells upon anti-CD3 stimulation in humans. Mouse IL-22 expression is also induced in various organs upon lipopolysaccharide injection, suggesting that IL-22 may be involved in inflammatory responses. IL-22 binds specifically to, and signals through, a receptor complex consisting of a heterodimeric complex of IL-10R2 (also known as IL-10R beta) and the Interleukin-22 receptor (IL-22R) [see, Lee et al., Pharmacology Research & Perspectives, Pages 1-13 (2018: e00434)]. The Interleukin-22 receptor is also known as Interleukin-22R, alpha 11, IL-22RA1; IL-22R1; zcytor11, and CRF2-9 [Xu et al., Proc. Nat. Acad. Set. 98 (17) 9511-9516 (2001); Gelebart and Lai, Atlas of Genetics and cytogenetics 14(12).1106-1110 (2010)] IL-22 induces epithelial cell proliferation during wound healing, and its deficiency can enable uncontrolled proliferation and enhance tumor development [Huber et al., Nature 491:259-263 (2012] IL-22 has been shown to activate STAT-1 and STAT-3 in several hepatoma cell lines and upregulate the production of acute phase proteins. Antibodies to Interleukin-22 and IL-22R act as anti-proliferative agents by blocking the interaction of IL-22 with IL-22R and thereby the related signaling pathway that leads to the epithelial proliferation.

Pharmaceuticals that have either proven to aid in the treatment of atopic dermatitis and/or have shown promise to do so include: Janus kinase (JAK) inhibitors [see e.g., U.S. Pat. No. 8,133,899; U.S. 8,987,283; WO 2018/108969], spleen tyrosine kinase (SYK) inhibitors [see e.g., U.S. Pat. No. 8,759,366], and antagonists to a chemoattractant receptor-homologous molecule expressed on TH2 cells [see e.g., U.S. Pat. Nos. 7,696,222, 8,546,422, 8,637,541, and 8,546, 422].

However, despite some success in treating atopic dermatitis, there remains a need to design alternative and/or better therapies that can address one or more of the symptoms of canine atopic dermatitis.

The citation of any reference herein should not be construed as an admission that such reference is available as "prior art" to the instant application.

SUMMARY OF THE INVENTION

The present invention provides new mammalian antibodies, including caninized antibodies, to IL-31 receptor alpha (IL-31RA) from canines. In certain embodiments, the mammalian antibodies to canine IL-31 receptor alpha (cIL-31RA) are isolated antibodies. In preferred embodiments, the mammalian antibodies or antigen binding fragments thereof bind canine IL-31RA. In more particular embodiments, the mammalian antibodies or antigen binding fragments also block the binding of canine IL-31RA to canine interleukin-31. In particular embodiments, the antibodies are rat antibodies to canine IL-31RA. In more particular embodiments, the mammalian antibodies are caninized rat antibodies to canine IL-31RA.

Accordingly, the present invention provides mammalian antibodies or antigen binding fragments thereof that bind canine IL-31RA and that comprise a heavy chain that comprises a set of three heavy chain complementary determining regions (CDRs), a CDR heavy 1 (HCDR1), a CDR heavy 2 (HCDR2), and a CDR heavy 3 (HCDR3) and a set of three light chain CDRs: CDR light 1 (LCDR1), CDR light 2 (LCDR2), and CDR light 3 (LCDR3).

In certain embodiments, the mammalian antibody or antigen binding fragment comprises an HCDR1 that comprises the amino acid sequence of SEQ ID NO: 13, an HCDR2 that comprises the amino acid sequence of SEQ ID NO: 14, and an HCDR3 that comprises the amino acid sequence of SEQ ID NO: 15; and further comprises a LCDR1 that comprises the amino acid sequence of SEQ ID NO: 16, a LCDR2 that comprises the amino acid sequence of SEQ ID NO: 17, and a LCDR3 that comprises the amino acid sequence of SEQ ID NO: 18. In specific embodiments, when bound to canine IL-31RA, the antibody binds to an epitope comprised by the amino acid of SEQ ID NO: 102, or SEQID NO: 103, or to both SEQ ID NO: 102 and SEQID NO: 103. In related embodiments, when bound to canine IL-31RA, the antibody binds at least one amino acid residue, preferably one to three amino acid residues, more preferably two to five amino acid residues, and/or more preferably three to eight amino acid residues or more within the amino acid sequence of SEQ ID NO: 102 or SEQ ID NO: 103, or both SEQ ID NO: 102 and SEQ ID NO: 103.

In other embodiments, the mammalian antibody or antigen binding fragment comprises an HCDR1 that comprises the amino acid sequence of SEQ ID NO: 19, an HCDR2 that comprises the amino acid sequence of SEQ ID NO: 20, and an HCDR3 that comprises the amino acid sequence of SEQ ID NO: 21; and further comprises a LCDR1 that comprises the amino acid sequence of SEQ ID NO: 22, a LCDR2 that comprises the amino acid sequence of SEQ ID NO: 23, and a LCDR3 that comprises the amino acid sequence of SEQ ID NO: 24.

In still other embodiments, the mammalian antibody or antigen binding fragment comprises an HCDR1 that comprises the amino acid sequence of SEQ ID NO: 25, an HCDR2 that comprises the amino acid sequence of SEQ ID NO: 26, and an HCDR3 that comprises the amino acid sequence of SEQ ID NO: 27; and further comprises a LCDR1 that comprises the amino acid sequence of SEQ ID NO: 28, a LCDR2 that comprises the amino acid sequence of SEQ ID NO: 29, and a LCDR3 that comprises the amino acid sequence of SEQ ID NO: 30. In specific embodiments, when bound to canine IL-31RA the antibody binds to an epitope comprised by the amino acid sequence of SEQ ID NO: 101. In related embodiments, when bound to canine IL-31RA the antibody binds at least one amino acid residue, preferably one to three amino acid residues, more preferably two to five amino acid residues, and/or more preferably three to eight amino acid residues or more within the amino acid sequence of SEQ ID NO: 101.

In specific embodiments, the mammalian antibody to canine IL-31RA is a rat antibody. In particular embodiments, the mammalian antibody to canine IL-31RA is a caninized rat antibody. In certain embodiments, the caninized antibody comprises a heavy chain that comprises an IgG-D cFc, but the naturally occurring IgG-D hinge region is replaced by a hinge region comprising the amino acid sequence of SEQ ID NO: 79. In other embodiments, the caninized antibody comprises a heavy chain that comprises an IgG-D cFc, but the naturally occurring IgG-D hinge region is replaced by a hinge region comprising the amino acid sequence of SEQ ID NO: 80. In still other embodiments, the caninized antibody comprises a heavy chain that comprises an IgG-D cFc, but the naturally occurring IgG-D hinge region is replaced by a hinge region comprising the amino acid sequence of SEQ ID NO: 81. In yet other embodiments, the caninized antibody comprises a heavy chain that comprises an IgG-D cFc, but the naturally occurring IgG-D hinge region is replaced by a hinge region comprising the amino acid sequence of SEQ ID NO: 82.

In certain embodiments, the caninized antibody comprises a heavy chain comprising a modified canine IgG-B (IgG-Bm) that comprises the amino acid sequence of SEQ ID NO: 78. In alternative embodiments, the caninized antibody comprises a heavy chain comprising a non-modified canine IgG-B that comprises the amino acid sequence of SEQ ID NO: 77.

In certain embodiments of the compositions, the caninized antibody against canine IL-31RA (cIL-31RA) comprises a heavy chain comprising the amino acid sequence of SEQ ID NO: 88 or SEQ ID NO: 89 and a light chain comprising the amino acid sequence of SEQ ID NO: 90, SEQ ID NO: 91, SEQ ID NO: 92, or SEQ ID NO: 93. In specific embodiments, when bound to canine IL-31RA the antibody binds to an epitope comprised by the amino acid sequence of SEQ ID NO: 101. In related embodiments, when bound to canine IL-31RA the antibody binds at least one amino acid residue, preferably one to three amino acid residues, more preferably two to five amino acid residues, and/or more preferably three to eight amino acid residues or more within the amino acid sequence of SEQ ID NO: 101. The present invention further provides antigen binding fragments of these caninized antibodies.

In particular embodiments, the caninized antibody comprises a light chain comprising the amino acid sequence of SEQ ID NO: 90 and a heavy chain comprising the amino acid sequence of SEQ ID NO: 88. In other embodiments, the caninized antibody comprises a light chain comprising the amino acid sequence of SEQ ID NO: 91 and a heavy chain comprising the amino acid sequence of SEQ ID NO: 88. In still other embodiments, the caninized antibody comprises a light chain comprising the amino acid sequence of SEQ ID NO: 92 and a heavy chain comprising the amino acid sequence of SEQ ID NO: 88. In yet other embodiments, the caninized antibody comprises a light chain comprising the amino acid sequence of SEQ ID NO: 93 and a heavy chain comprising the amino acid sequence of SEQ ID NO: 88. In other embodiments, the caninized antibody comprises a light chain comprising the amino acid sequence of SEQ ID NO: 90 and a heavy chain comprising the amino acid sequence of SEQ ID NO: 89. In yet other embodiments, the caninized antibody comprises a light chain comprising the amino acid sequence of SEQ ID NO: 91 and a heavy chain comprising the amino acid sequence of SEQ ID NO: 89. In still other embodiments, the caninized antibody comprises a light chain comprising the amino acid sequence of SEQ ID NO: 92 and a heavy chain comprising the amino acid sequence of SEQ ID NO: 89. In yet other embodiments, the caninized antibody comprises a light chain comprising the amino acid sequence of SEQ ID NO: 93 and a heavy chain comprising the amino acid sequence of SEQ ID NO: 89. In specific embodiments when bound to canine IL-31RA the antibody binds to at least one amino acid residue, preferably one to three amino acid residues, more preferably two to five amino acid residues, and/or even more preferably three to eight amino acid residues or more within the amino acid sequence of SEQ ID NO: 101.

In certain embodiments of the compositions, the caninized antibody against cIL-31RA comprises a heavy chain comprising the amino acid sequence of SEQ ID NO: 94, SEQ ID NO: 95, SEQ ID NO: 96, or SEQ ID NO: 100, and a light chain comprising the amino acid sequence of SEQ ID NO: 97, SEQ ID NO: 98, or SEQ ID NO: 99. In specific embodiments, when bound to canine IL-31RA, the antibody binds to an epitope comprised by the amino acid of SEQ ID NO: 102, or SEQID NO: 103, or to both SEQ ID NO: 102 and SEQID NO: 103. In related embodiments, when bound to canine IL-31RA, the antibody binds at least one amino acid residue, preferably one to three amino acid residues, more preferably two to five amino acid residues, and/or more preferably three to eight amino acid residues or more within the amino acid sequence of SEQ ID NO: 102 or SEQ ID NO: 103, or both SEQ ID NO: 102 and SEQ ID NO: 103.

The present invention further provides antigen binding fragments of these caninized antibodies.

In other embodiments, the caninized antibody comprises a light chain comprising the amino acid sequence of SEQ ID NO: 97 and a heavy chain comprising the amino acid sequence of SEQ ID NO: 94. In yet other embodiments, the caninized antibody comprises a light chain comprising the amino acid sequence of SEQ ID NO: 97 and a heavy chain comprising the amino acid sequence of SEQ ID NO: 95. In still other embodiments, the caninized antibody comprises a light chain comprising the amino acid sequence of SEQ ID NO: 97 and a heavy chain comprising the amino acid sequence of SEQ ID NO: 96. In yet other embodiments, the caninized antibody comprises a light chain comprising the amino acid sequence of SEQ ID NO: 97 and a heavy chain comprising the amino acid sequence of SEQ ID NO: 100. In specific embodiments, when bound to canine IL-31RA, the antibody binds to an epitope comprised by the amino acid of SEQ ID NO: 102, or SEQID NO: 103, or to both SEQ ID NO: 102 and SEQID NO: 103. In related embodiments, when bound to canine IL-31RA, the antibody binds at least one amino acid residue, preferably one to three amino acid residues, more preferably two to five amino acid residues, and/or more preferably three to eight amino acid residues or more within the amino acid sequence of SEQ ID NO: 102 or SEQ ID NO: 103, or both SEQ ID NO: 102 and SEQ ID NO: 103.

In still other embodiments, the caninized antibody comprises a light chain comprising the amino acid sequence of SEQ ID NO: 98 and a heavy chain comprising the amino acid sequence of SEQ ID NO: 94. In yet other embodiments, the caninized antibody comprises a light chain comprising the amino acid sequence of SEQ ID NO: 98 and a heavy chain comprising the amino acid sequence of SEQ ID NO: 95. In still other embodiments, the caninized antibody comprises a light chain comprising the amino acid sequence of SEQ ID NO: 98 and a heavy chain comprising the amino acid sequence of SEQ ID NO: 96. In yet other embodiments, the caninized antibody comprises a light chain comprising the amino acid sequence of SEQ ID NO: 98 and a heavy chain comprising the amino acid sequence of SEQ ID NO: 100. In specific embodiments, when bound to canine IL-31RA, the antibody binds to an epitope comprised by the amino acid of SEQ ID NO: 102, or SEQID NO: 103, or to both SEQ ID NO: 102 and SEQID NO: 103. In related embodiments, when bound to canine IL-31RA, the antibody binds at least one amino acid residue, preferably one to three amino acid residues, more preferably two to five amino acid residues, and/or more preferably three to eight amino acid residues or more within the amino acid sequence of SEQ ID NO: 102 or SEQ ID NO: 103, or both SEQ ID NO: 102 and SEQ ID NO: 103.

In still other embodiments, the caninized antibody comprises a light chain comprising the amino acid sequence of SEQ ID NO: 99 and a heavy chain comprising the amino acid sequence of SEQ ID NO: 94. In yet other embodiments, the caninized antibody comprises a light chain comprising the amino acid sequence of SEQ ID NO: 99 and a heavy chain comprising the amino acid sequence of SEQ ID NO: 95. In still other embodiments, the caninized antibody comprises a light chain comprising the amino acid sequence of SEQ ID NO: 99 and a heavy chain comprising the amino acid sequence of SEQ ID NO: 96. In yet other embodiments, the caninized antibody comprises a light chain comprising the amino acid sequence of SEQ ID NO: 99 and a heavy chain comprising the amino acid sequence of SEQ ID NO: 100. In specific embodiments when bound to canine IL-31RA the antibody binds to at least one amino acid residue, preferably two to five amino acid residues, and/or more preferably three to eight amino acid residues or more within the amino acid sequence of SEQ ID NO: 102 or SEQ ID NO: 103, or both SEQ ID NO: 102 and SEQ ID NO: 103.

The present invention further provides antigen binding fragments of all of these caninized antibodies.

The present invention further provides isolated mammalian antibodies or antigen binding fragments thereof (including caninized antibodies, canine antibodies, or antigen binding fragments thereof) that bind to canine interleukin-31 receptor alpha (canine IL-31RA) and that when bound to canine IL-31RA the antibody binds to an epitope comprised by the amino acid sequence of SEQ ID NO: 101, or SEQ ID NO: 102, or SEQ ID NO: 103, or SEQ ID NO: 104, or SEQ ID NO: 105, or any combination thereof, in which the antibody binds to canine IL-31RA and blocks the binding of canine IL-31RA to canine IL-31.

In certain embodiments the isolated mammalian antibodies or antigen binding fragments thereof (including caninized antibodies, canine antibodies, or antigen binding fragments thereof) bind canine IL-31RA with specificity, and when bound to canine IL-31RA, the antibody binds to at least one amino acid residue, preferably one to three amino acid residues, more preferably two to five amino acid residues, and/or even more preferably three to eight amino acid residues or more amino acid residues within the amino acid sequence of SEQ ID NO: 101, or SEQ ID NO: 102, or SEQ ID NO: 103, or SEQ ID NO: 104, or SEQ ID NO: 105, or any combination thereof. In particular embodiments, the antibody or antigen binding fragment thereof binds canine IL-31RA and blocks the binding of canine IL-31RA to canine IL-31.

The present invention also provides nucleic acids, including isolated nucleic acids, that encode the CDRs, the heavy chains of the caninized antibodies or antigen binding fragments thereof, and/or the light chains of the caninized antibodies or antigen binding fragments thereof.

Accordingly, the present invention further provides a nucleic acid that encodes a set of the three heavy chain complementary determining regions (CDRs), a CDR heavy 1 (HCDR1), a CDR heavy 2 (HCDR2), and a CDR heavy 3 (HCDR3) of a mammalian antibody or an antigen binding fragment thereof of the present invention. In preferred embodiments a nucleic acid encodes a set of the three heavy chain complementary determining regions (CDRs), a CDR heavy 1 (HCDR1), a CDR heavy 2 (HCDR2), and a CDR heavy 3 (HCDR3) of a caninized antibody or an antigen binding fragment thereof of the present invention.

In certain embodiments of this type, the nucleic acid encodes an HCDR1 that comprises the amino acid sequence of SEQ ID NO: 13, an HCDR2 that comprises the amino acid sequence of SEQ ID NO: 14, and an HCDR3 that comprises the amino acid sequence of SEQ ID NO: 15. In another embodiment of this type, the nucleic acid encodes an HCDR1 that comprises the amino acid sequence of SEQ ID NO: 19, an HCDR2 that comprises the amino acid sequence of SEQ ID NO: 20, and an HCDR3 that comprises the amino acid sequence of SEQ ID NO: 21. In still another embodiment of this type, the nucleic acid encodes an HCDR1 that comprises the amino acid sequence of SEQ ID NO: 25, an HCDR2 that comprises the amino acid sequence of SEQ ID NO: 26, and an HCDR3 that comprises the amino acid sequence of SEQ ID NO: 27.

The present invention also provides a nucleic acid that encodes a set of the three light chain complementary determining regions (CDRs), a CDR light 1 (LCDR1), a CDR light 2 (LCDR2), and a CDR light 3 (LCDR3) of a mammalian antibody or an antigen binding fragment thereof of the present invention. In a more specific embodiment of this type, the nucleic acid encodes an LCDR1 comprises a LCDR1 that comprises the amino acid sequence of SEQ ID NO: 16, a LCDR2 that comprises the amino acid sequence of SEQ ID NO: 17, and a LCDR3 that comprises the amino acid sequence of SEQ ID NO: 18. In a another embodiment of this type, the nucleic acid encodes an LCDR1 comprises a LCDR1 that comprises the amino acid sequence of SEQ ID NO: 22, a LCDR2 that comprises the amino acid sequence of SEQ ID NO: 23, and a LCDR3 that comprises the amino acid sequence of SEQ ID NO: 24. In yet another embodiment of this type, the nucleic acid encodes an LCDR1 comprises a LCDR1 that comprises the amino acid sequence of SEQ ID NO: 28, a LCDR2 that comprises the amino acid sequence of SEQ ID NO: 29, and a LCDR3 that comprises the amino acid sequence of SEQ ID NO: 30.

The present invention further provides a nucleic acid that encodes the heavy chain of a mammalian antibody or an antigen binding fragment thereof of the present invention. The present invention also provides a nucleic acid that encodes the light chain of a mammalian antibody or an antigen binding fragment thereof of the present invention. In addition, the present invention provides expression vectors that comprise one or more of the nucleic acids of the present invention, and host cells that comprise such expression vectors.

The present invention also provides pharmaceutical compositions that comprise the caninized antibodies and antigen binding fragments thereof of the present invention along with a pharmaceutically acceptable carrier and/or diluent. The present invention further provides methods of treating atopic dermatitis comprising administering one of the aforesaid compositions to a canine that has atopic dermatitis. In particular embodiments, the present invention provides methods of aiding in blocking of the pruritus associated with atopic dermatitis, comprising administering to a canine in need thereof a therapeutically effective amount of a pharmaceutical composition of the present invention.

These and other aspects of the present invention will be better appreciated by reference to the following Brief Description of the Drawings and the Detailed Description.

BRIEF DESCRIPTION OF THE DRAWINGS

FIG. 2A: 4G7 (•), 20B8 (⊙), 22B4 (▲), 27A10 (▼), and the Rat IgG2a/Kappa (♦) control. FIG. 2B: 38B6 (•), 48B1 (⊙), 49D3 (▲), and the Rat IgG2a/Kappa (♦) control. FIG. 2C: 10A12 (⊙), 44E2 (▼) and the Rat IgG2a/Kappa (♦) control. FIG. 2D: 47F3 (•), 51G4 (⊙), and the Rat IgG2a/Kappa (▼) control. FIG. 2E: 7D7(•), 28F12 (⊙), 53B3 (▲), and the Rat IgG2a/Kappa (✻) and Rat IgG2b/Kappa (♦) controls.

FIG. 3 shows the antibodies: 4G7(•), 28F12 (▲), 44E2(▼), 48B1 (⊙); and the Rat IgG2a/Kappa (Δ) and Rat IgG2b/Kappa (▽) controls.

9

Figure 6A:
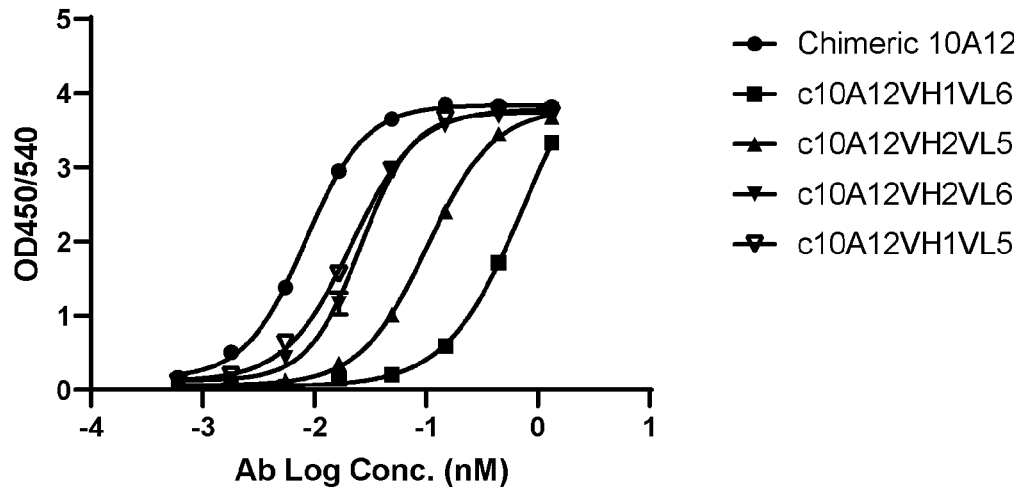
Figure 6B:
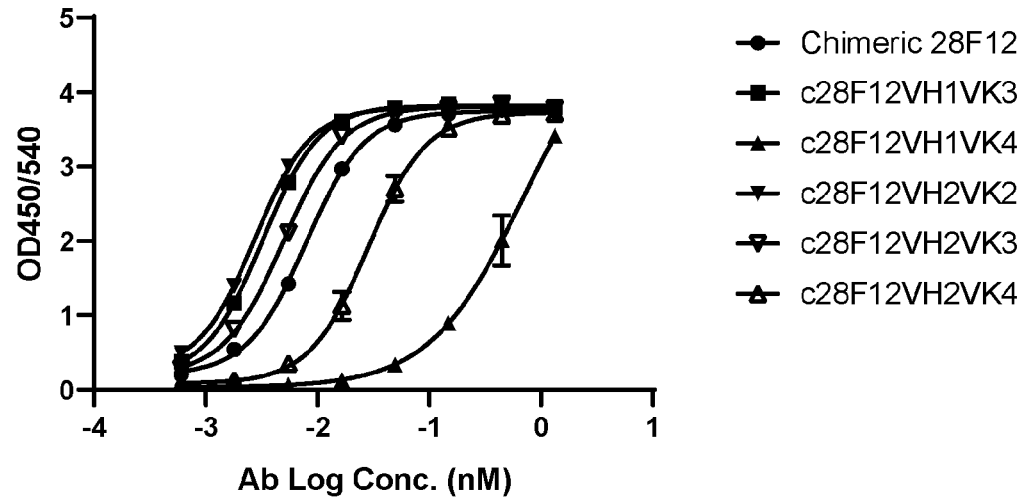
Figure 6C:
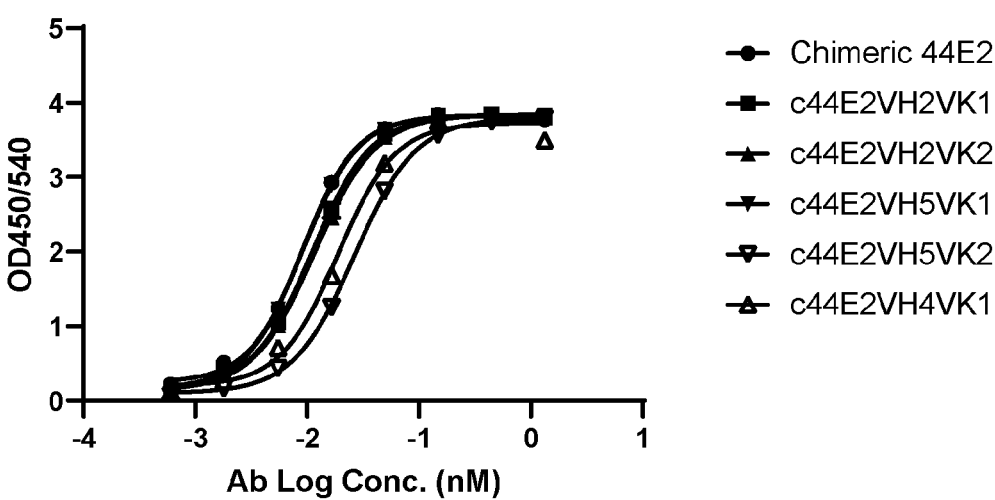

FIGS. 6A-6C show the binding of caninized anti-canine IL-31RA antibodies containing either lambda (L) or kappa (k) light chains as evaluated by ELISA.

FIG. 6A depicts the binding of caninized anti-canine IL-31RA antibodies (cA12) containing lambda (L) light chains as evaluated by ELISA. Chimeric rat/caninized: chimeric 10A12 [•], caninized 10A12VH1VL5 [∇], caninized 10A12VH1VL6 [◉], caninized 10A12VH2VL5[▲], and caninized 10A12VH2VL6 [▼].

FIG. 6B depicts the binding of caninized anti-canine IL-31RA antibodies (28F12) containing kappa (k) light chains as evaluated by ELISA. Chimeric rat/caninized: chimeric 28F12 [•], caninized 28F12VH1VK3 [◉], caninized 28F12VH1VK4 [▲], caninized 28F12VH2VK2 [▼], caninized 28F12VH2VK3[∇], and caninized 28F12VH2VK4 [∆].

FIG. 6C depicts the binding of caninized anti-canine IL-31RA antibodies (44E2) containing kappa (k) light chains as evaluated by ELISA. Chimeric rat/caninized: chimeric 44E2 [•], caninized 44E2VH2VK1[◉], caninized 44E2VH2VK2 [▲], caninized 44E2VH5VK1[▼], caninized 44E2VH5VK2 [∇], and caninized 44E2VH4VK1[∆]. The results show that caninized anti-canine IL-31RA antibodies bind to canine IL-31RA.

Figure 7A:
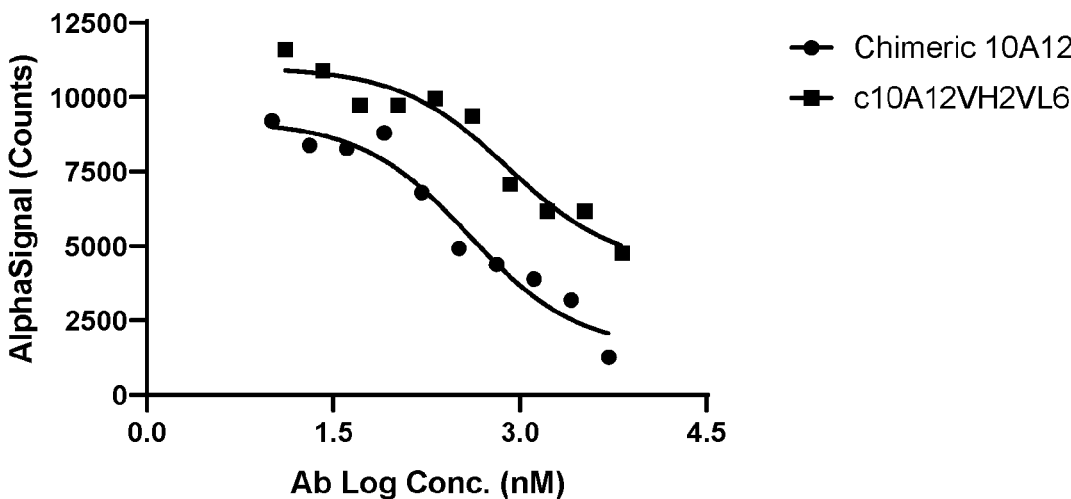
Figure 7B:
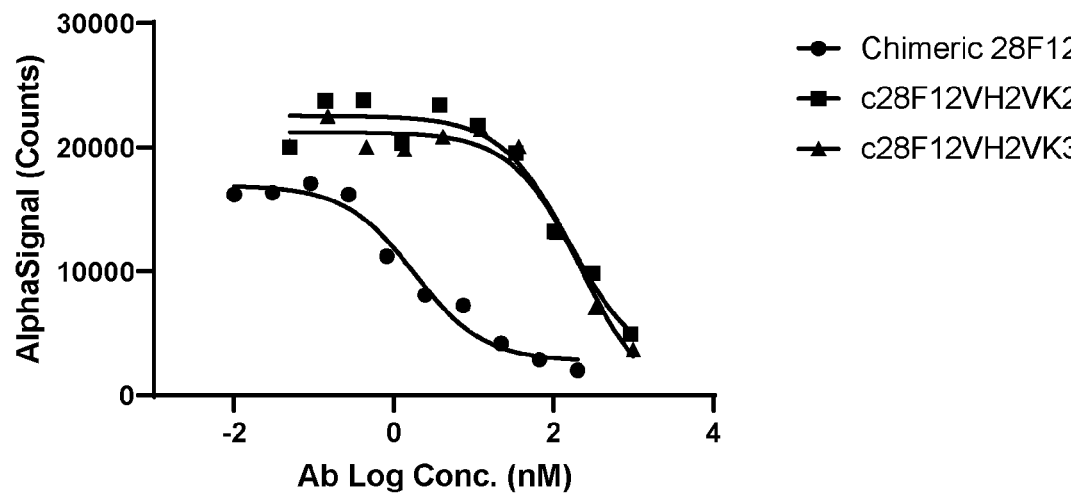
Figure 7C:
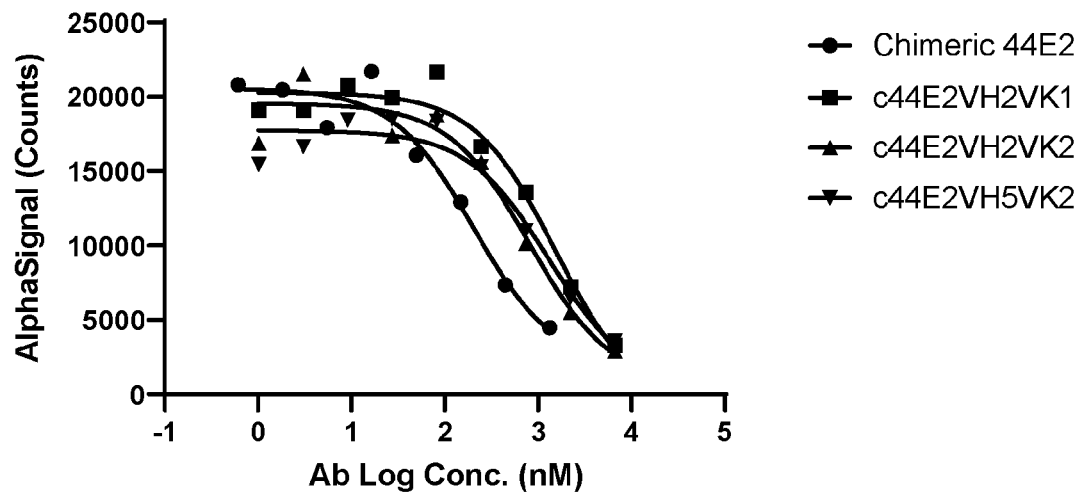

FIG. 7A-7C are graphs showing the inhibition of cIL-31-mediated STAT-3 phosphorylation by cIL-31RA antibodies. Three different caninized monoclonal anti-canine IL-31RA antibodies designated caninized 10A12, caninized c28F12, and caninized 44E2 were evaluated for their ability to inhibit STAT-3 phosphorylation.

FIG. 7A depicts the inhibition of cIL-31-mediated STAT-3 phosphorylation by cIL-31RA antibodies (c10A12). Chimeric rat/caninized: chimeric 10A12 [•] and caninized 10A12VH2VL6 [◉].

FIG. 7B depicts the inhibition of cIL-31-mediated STAT-3 phosphorylation by cIL-31RA antibodies (c28F12). Chimeric rat/caninized: chimeric 28F12 [•], caninized 28F12VH2K2[◉] and caninized 28F12VH2VK3 [▲].

FIG. 7C depicts the inhibition of cIL-31-mediated STAT-3 phosphorylation by cIL-31RA antibodies (c44E2). Chimeric rat/caninized: chimeric c44E2 [•], caninized 44E2VH2VK1[◉], caninized 44E2VH2VK2 [▲], and caninized 44E2VH5VK2 [▼]. The data show that all three antibodies result in a dose dependent inhibition of STAT-3 phosphorylation in the presence of IL-31.

Figure 8A:
Figure 8B:
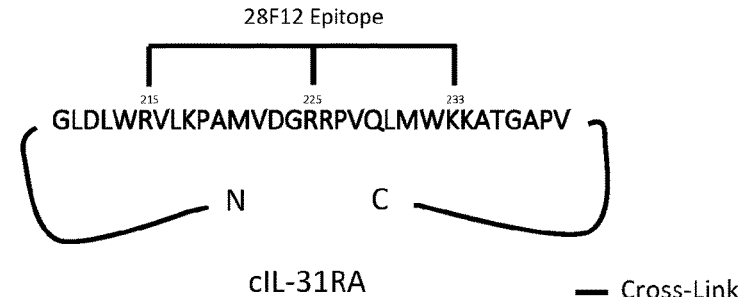
Figure 8C:

FIGS. 8A-8C show the epitopes on canine IL-31RA for the antibodies 10A12, 28F12 and 44E2, respectively. FIG. 8A depicts the amino acid sequences of SEQ ID NO: 104 and SEQ ID NO: 105 respectively. FIG. 8B depicts the amino acid sequence of SEQ ID NO: 101. FIG. 8C depicts the amino acid sequences of SEQ ID NO: 102 and SEQ ID NO: 103, respectively.

DETAILED DESCRIPTION OF THE INVENTION

In response to need for better therapies for atopic dermatitis, the present invention provides formulations and methodology that can achieve a significant effect on the skin inflammation associated with atopic dermatitis.

Abbreviations

Throughout the detailed description and examples of the invention the following abbreviations will be used:

10

ADCC Antibody-dependent cellular cytotoxicity
CDC Complement-dependent cyotoxicity
CDR Complementarity determining region in the immunoglobulin variable regions, defined using the Kabat numbering system
EC50 concentration resulting in 50% efficacy or binding
ELISA Enzyme-linked immunosorbant assay
FR Antibody framework region: the immunoglobulin variable regions excluding the CDR regions.
IC50 concentration resulting in 50% inhibition
IgG Immunoglobulin G
Kabat An immunoglobulin alignment and numbering system pioneered by Elvin A. Kabat [Sequences of Proteins of Immunological Interest, 5th Ed. Public Health Service, National Institutes of Health, Bethesda, Md. (1991)]
mAb Monoclonal antibody (also Mab or MAb)
V region The segment of IgG chains which is variable in sequence between different antibodies.
VH Immunoglobulin heavy chain variable region
VL Immunoglobulin lambda light chain variable region
VK Immunoglobulin kappa light chain variable region

Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Administration" and "treatment", as it applies to an animal, e.g., a canine subject, cell, tissue, organ, or biological fluid, refers to contact of an exogenous pharmaceutical, therapeutic, diagnostic agent, or composition to the animal e.g., a canine subject, cell, tissue, organ, or biological fluid. Treatment of a cell encompasses contact of a reagent to the cell, as well as contact of a reagent to a fluid, where the fluid is in contact with the cell.

"Administration" and "treatment" also mean in vitro and ex vivo treatments, e.g., of a cell, by a reagent, diagnostic, binding compound, or by another cell. The term "subject" includes any organism, preferably an animal, more preferably a mammal (e.g., canine, feline, or human) and most preferably a canine.

"Treat" or "treating" means to administer a therapeutic agent, such as a composition containing any of the antibodies of the present invention, internally or externally to e.g., a canine subject or patient having one or more symptoms, or being suspected of having a condition, for which the agent has therapeutic activity. Typically, the agent is administered in an amount effective to alleviate and/or ameliorate one or more disease/condition symptoms in the treated subject or population, whether by inducing the regression of or inhibiting the progression of such symptom(s) by any clinically measurable degree. The amount of a therapeutic agent that is effective to alleviate any particular disease/condition symptom (also referred to as the "therapeutically effective amount") may vary according to factors such as the disease/condition state, age, and weight of the patient (e.g., canine), and the ability of the pharmaceutical composition to elicit a desired response in the subject. Whether a disease/condition symptom has been alleviated or ameliorated can be assessed by any clinical measurement typically used by veterinarians or other skilled healthcare providers to assess the severity or progression status of that symptom. While an embodiment of the present invention (e.g., a treatment method or article of manufacture) may not be effective in alleviating the target disease/condition symptom(s) in every subject, it should alleviate the target disease/condition symptom(s) in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

"Treatment," as it applies to a human, veterinary (e.g., canine), or research subject, refers to therapeutic treatment, as well as research and diagnostic applications. "Treatment" as it applies to a human, veterinary (e.g., canine), or research subject, or cell, tissue, or organ, encompasses contact of the As used herein the canine Fc (cFc) "IgG-Bm" is canine IgG-B Fc comprising two (2) amino acid residue substitutions, D31A and N63A, as in the amino acid sequence of SEQ ID NO: 78 of IgG-B (see below) and without the c-terminal lysine ('K"). Both the aspartic acid residue (D) at position 31 of SEQ ID NO: 77 and the asparagine residue (N) at position 63 of SEQ ID NO: 77, are substituted by an alanine residue (A) in IgG-Bm. These two amino acid residue substitutions serve to significantly diminish the antibody-dependent cytotoxicity (ADCC) and complement-dependent cytotoxicity (CDC) of the naturally occurring canine IgG-B [see, U.S. Pat. No. 10,106,607 B2, the contents of which are hereby incorporated by reference in their entirety]. Further amino acid substitutions to the IgG-Bm are also envisioned, which parallel those which can be made in IgG-B and may include amino acid substitutions to favor heterodimer formation in bispecific antibodies.

The amino acid sequence of IgG-B, SEQ ID NO: 77 is:

```
1                                                  50
LGGPSVFIFP PKPKDTLLIA RTPEVTCVVV DLDPEDPEVQ ISWFVDGKQM
 └CH2

51                                                 100
QTAKTQPREE QFNGTYRVVS VLPIGHQDWL KGKQFTCKVN NKALPSPIER 101                                                150
TISKARGQAH QPSVYVLPPS REELSKNTVS LTCLIKDFFP PDIDVEWQSN
      └CH3

151                                                200
GQQEPESKYR TTPPQLDEDG SYFLYSKLSV DKSRWQRGDT FICAVMHEAL 201          215
HNHYTQKSLS HSPGK
``` antibodies of the present invention to e.g., a canine or other animal subject, a cell, tissue, physiological compartment, or physiological fluid.

As used herein, the term "canine" includes all domestic dogs, *Canis lupus familiaris* or *Canis familiaris*, unless otherwise indicated.

As used herein, the term "feline" refers to any member of the Felidae family. Members of this family include wild, zoo, and domestic members, including domestic cats, pure-bred and/or mongrel companion cats, show cats, laboratory cats, cloned cats, and wild or feral cats.

As used herein the term "canine frame" refers to the amino acid sequence of the heavy chain and light chain of a canine antibody other than the hypervariable region residues defined herein as CDR residues. With regard to a caninized antibody, in the majority of embodiments the amino acid sequences of the native canine CDRs are replaced with the corresponding foreign CDRs (e.g., those from a mouse or rat antibody) in both chains. Optionally the heavy and/or light chains of the canine antibody may contain some foreign non-CDR residues, e.g., so as to preserve the conformation of the foreign CDRs within the canine antibody, and/or to modify the Fc function, as exemplified below and/or disclosed in U.S. Pat. No. 10,106,607 B2, hereby incorporated by reference herein in its entirety.

The "Fragment crystallizable region" abbreviated as "Fc" corresponds to the CH3-CH2 portion of an antibody that interacts with cell surface receptors called Fc receptors. The canine fragment crystallizable region (cFc) of each of the four canine IgGs were first described by Tang et al. [Vet. Immunol. Immunopathol. 80: 259-270 (2001); see also, Bergeron et al., Vet. Immunol. Immunopathol. 157: 31-41 (2014) and U.S. Pat. No. 10,106,607 B2].

The amino acid sequence of IgG-Bm, SEQ ID NO: 78, is provided below.

```
LGGPSVFIFPPKPKDTLLIARTPEVTCVVVALDP

EDPEVQISWFVDGKQMQTAKTQPREEQFAGTYRV

VSVLPIGHQDWLKGKQFTCKVNNKALPSPIERTI

SKARGQAHQPSVYVLPPSREELSKNTVSLTCLIK

DFFPPPDIDVEWQSNGQQEPESKYRTTPPQLDEDG

SYFLYSKLSVDKSRWQRGDTFICAVMHEALHNHY

TQESLSHSPG
```

As used herein, a "substitution of an amino acid residue" with another amino acid residue in an amino acid sequence of an antibody for example, is equivalent to "replacing an amino acid residue" with another amino acid residue and denotes that a particular amino acid residue at a specific position in the amino acid sequence has been replaced by (or substituted for) by a different amino acid residue. Such substitutions can be particularly designed i.e., purposefully replacing an alanine with a serine at a specific position in the amino acid sequence by e.g., recombinant DNA technology. Alternatively, a particular amino acid residue or string of amino acid residues of an antibody can be replaced by one or more amino acid residues through more natural selection processes e.g., based on the ability of the antibody produced by a cell to bind to a given region on that antigen, e.g., one containing an epitope or a portion thereof, and/or for the antibody to comprise a particular CDR that retains the same canonical structure as the CDR it is replacing. Such substitutions/replacements can lead to "variant" CDRs and/or variant antibodies.

As used herein, the term "antibody" refers to any form of antibody that exhibits the desired biological activity. An antibody can be a monomer, dimer, or larger multimer. Thus, it is used in the broadest sense and specifically covers, but is not limited to, monoclonal antibodies (including full length monoclonal antibodies), polyclonal antibodies, multispecific antibodies (e.g., bispecific antibodies), caninized antibodies, fully canine antibodies, chimeric antibodies and camelized single domain antibodies. "Parental antibodies" are antibodies obtained by exposure of an immune system to an antigen prior to modification of the antibodies for an intended use, such as caninization of an antibody for use as a canine therapeutic antibody.

As used herein, antibodies of the present invention that "block" or is "blocking" or is "blocking the binding" of e.g., a canine receptor to its binding partner (ligand), is an antibody that blocks (partially or fully) the binding of the canine receptor to its canine ligand and vice versa, as determined in standard binding assays (e.g., BIACore®, ELISA, or flow cytometry).

Typically, an antibody or antigen binding fragment of the invention retains at least 10% of its canine antigen binding activity (when compared to the parental antibody) when that activity is expressed on a molar basis. Preferably, an antibody or antigen binding fragment of the invention retains at least 20%, 50%, 70%, 80%, 90%, 95% or 100% or more of the canine antigen binding affinity as the parental antibody. It is also intended that an antibody or antigen binding fragment of the invention can include conservative or non-conservative amino acid substitutions (referred to as "conservative variants" or "function conserved variants" of the antibody) that do not substantially alter its biologic activity.

"Isolated antibody" refers to the purification status and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

As used herein, an antibody is said to bind specifically to a polypeptide comprising a given antigen sequence (in this case a portion of the amino acid sequence of canine IL-31RA) if it binds to polypeptides comprising the portion of the amino acid sequence of canine IL-31RA, but does not bind to other canine proteins lacking that portion of the sequence of canine IL-31RA. For example, an antibody that specifically binds to a polypeptide comprising canine IL-31RA, may bind to a FLAG®-tagged form of canine IL-31RA, but will not bind to other FLAG®-tagged canine proteins. An antibody, or binding compound derived from the antigen-binding site of an antibody, binds to its canine antigen, or a variant or mutein thereof, "with specificity" when it has an affinity for that canine antigen or a variant or mutein thereof which is at least ten-times greater, more preferably at least 20-times greater, and even more preferably at least 100-times greater than its affinity for any other canine antigen tested.

As used herein, a "chimeric antibody" is an antibody having the variable domain from a first antibody and the constant domain from a second antibody, where the first and second antibodies are from different species. [U.S. Pat. No.

4,816,567; and Morrison et al., *Proc. Natl. Acad. Sci. USA* 81: 6851-6855 (1984)]. Typically the variable domains are obtained from an antibody from an experimental animal (the "parental antibody"), such as a rodent, and the constant domain sequences are obtained from the animal subject antibodies, e.g., human or canine so that the resulting chimeric antibody will be less likely to elicit an adverse immune response in a human or canine subject respectively, than the parental (e.g., rodent) antibody.

As used herein, the term "caninized antibody" refers to forms of antibodies that contain sequences from both canine and non-canine (e.g., rat) antibodies. In general, the caninized antibody will comprise substantially all of at least one or more typically, two variable domains in which all or substantially all of the hypervariable loops correspond to those of a non-canine immunoglobulin (e.g., comprising 6 CDRs as exemplified below), and all or substantially all of the framework (FR) regions (and typically all or substantially all of the remaining frame) are those of a canine immunoglobulin sequence. As exemplified herein, a caninized antibody comprises both the three heavy chain CDRs and the three light chain CDRS from a rat anti-canine antigen antibody together with a canine frame or a modified canine frame. A modified canine frame comprises one or more amino acids changes as exemplified herein that further optimize the effectiveness of the caninized antibody, e.g., to increase its binding to its canine antigen and/or its ability to block the binding of that canine antigen to the canine antigen's natural binding partner.

The variable regions of each light/heavy chain pair form the antibody binding site. Thus, in general, an intact antibody has two binding sites. Except in bifunctional or bispecific antibodies, the two binding sites are, in general, the same. Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of Sequences of Proteins of Immunological Interest, Kabat, et al.; National Institutes of Health, Bethesda, *Md.; 5th ed.; NIH Publ. No.* 91-3242 (1991); *Kabat, Adv. Prot. Chem.* 32:1-75 (1978); Kabat, et al., *J. Biol. Chem.* 252:6609-6616 (1977); Chothia, et al., *J. Mol. Biol.* 196:901-917 (1987) or Chothia, et al., *Nature* 342:878-883 (1989)].

As used herein, the term "hypervariable region" refers to the amino acid residues of an antibody that are responsible for antigen-binding. The hypervariable region comprises amino acid residues from a "complementarity determining region" or "CDR" (i.e. LCDR1, LCDR2 and LCDR3 in the light chain variable domain and HCDR1, HCDR2 and HCDR3 in the heavy chain variable domain). [See Kabat et al. *Sequences of Proteins of Immunological Interest,* 5th Ed. *Public Health Service*, National Institutes of Health, Bethesda, Md. (1991), defining the CDR regions of an antibody by sequence; see also Chothia and Lesk, *J. Mol. Biol.* 196: 901-917 (1987) defining the CDR regions of an antibody by structure]. As used herein, the term "framework" or "FR" residues refers to those variable domain residues other than the hypervariable region residues defined herein as CDR residues.

There are four known IgG heavy chain subtypes of dog IgG and they are referred to as IgG-A, IgG-B, IgG-C, and IgG-D. The two known light chain subtypes are referred to as lambda and kappa. In specific embodiments of the invention, besides binding canine IL-31RA, a canine or caninized antibody against its antigen of the present invention optimally has two attributes:

1. Lack of effector functions such as antibody-dependent cytotoxicity (ADCC) and complement-dependent cytotoxicity (CDC), and
2. be readily purified on a large scale using industry standard technologies such as that based on protein A chromatography.

None of the naturally occurring canine IgG isotypes satisfy both criteria. For example, IgG-B can be purified using protein A, but has high level of ADCC activity. On the other hand, IgG-A binds weakly to protein A, but also displays ADCC activity. Moreover, neither IgG-C nor IgG-D can be purified on protein A columns, although IgG-D displays no ADCC activity. (IgG-C has considerable ADCC activity). One way the present invention addresses these issues is by providing modified canine IgG-B antibodies of the present invention specific to an antigen of the present invention that lack the effector functions such as ADCC and can be easily purified using industry standard protein A chromatography.

As used herein an "antipruritic agent" is a compound, macromolecule, and/or formulation that tends to inhibit, relieve, and/or prevent itching. Antipruritic agents are colloquially referred to as anti-itch drugs.

As used herein an "antipruritic antibody" is an antibody that can act as an antipruritic agent in an animal, including a mammal such as a human, a canine, and/or a feline, particularly with respect to atopic dermatitis. In particular embodiments, the antipruritic antibody binds to specific proteins in the IL-31 signaling pathway, such as IL-31 or its receptor IL-31RA. The binding of the antipruritic antibody to its corresponding antigen (e.g., IL-31 or IL-31RA) inhibits the binding of e.g., IL-31 with IL-31RA, and interferes with and/or prevents the successful signaling of this pathway, and thereby inhibits, relieves, and/or prevents the itching that is otherwise caused by the IL-31 signaling pathway.

"Homology", as used herein, refers to sequence similarity between two polynucleotide sequences or between two polypeptide sequences when they are optimally aligned. When a position in both of the two compared sequences is occupied by the same base or amino acid residue, e.g., if a position in each of two DNA molecules is occupied by adenine, then the molecules are homologous at that position. The percent of homology is the number of homologous positions shared by the two sequences divided by the total number of positions compared ×100. For example, if 6 of 10 of the positions in two sequences are matched or homologous when the sequences are optimally aligned then the two sequences are 60% homologous. Generally, the comparison is made when two sequences are aligned to give maximum percent homology. Sequence identity refers to the degree to which the amino acids of two polypeptides are the same at equivalent positions when the two sequences are optimally aligned. As used herein one amino acid sequence is 100% "identical" to a second amino acid sequence when the amino acid residues of both sequences are identical.

Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In particular embodiments, selected deletions or insertions that could otherwise alter the correspondence between the two amino acid sequences are taken into account. Sequence similarity includes identical residues and nonidentical, biochemically related amino acids. Biochemically related amino acids that share similar properties and may be interchangeable.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity [see, e.g., Watson et al., Molecular Biology of the Gene, *The Benjamin/Cummings Pub. Co.*, p. 224 (4th Ed.; 1987)]. In addition, substitutions of structurally or functionally similar amino acids are less likely to disrupt biological activity. Exemplary conservative substitutions are set forth in Table A directly below.

TABLE A

| Exemplary Conservative Amino Acid Substitutions | |
| --- | --- |
| Original residue | Conservative substitution |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala; Gly |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants," as used herein, refers to antibodies or fragments in which one or more amino acid residues have been changed without altering a desired property, such an antigen affinity and/or specificity. Such variants include, but are not limited to, replacement of an amino acid with one having similar properties, such as the conservative amino acid substitutions of Table A above.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The present invention provides isolated caninized antibodies of the present invention, methods of use of the antibodies in the treatment of a condition e.g., the treatment of atopic dermatitis in canines. In canine, there are four IgG heavy chains referred to as A, B, C, and D. These heavy chains represent four different subclasses of dog IgG, which are referred to as IgG-A (or IgGA), IgG-B (or IgGB), IgG-C(or IgGC) and IgG-D (or IgGD). Each of the two heavy chains consists of one variable domain (VH) and three constant domains referred to as CH-1, CH-2, and CH-3. The CH-1 domain is connected to the CH-2 domain via an amino acid sequence referred to as the "hinge" or alternatively as the "hinge region".

The nucleic acid and amino acid sequences of these four heavy chains were first identified by Tang et al. [*Vet. Immunol. Immunopathol.* 80: 259-270 (2001)]. The amino acid and nucleic sequences for these heavy chains are also available from the GenBank data bases. For example, the amino acid sequence of IgGA heavy chain has accession number AAL35301.1, IgGB has accession number AAL35302.1, IgGC has accession number AAL35303.1, and IgGD has accession number (AAL35304.1). Canine antibodies also contain two types of light chains, kappa and lambda. The DNA and amino acid sequence of these light chains can be obtained from GenBank Databases. For example, the kappa light chain amino acid sequence has accession number ABY 57289.1 and the lambda light chain has accession number ABY 55569.1.

In the present invention, the amino acid sequence for each of the four canine IgG Fc fragments is based on the identified boundary of CH1 and CH2 domains as determined by Tang et al, supra. Caninized rat anti-canine antibodies that bind canine IL-31RA include, but are not limited to: antibodies of the present invention that comprise canine IgG-A, IgG-B, IgG-C, and IgG-D heavy chains and/or canine kappa or lambda light chains together with rat anti-canine IL-31RA CDRs. Accordingly, the present invention provides caninized rat anti-canine antibodies of the present invention, including isolated caninized rat anti-canine antibodies, that bind to canine IL-31RA and that preferably also block the binding of that canine IL-31RA to canine IL-31.

Accordingly, the present invention further provides caninized rat antibodies and methods of use of the antibodies of the present invention in the treatment of a condition e.g., the treatment of atopic dermatitis in canines.

The present invention further provides full length canine heavy chains that can be matched with corresponding light chains to make a caninized antibody. Accordingly, the present invention further provides caninized rat anti-canine antigen antibodies (including isolated caninized rat anti-canine antibodies) of the present invention and methods of use of the antibodies of the present invention in the treatment of a condition e.g., the treatment of atopic dermatitis in canines.

The present invention also provides antibodies of the present invention that comprise a canine fragment crystallizable region (cFc region) in which the cFc has been genetically modified to augment, decrease, or eliminate one or more effector functions. In one aspect of the present invention, the genetically modified cFc decreases or eliminates one or more effector functions. In another aspect of the invention the genetically modified cFc augments one or more effector function. In certain embodiments, the genetically modified cFc region is a genetically modified canine IgGB Fc region. In another such embodiment, the genetically modified cFc region is a genetically modified canine IgGC Fc region. In a particular embodiment the effector function is antibody-dependent cytotoxicity (ADCC) that is augmented, decreased, or eliminated. In another embodiment the effector function is complement-dependent cytotoxicity (CDC) that is augmented, decreased, or eliminated. In yet another embodiment, the cFc region has been genetically modified to augment, decrease, or eliminate both the ADCC and the CDC.

In order to generate variants of canine IgG that lack effector functions, a number of mutant canine IgGB heavy chains were generated. These variants may include one or more of the following single or combined substitutions in the Fc portion of the heavy chain amino acid sequence: P4A, D31A, N63A, G64P, T65A, A93G, and P95A. Variant heavy chains (i.e., containing such amino acid substitutions) are cloned into expression plasmids and are transfected into HEK 293 cells along with a plasmid containing the gene encoding a light chain. Intact antibodies are expressed and purified from HEK 293 cells and then can be evaluated for binding to Fc$_\gamma$RI and C1q to assess their potential for mediation of immune effector functions. [See, U.S. Pat. No. 10,106,607 B2, the contents of which are hereby incorporated by reference in its entirety.]

The present invention also provides modified canine IgG-Ds which in place of its natural IgG-D hinge region they comprise a hinge region from:

```
IgG-A:
                                    SEQ ID NO: 79
FNECRCTDTPPCPVPEP

IgG-B:
                                    SEQ ID NO: 80
PKRENGRVPRPPDCPKCPAPEM;
or

IgG-C:
                                    SEQ ID NO: 81
AKECECKCNCNNCPCPGCGL.
```

Alternatively, the IgG-D hinge region can be genetically modified by replacing a serine residue with a proline residue, i.e., PKESTCKCIPPCPVPES, SEQ ID NO: 82 (with the proline residue (P) underlined and in bold substituting for the naturally occurring serine residue). Such modifications can lead to a canine IgG-D lacking fab arm exchange. The modified canine IgG-Ds can be constructed using standard methods of recombinant DNA technology [e.g., Maniatis et al., *Molecular Cloning, A Laboratory Manual* (1982)]. In order to construct these variants, the nucleic acids encoding the amino acid sequence of canine IgG-D can be modified so that it encodes the modified IgG-Ds. The modified nucleic acid sequences are then cloned into expression plasmids for protein expression.

The six complementary determining regions (CDRs) of a caninized rat anti-canine antibody, as described herein can comprises a canine antibody kappa (k) or lambda (l) light chain comprising a rat light chain LCDR1, LCDR2, and LCDR3 and a canine antibody heavy chain IgG comprising a rat heavy chain HCDR1, HCDR2, and HCDR3.

Nucleic Acids

The present invention further comprises the nucleic acids encoding the antibodies of the present invention (see e.g., Examples below).

Also included in the present invention are nucleic acids that encode immunoglobulin polypeptides comprising amino acid sequences that are at least about 70% identical, preferably at least about 80% identical, more preferably at least about 90% identical and most preferably at least about 95% identical (e.g., 95%, 96%, 97%, 98%, 99%, 100%) to the amino acid sequences of the caninized antibodies, with the exception of the CDRs which do not change, provided herein when the comparison is performed by a BLAST algorithm wherein the parameters of the algorithm are selected to give the largest match between the respective sequences over the entire length of the respective reference sequences. The present invention further provides nucleic acids that encode immunoglobulin polypeptides comprising amino acid sequences that are at least about 70% similar, preferably at least about 80% similar, more preferably at least about 90% similar and most preferably at least about 95% similar (e.g., 95%, 96%, 97%, 98%, 99%, 100%) to any of the reference amino acid sequences when the comparison is performed with a BLAST algorithm, wherein the parameters of the algorithm are selected to give the largest match between the respective sequences over the entire length of the respective reference sequences, are also included in the present invention.

As used herein, nucleotide and amino acid sequence percent identity can be determined using C, MacVector (MacVector, Inc. Cary, NC 27519), Vector NTI (Informax, Inc. MD), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wisconsin) pileup program using the default parameters.

The following references relate to BLAST algorithms often used for sequence analysis: BLAST ALGORITHMS: Altschul, S. F., et al., *J. Mol. Biol.* 215:403-410 (1990); Gish, W., et al., *Nature Genet.* 3:266-272 (1993); Madden, T. L., et al., *Meth. Enzymol.* 266:131-141(1996); Altschul, S. F., et al., *Nucleic Acids Res.* 25:3389-3402 (1997); Zhang, J., et al., *Genome Res.* 7:649-656 (1997); Wootton, J. C., et al., *Comput. Chem.* 17:149-163 (1993); Hancock, J. M. et al., *Comput. Appl. Biosci.* 10:67-70 (1994); ALIGNMENT SCORING SYSTEMS: Dayhoff, M. O., et al., "A model of evolutionary change in proteins." in *Atlas of Protein Sequence and Structure*, vol. 5, suppl. 3. M. O. Dayhoff (ed.), pp. 345-352, (1978); Natl. *Biomed. Res.* Found., Washington, DC; Schwartz, R. M., et al., "Matrices for detecting distant relationships." in *Atlas of Protein Sequence and Structure*, vol. 5, suppl. 3." (1978), M. O. Dayhoff (ed.), pp. 353-358 (1978), Natl. *Biomed. Res.* Found., Washington, DC; Altschul, S. F., J. Mol. Biol. 219:555-565 (1991); States, D. J., et al., *Methods* 3:66-70(1991); Henikoff, S., et al., *Proc. Natl. Acad Sci. USA* 89:10915-10919 (1992); Altschul, S. F., et al., *J. Mol. Evol.* 36:290-300 (1993); ALIGNMENT STATISTICS: Karlin, S., et al., *Proc. Natl. Acad Sci. USA* 87:2264-2268 (1990); Karlin, S., et al., *Proc. Natl. Acad. Sci. USA* 90:5873-5877 (1993); Dembo, A., et al., *Ann. Prob.* 22:2022-2039 (1994); and Altschul, S. F. "Evaluating the statistical significance of multiple distinct local alignments." in *Theoretical and Computational Methods in Genome Research* (S. Suhai, ed.), pp. 1-14, Plenum, New York (1997).

Antibody Protein Engineering

By way of example, and not limitation, the canine heavy chain constant region can be from IgG-B or a modified cFc, such as the IgG-Bm used herein [see, U.S. Pat. No. 10,106, 607 B2, hereby incorporated by reference in its entirety] and the canine light chain constant region can be from kappa or lambda.

The antibodies can be engineered to include modifications to the canine framework and/or the canine frame residues within the variable domains of a parental (i.e., rat) monoclonal antibody, e.g. to improve the properties of the antibody.

The construction of caninized anti-canine IL-31 receptor alpha monoclonal antibodies can be performed by determining a DNA sequence that encodes the heavy and light chains of canine IgG were determined. The DNA and protein sequence of the canine heavy and light chains are known in the art and can be obtained by searching of the NCBI gene and protein databases. As indicated above, for canine antibodies there are four known IgG subtypes: IgG-A, IgG-B, IgG-C, and IgG-D, and two types of light chains, i.e., kappa and lambda.

A caninized rat anti-canine IL-31 antibody can be produced recombinantly by methods that are known in the field. Mammalian cell lines available as hosts for expression of the antibodies or fragments disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

In certain embodiments, the antibody or antigen binding fragment comprises a heavy chain constant region, e.g., a canine constant region, such as IgG-A, IgG-B, IgG-C and IgG-D canine heavy chain constant region or a variant thereof. In certain embodiments, the antibody or antigen binding fragment comprises a light chain constant region, e.g., a canine light chain constant region, such as lambda or kappa canine light chain region or variant thereof. By way of example, and not limitation, the canine heavy chain constant region can be from IgG-B and the canine light chain constant region can be from kappa.

Epitope Mapping

The interaction of antibodies with their cognate protein antigens is mediated through the binding of specific amino acids of the antibodies (paratopes) with specific amino acids (epitopes) of target antigens. An epitope is an antigenic determinant that causes a specific reaction by an immunoglobulin. An epitope consists of a group of amino acids on the surface of the antigen. A protein of interest may contain several epitopes that are recognized by different antibodies. The epitopes recognized by antibodies are classified as linear or conformational epitopes. Linear epitopes are formed by a stretch of a continuous sequence of amino acids in a protein, while conformational epitopes are composed of amino acids that are discontinuous (e.g., far apart) in the primary amino acid sequence, but are brought together upon three-dimensional protein folding.

Epitope mapping refers to the process of identifying the amino acid sequences (i.e., epitopes) that are recognized by antibodies on their target antigens. Identification of epitopes recognized by monoclonal antibodies (mAbs) on target antigens has important applications. For example, it can aid in the development of new therapeutics, diagnostics, and vaccines. Epitope mapping can also aid in the selection of optimized therapeutic mAbs and help elucidate their mechanisms of action. Epitope information on IL-31 receptor alpha can also elucidate unique epitopes and define the protective or pathogenic effects of vaccines. Epitope identification also can lead to development of subunit vaccines based on chemical or genetic coupling of the identified peptide epitope to a carrier protein or other immunostimulating agents.

Epitope mapping can be carried out using polyclonal or monoclonal antibodies and several methods are employed for epitope identification depending on the suspected nature of the epitope (i.e., linear versus conformational). Mapping linear epitopes is more straightforward and relatively, easier to perform. For this purpose, commercial services for linear epitope mapping often employ peptide scanning. In this case, an overlapping set of short peptide sequences of the target protein are chemically synthesized and tested for their ability to bind antibodies of interest. The strategy is rapid, high-throughput, and relatively inexpensive to perform. On the other hand, mapping of a discontinuous epitope is more technically challenging and requires more specialized techniques such as x-ray co-crystallography of a monoclonal antibody together with its target protein, Hydrogen-Deuterium (H/D) exchange, Mass Spectrometry coupled with enzymatic digestion as well as several other methods known to those skilled in the art.

Epitope Binding and Cross-Blocking Antibodies

An anti-canine IL-31RA antibody or antigen-binding fragment thereof of the present invention includes any antibody or antigen-binding fragment thereof that binds to the same epitope in canine IL-31RA as the one of the antibodies, disclosed herein, bind, e.g., as the 28F12 antibody which binds to the epitope comprising the amino acid sequence of SEQ ID NO: 101, including caninized antibodies, and any antibody or antigen-binding fragment that cross-blocks (partially or fully) or is cross-blocked (partially or fully) by an antibody or fragment discussed herein for canine IL-31RA binding; as well as any variant thereof.

The cross-blocking antibodies and antigen-binding fragments can be identified based on their ability to cross-compete with e.g., the 28F12 antibody in standard binding assays (e.g., BIACore®, ELISA, as exemplified below, or flow cytometry). For example, standard ELISA assays can be used in which a recombinant canine IL-31RA protein is immobilized on the plate, one of the antibodies is fluorescently labeled and the ability of non-labeled antibodies to compete off the binding of the labeled antibody is evaluated. Additionally or alternatively, BIAcore® analysis can be used to assess the ability of the antibodies to cross-compete. The ability of a test antibody to inhibit the binding of the 28F12 antibody, to canine IL-31RA demonstrates that the test antibody can compete with the 28F12 antibody for binding to canine IL-31RA and thus, may, in some cases, bind to the same epitope on canine IL-31RA as the 28F12 antibody binds. Antibodies and fragments thereof that bind to the same epitope as any of the anti-canine IL-31RA antibodies or fragments of the present invention also form part of the present Pharmaceutical Compositions and Administration To prepare pharmaceutical or sterile compositions comprising the antibodies of the present invention, these antibodies can be admixed with a pharmaceutically acceptable carrier or excipient. [See, e.g., *Remington's Pharmaceutical Sciences* and U.S. Pharmacopeia: National Formulary, Mack Publishing Company, Easton, PA (1984)].

Formulations of therapeutic and diagnostic agents may be prepared by mixing with acceptable carriers, excipients, or stabilizers in the form of, e.g., lyophilized powders, slurries, aqueous solutions or suspensions [see, e.g., Hardman, et al. (2001) Goodman and Gilman's The Pharmacological Basis of Therapeutics, *McGraw-Hill*, New York, NY; Gennaro (2000) Remington: The Science and Practice of Pharmacy, Lippincott, Williams, and Wilkins, New York, NY; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, NY]. In one embodiment, the antibodies of the present invention are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, antibodies exhibiting high therapeutic indices are desirable. The data obtained from these cell culture assays and animal studies can be used in formulating a range of dosage for use in canines. The dosage of such compounds lies preferably within a range of circulating concentrations that include the $ED_{50}$ with little or no toxicity. The dosage may vary within this range depending upon the dosage form employed and the route of administration.

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial. In particular embodiments, the antibodies of the present invention can be administered by an invasive route such as by injection. In further embodiments of the invention, the antibodies of the present invention, or pharmaceutical composition thereof, is administered intravenously, subcutaneously, intramuscularly, intraarterially, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector. The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

The pharmaceutical compositions disclosed herein may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternatively, one may administer the antibodies of the present invention in a local rather than systemic manner, often in a depot or sustained release formulation.

The administration regimen depends on several factors, including the serum or tissue turnover rate of the therapeutic antibodies, the level of symptoms, the immunogenicity of the therapeutic antibodies and the accessibility of the target cells in the biological matrix. Preferably, the administration regimen delivers sufficient therapeutic antibodies to effect improvement in the target disease/condition state, while simultaneously minimizing undesired side effects. Accordingly, the amount of biologic delivered depends in part on the particular therapeutic antibodies and the severity of the condition being treated. Guidance in selecting appropriate doses of therapeutic antibodies is available [see, e.g., Wawrzynczak Antibody Therapy, Bios Scientific Pub. Ltd, Oxfordshire, U K (1996); Kresina (ed.) Monoclonal Antibodies, Cytokines and Arthritis, Marcel Dekker, New York, NY (1991); Bach (ed.) Monoclonal Antibodies and Peptide Therapy in Autoimmune Diseases, Marcel Dekker, New York, NY (1993); Baert, et al. *New Engl. J. Med* 348:601-608 (2003); Milgrom et al. *New Engl. J. Med.* 341:1966-1973 (1999); Slamon et al. New *Engl. J. Med.* 344:783-792 (2001); Beniaminovitz et al. *New Engl. J. Med* 342:613-619 (2000); Ghosh et al. *New Engl. J. Med.* 348:24-32 (2003); Lipsky et al. *New Engl. J. Med.* 343:1594-1602 (2000)].

Determination of the appropriate dose is made by the veterinarian, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of the symptoms.

Antibodies provided herein may be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µm/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more [see, e.g., Yang, et al. *New Engl. J. Med* 349:427-434 (2003); Herold, et al. *New Engl. J. Med.* 346:1692-1698 (2002); Liu, et al. *J. Neurol. Neurosurg. Psych.* 67:451-456 (1999); Portielji, et al. *Cancer Immunol. Immunother.* 52:133-144 (2003)]. Doses may also be provided to achieve a predetermined target concentration of antibodies of the present invention in the canine's serum, such as 0.1, 0.3, 1, 3, 10, 30, 100, 300 µg/ml or more. In other embodiments, antibodies of the present invention is administered subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject (e.g., a canine) with a disorder, condition and/or symptom, or with the potential to develop such a disorder, disease or symptom.

As used herein, the terms "therapeutically effective amount", "therapeutically effective dose" and "effective amount" refer to an amount of antibodies of the present invention that, when administered alone or in combination with an additional therapeutic agent to a cell, tissue, or subject, e.g., canine, is effective to cause a measurable improvement in one or more symptoms of a disease or condition or the progression of such disease or condition. A therapeutically effective dose further refers to that amount of the antibodies sufficient to result in at least partial amelioration of symptoms, e.g., treatment, healing, prevention or amelioration of the relevant medical condition, or an increase in rate of treatment, healing, prevention or amelioration of such conditions. When applied to a combination, a therapeutically effective dose refers to combined amounts of the active ingredients that result in the therapeutic effect, whether administered in combination, serially, or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess severity of the condition.

EXAMPLES

Example 1

IL-31 Receptor alpha

Nucleotide Sequence

The nucleotide sequence of SEQ ID NO: 1 encodes the extracellular domain of the canine IL-31 receptor alpha (cIL-31RA) fused to a HIS tag. Canine IL-31RA ECD HIS-tagged protein comprises the amino acid sequence of SEQ ID NO: 2. The nucleotide sequence was prepared by chemical synthesis and then cloned into expression plasmids that are suitable for production of the corresponding proteins in eukaryotic cells, either HEK-293 or CHO cells.

```
Canine IL-31RA ECD-10His:
                                    [SEQ ID NO: 1]
gtgctgcccgccaagcccgagaacatcagctgcatcttct actacgaggagaacttcacctgcacctggagccccgagaa ggaggccagctacacctggtacaaggtgaagagaacctac agctacggctacaagagcgacatctgcagcaccgacaaca gcaccagaggcaaccacgccagctgcagcttcctgccccc caccatcaccaaccccgacaactacaccatccaggtggag gcccagaacgccgacggcatcatgaagagcgacatcacct actggaacctggacgccatcatgaagatcgagccccccga gatcttcagcgtgaagagcgtgctgggcatcaagagaatg ctgcagatcaagtggatcagacccgtgctggccccccaca gcagcaccctgaagtacacccctgagattcagaaccatcaa cagcgcctactggatggaggtgaacttcaccaaggaggac atcgacagagacgagacctacaacctgaccgagctgcagg ccttcaccgagtacgtgatgaccctgagatgcgcccccgc cgagagcatgttctggagcggctggagccaggagaaggtg ggcaccaccgaggaggaggcccctacggcctggacctgt ggagagtgctgaagcccgccatggtggacggcagaagacc cgtgcagctgatgtggaagaaggccaccggcgcccccgtg ctggagaaggccctgggctacaacatctggtacttccccg agaacaacaccaacctgaccgagaccgtgaacaccaccaa ccagacccacgagctgtacctgggcggcaagacctactgg gtgtacgtggtgagctacaacagcctgggcgagagccccg tggccaccctgagaatccccgccctgaacgagaagaccatt ccagtgcatcgaggccatgcaggcctgcctgacccaggac cagctggtggtggagtggcagagcagcgcccccgaggtgg acacctggatggtggagtggttccccgacgtggacagcga gcccagcagcttcagctgggagagcgtgagccaggccaga aactggaccatccagaaggacgagctgaagcccctgtggt gctacaacatcagcgtgtacccgtgctgagagacagagt gggccagccctacagcacccaggcctacgtgcaggagggc atccccagcgccggcccccgtgacccaggccgacagcatcg gcgtgaagaccgtgaccatcacctggaaggagatccccaa gagcaagagaaacggcttcatcaagaactacaccatcttc taccaggccgaggacggcaaggagttcagcaagaccgtga acagcaacatcctgcagtacagactggagagcctgaccag
```

```
                    -continued
aagaaccagctacagcctgcaggtgatggccagcaccaac gccggcggcaccaacggcaccaagatcaacttcaagaccc tgagcatcagccaccaccaccaccaccaccaccaccacca c
```

Example 2

Expression and Purification of IL-31 Receptor alpha ECD

Plasmids comprising the nucleotide sequence of SEQ ID NO: 1 were transfected into HEK-293 or CHO cells using electroporation via the MaxCyte instrument as per the manufacturer's recommendation. Several days following transfection, the supernatants of transfected cells and untransfected controls were harvested and spun down to remove cellular debris. IL-31RA with the HIS tag was purified from cell culture fluids by passing the clarified harvested fluid from transfected cells over nickel columns as per the manufacturer's recommendation. Purified proteins were quantified by measuring their absorbance of ultraviolet light at 280 nm.

```
Canine IL-31RA ECD-10His:
                                   [SEQ ID NO: 2]
VLPAKPENISCIFYYEENFTCTWSPEKEASYTWYKVKRTY

SYGYKSDICSTDNSTRGNHASCSFLPPTITNPDNYTIQVE

AQNADGIMKSDITYWNLDAIMKIEPPEIFSVKSVLGIKRM

LQIKWIRPVLAPHSSTLKYTLRFRTINSAYWMEVNFTKED

IDRDETYNLTELQAFTEYVMTLRCAPAESMEWSGWSQEKV

GTTEEEAPYGLDLWRVLKPAMVDGRRPVOLMWKKATGAPV

LEKALGYNIWYFPENNTNLTETVNTTNQTHELYLGGKTYW

VYVVSYNSLGESPVATLRIPALNEKTFQCIEAMQACLTQD

QLVVEWQSSAPEVDTWMVEWFPDVDSEPSSFSWESVSQAR

NWTIQKDELKPLWCYNISVYPVLRDRVGOPYSTQAYVQEG

IPSAGPVTQADSIGVKTVTITWKEIPKSKRNGFIKNYTIF

YQAEDGKEFSKTVNSNILQYRLESLTRRTSYSLOVMASTN

AGGINGTKINFKTLSISHHHHHHHHHH
```

Example 3

Binding OF Canine IL-31RA to Biotinylated Canine IL-31

Protocol
1. Coat immunoplate(s) with IL-31RA proteins by diluting to 1 µg/mL in phosphate-buffered saline solution (PBS). Add 100 µL/well. Incubate the plate(s) at 2-7° overnight.
2. Wash the plates 3 times with 275 µL/well of phosphate-buffered saline solution plus TWEEN 20 (PBST).
3. Block the plates with 200 µL/well of blocking buffer [1% nonfat dried milk (NFDM) in PBST] for 30-45 minutes at 36±2° C. with gentle shaking (120±20 RPM).

4. Wash the plates 3 times with 275 μL/well of PBST.

5. 3-fold dilute biotinylated IL-31 (at 10 μg/mL) in 1% NFDM in PBST on a dilution plate, and transfer 100 μL/well to the immunoplate(s). Incubate for 30-45 minutes at 36±2° C. with gentle shaking (120±20 RPM).

6. Wash the plates 3 times with 275 μL/well of PBST.

7. Dilute horse raddish peroxidase-Streptavidin (HRP-Streptavidin) to a final dilution of 1:1000 in 1% NFDM in PBST.

8. Add 100 μL/well of HRP-Streptavidin to the immuno-plate(s) and incubate for 30-45 minutes at 36±2° C. with gentle shaking (120±20 RPM).

9. Wash the plates 3 times with 275 μL/well of PBST.

10. Combine equal volumes of pre-warmed TMP 2-Component substrate immediately before use.

11. Add 100 μL/well of prepared 3,3',5,5'-tetramethylbenzidine (T substrate to the immunoplate(s) and incubate in the dark for 10 to 15 minutes at 36±2° C. with gentle shaking (120±20 RPM).

12. Stop the reaction by addition of 100 μL/well of 1 M $H_3PO_4$.

13. Read the plates using a microplate reader at a wavelength of 450 nm with a reference wavelength of 540 nm.

Example 4

Monoclonal Antibodies Against Canine IL-31 Receptor alpha

Monoclonal antibodies (mAbs) against canine IL-31RA were produced by the immunization of two Lewis rats multiple times with canine IL-31RA ECD (using 10 μg or 25 μg of antigen/rat each time) over a 3 to 4 week period. Following immunization, sera was collected from each rat and tested against canine IL-31RA by ELISA. The lymph node cells of the rat with the highest IL-31RA ECD reactivity were fused with the myeloma SP2/0 cell line to produce hybridomas. Approximately 10 days after the fusion, supernatants from growing hybridomas were screened on IL-31RA ECD protein coated plates by ELISA using the protocol described below. There were approximately 260 clones selected that showed potential binding to IL-31RA in this ELISA, as exemplified in FIGS. 2A-2E below with the rat IgG2a/Kappa used as the negative control. The majority of clones had an OD450 >1.

The procedure for the ELISA:

1. Coat 96-well half area plates with IL-31RA (1 μg/mL in PBS buffer), 25 μL/well.

2. Incubate the plates at 4° C. overnight.

3. Wash the plates 3 times with PBST (PBS+0.05% Tween 20)

4. Block the plates with blocking buffer (PBS with 5% fetal bovine serum (FBS)], 25 ul/well for minutes at room temperature.

5. Transfer 25 ul/well hybridoma supernatant to the 96-well plates, incubate 60 minutes at room temperature.

6. Wash the plates 3 times with PBST.

7. Add 25 ul/well anti-rat HRP, 1:4000 dilution in blocking buffer, to the plates and incubate 60 minutes at room temperature.

8. Wash the plates 5 times by PBST.

9. Add TMB based reagent to the plates for colorimetric reaction for 2-3 minutes.

10. Stop the reactions with 0.16M sulfuric acid.

11. Read the plates by plate reader.

Fourteen rat antibodies raised against canine IL-31RA that bind IL-31 were selected. The heavy and light chain variable regions of the rat antibodies are provided below. These antibodies were further tested in Example 5 below for their ability to block the binding of canine IL-31RA to canine IL-31.

```
49D3VH
                                    [SEQ ID NO: 49]
EVQLVESGGGLVQPGRSMKLSCAASGFTFSNYYMAWVRQA

PTKGLEWVASISTGGGNTYYRDSVKGRFTISRDNAKSTLY

LQMDSLRSEDTATYYCARHGTLYFDYWGQGVMVTVSS

49D3VL
                                    [SEQ ID NO: 50]
QFTLTQPKSVSGSLRSTITIPCERSSGDIGDSYVSWYQQH

LGRPPINVIYADDQRPSEVSDRESGSIDSSSNSASLTITN

LQMDDEADYFCQSYDSNIDGPVFGGGTKLTVL

10A12VH
                                    [SEQ ID NO: 51]
EVQLVESGGGLVKPGRSMKLSCAASGFTFSNYYMAWVRQA

PTKGLEWVASISTGGGNTYYRDSVKGRFTISRDNAKRTLY

LQMDSLRSEDTATYYCGRHGTLYFDYWGQGVMVTVSS

10A12VL
                                    [SEQ ID NO: 52]
QFTLTQPKSVSGSLRSTITIPCERSSGDIGDSYVSWYQQH

LGRPPINVIYVDDQRPSEVSDRESGSIDSSSNSASLTITD

LQMDDEADYFCQSYDSNIDGPVFGGGTKLTVL

47F3VH
                                    [SEQ ID NO: 53]
EVQLVESGGGLVQPGRSMKLSCVASGFTFSNYYMAWVRQA

PTKGLEWVASISTGGGNTYYRDSVKGRFTISRDNAKSTLY

LQMDSLRSEDTATYYCARHGTLYFDYWGQGVMVTVS

47F3VL
                                    [SEQ ID NO: 54]
QFTLTQPKSVSGSLRSTITIPCERSSGDIGNTYVSWYQQH

LGRPPINVIYADDQRPSEVSDRESGSIDSSSNSASLTITN

LQMDDEADYFCQSYDSNIDGPVFGGGTKLTVL

51G4VH
                                    [SEQ ID NO: 55]
EVQLVESGGGLVQPGRSMKLSCAALGFTFSNYYMAWVRQA

PTKGLEWVASISTGGGNTYYRDSVKGRFTISRDNAKNTLY

LQMDSLRSEDTATYYCARHGTIAAMDYWGQGVMVTVSS

51G4VL
                                    [SEQ ID NO: 56]
QFTLTQPKSVSGSLRSTITIPCERNNGDIGDSYVSWYQQH

LGRPPIIVIYADDQRPSEVSDRFSGSIDSSSNSASLTITN

LQMDDEADYFCQSYDSNIDGPVFGGGTKLTVL

53B3VH
                                    [SEQ ID NO: 57]
EVQLVESGGGLVQPGRSMKLSCAAFGFTENNYYMAWVRQA

PTKGLEWVASISTGGGNTFYRDSVKGRFTISRDNVKSILS

LQMDSLRSEDTATYYCARHGTIAAMDYWGQGVMVTVSS
```

-continued

53B3VL

[SEQ ID NO: 58]
QFTLTQPKSVSGSLRSTITIPCERTSGDIGDNYVSWYQQH

LGRPPINVIYADDQRPSEVSDRESGSIDSSSNSASLTITN

LQMDDEADYFCQSYDSNIDGPVFGGGTKLTVL

27A10VH

[SEQ ID NO: 59]
EVQLVESGGGLVQPGRSMKLSCTASGFTFSNYYMAWVRQA

PTKGLEWVASISTGGGNTYYRDSVKGRFTISRDNAKSTLY

LQMDSLRAEDTATYYCARHTMGYFDYWGQGVMVTVSS

27A10VL

[SEQ ID NO: 60]
QFTLTQPKSVSGSLRSTITIPCERSSGDIGDNYVSWYQQH

LGRPPINVIYADDQRPSEVSDRESGSIDSSSNSASLTITN

LQMDDEADYFCQSYDGKIEIPVFGGGTKLTVL

44E2VH

[SEQ ID NO: 61]
QVQLKESGPGLVQPSQTLSLTCTVSGFSLTSNGVSWVRQP

PGKGLEWIAAISSGGSTYYNSVLKSRLSISRDTSKSQVFL

KMNSLQTEDTAIYFCTRRLSGYNYVPFAYWGQGTLVTVSS

44E2VK

[SEQ ID NO: 62]
DIQMTQSPSLLSASVGDRVTLNCKASQNIYKHLAWCQQKL

GEPPNLLISNANSLQTGIPSRESGSGSGTDFTLTISSLQP

EDVATYFCQQYYSGDTFGAGTKLELK

4G7VH

[SEQ ID NO: 63]
EVQLQQYGAELGKPGTSVKLSCKVSGYNIRSTFMHWVNQR

PGKGLEWIGRIDPVNGNTIYSEKFKSKATLTADTSSNTAY

MQLSQLKSDDTAIYFCAMFNYAGHSGDYWGQGVMVTVSS

4G7VK

[SEQ ID NO: 64]
DIQMTQSPSSMSVSLGDTVTITCRASQDVGIYVNWFQQKP

GKSPRRMIYRATNLADGVPSRFSGSRSGSDYSLTISSLES

EDVADYHCLQYDEYPYTFGAGTKLELK

28F12VH

[SEQ ID NO: 65]
EVQLVESDGGLAQPGRSLKLSCAASGFTFSDYYMAWVRQA

PTKGLEWVATISYDGSSTYYRDSVRGRFTISRDNAKSTLY

LQMDSLRSEDTATYYCARGPLTDWAPNWFAYWGQGTLVTV

SS

28F12VK

[SEQ ID NO: 66]
DIQMTQSPASLSASLGETVTIQCQTSEDIYSGLAWYQQKP

GKSPQFLIYGASRLEDGVPSRESGSGSGTQYSLKISSMQT

EDEGVYFCQQGLKYPNTFGAGTKLELK

-continued

38A6VH

[SEQ ID NO: 67]
EVQLVESGGGLVQPGRSLKLSCVASGFTENNYWMTWIRQA

PGKGLEWVASITNTGGTTYYPDSVKGRFTISRDNAKSTLY

LQMNSLRSEDTATYYCTRGPTTVVGGWFAYWGQGTLVTVS

S

38A6VK

[SEQ ID NO: 68]
DIVMTQSPTSMSISVGDRVTMNCKASQNVGSNVDWYQQKT

GQSPKVLIYRASSRSTGVPDRFTGSGSGTDFTFTISNMQA

EDLAVYYCMQSNSYPPTFGGGTKLELK

20B8VH

[SEQ ID NO: 69]
EVQLVESGGGLVQPGRSLKLSCVASGFTENNYWMTWIRQA

PGKGLEWVASITNTGGSTYYPDSVKGRFTISRDNAKSTLY

LQMNSLRSEDTATYYCTRGPTTVVGGWFAYWGQGTLVTVS

S

20B8VK

[SEQ ID NO: 70]
DIVMTQSPTSMSISVGDRVTMNCKASQNVGSNVDWYQQKT

GQSPKLLIYRPSNRYTGVPDRFTGSGSGTDFTFTISNMQA

EDLAVYYCMQSNSYPPTFGGGTKLELK

7D7VH

[SEQ ID NO: 71]
EVQLVESGGGLVQPGRSLKLSCVASGFTFNNYWMTWIRQA

PGKGLEWVASITNTGGSTFYPDSVKGRFTISRDNAKSTLY

LQMNSLRSEDTATYYCTRGPDYGGHLNWFAYWGQGTLVTV

SS

7D7VK

[SEQ ID NO: 72]
DIVMTQSPTSMSISAGDRVTMNCKASQNVGSNVDWYQQKT

GQSPKLLIYKASNRYTGVPDRCTGSGSGTDFTFTISNMQA

EDLAVYYCMQSNSYPPTFGGGTKLELK

22B4VH

[SEQ ID NO: 73]
EVQLVESGGGLVQPGRSLKLSCVASGFTENKYWMTWIRQA

PGKGLEWVASITNTGGSSYYSDSVKGRFTISRDNAKSTLY

LQMNSLRSEETATYYCTRGPDYGGHLNWFAYWGQGTLVTV

SS

22B4VK

[SEQ ID NO: 74]
DIVMTQSPTSMSISVGDRVTMNCKASQNVGSNVDWYQEKT

GQSPKLVIYKASNRYTGVPDRFTGSGSGTDFTFTISNMQA

EDLAVYYCMQSNSYPPTFGGGTKLELK

```
                    -continued
48B1VH
                              [SEQ ID NO: 75]
EVQLVESGGGLVQPGRTLKLFCVASGFTENNYWMTWIRQA

PGKGLEWVASITNTGGSTYYPDSVKGRFTISRDNAKSTLY

LQMNSLRSEDTATYYCTRGPDYGGHLNWFVYWGQGTLVTV

SS

48B1VK
                              [SEQ ID NO: 76]
DIVMTQSPTSMSISVGDRVTMNCKASQNVGSNVDWYQQKT

GQSPKLLIYKASNRYTGVPDRFTGSGSGTDFTFTISNMQA

EDLAVYYCMQSNSYPPTFGGGTKLELK
```

Example 5

Blocking Activity of Anti-IL-31 Receptor alpha antibodies

The ability of anti-canine IL-31RA hybridoma supernatants to block the binding of IL-31 to IL-31RA were evaluated in the blocking ELISA described below.

Protocol

1. Coat 96-well half area plates with IL-31RA (1 μg/mL in PBS buffer), 25 μL/well.
2. Incubate the plates at 4° C. overnight.
3. Wash the plates 3 times by PBST (PBS+0.05% Tween 20)
4. Block the plates with blocking buffer (PBS with 5% FBS), 25 ul/well, for 30 minutes at room temperature.
5. Transfer 25 ul/well hybridoma supernatant to the 96-well plates, incubate 60 minutes at room temperature.
6. Wash the plates 3 times with PBST.
7. Transfer 25 μL/well of biotinylated IL31 (0.5 μg/mL in blocking buffer,) incubate 60 minutes at room temperature.
8. Wash the plates 3 times with PBST.
9. Add 25 μl/well Streptavidin-HRP, 1:5000 dilution in blocking buffer, to the plates and incubate 60 minutes at room temperature.
10. Wash the plates five times with PBST.
11. Add TMB based reagent to the plates for colorimetric reaction for 2-3 minutes.
12. Stop the reactions with 0.16M sulfuric acid.
13. Read the plates by plate reader.

Figure 1:
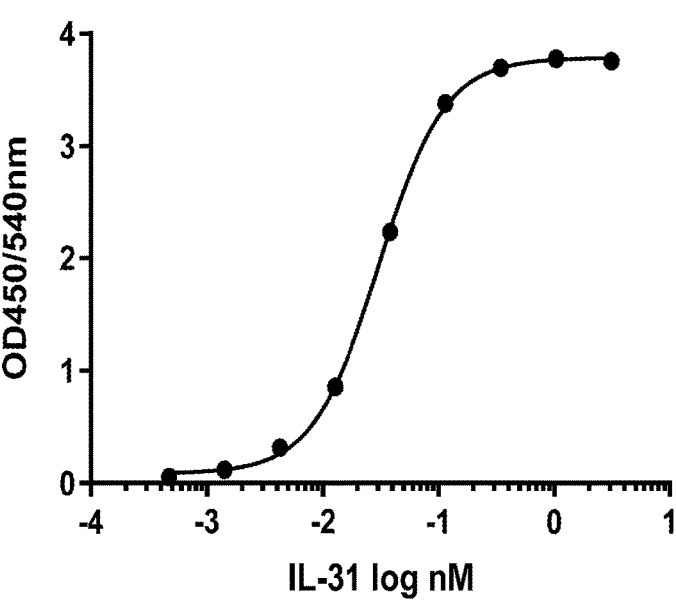
FIG. 1. The extracellular domain (ECD) of canine IL-31RA was tested for its ability to bind to canine IL-31. The results indicate that canine IL-31RA ECD binds in a dose-dependent manner to biotinylated canine IL-31.
Figure 2A:
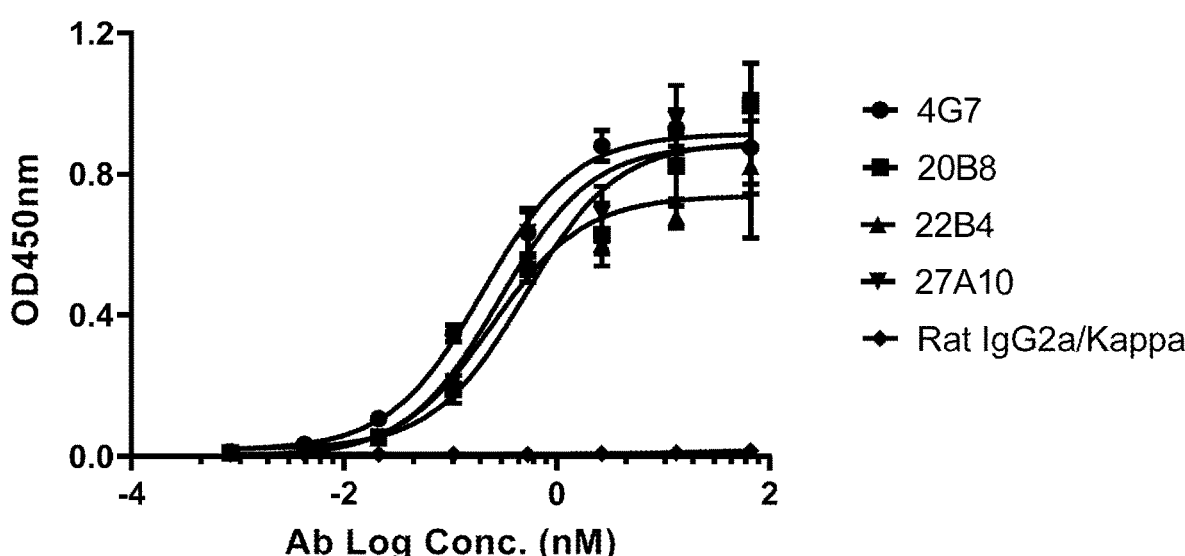
FIGS. 2A-2E. The selected rat mAbs to canine IL-31RA were tested for their reactivity to canine IL-31RA. The results indicate that the selected rat mAbs bind to canine IL-31RA in a dose-dependent manner. All the 14 rat monoclonal antibodies tested have strong binding reactivity to canine IL-31RA.
Figure 2B:
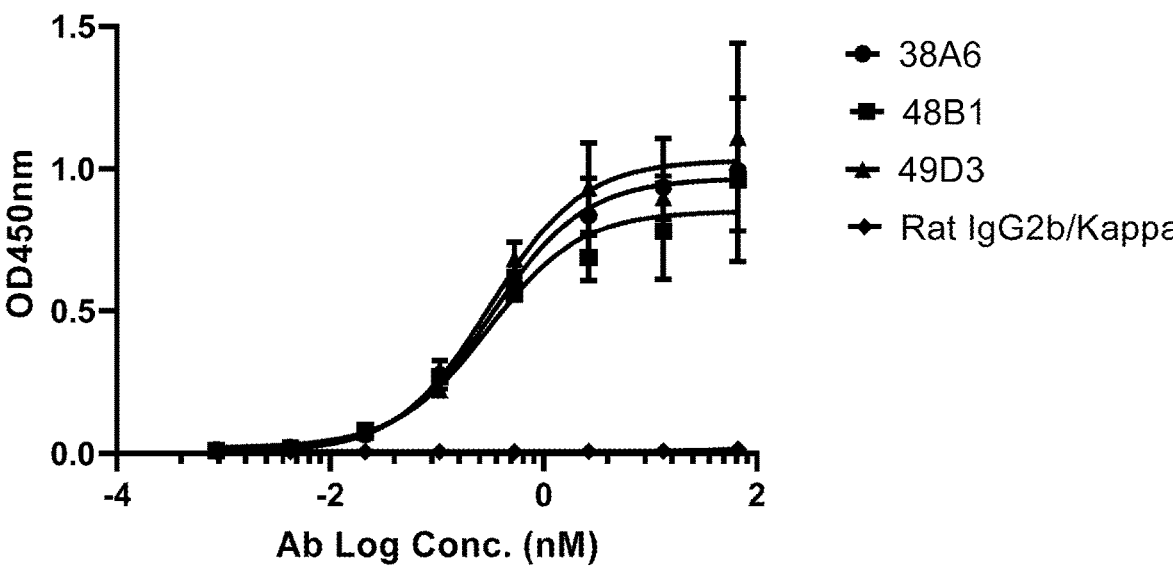
Figure 2C:
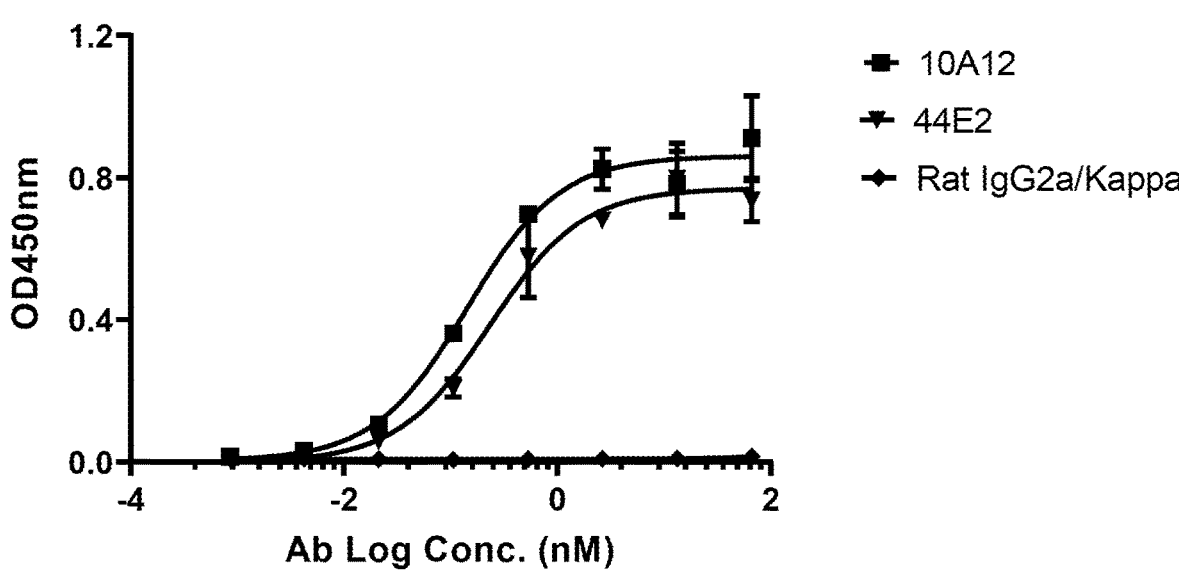
Figure 2D:
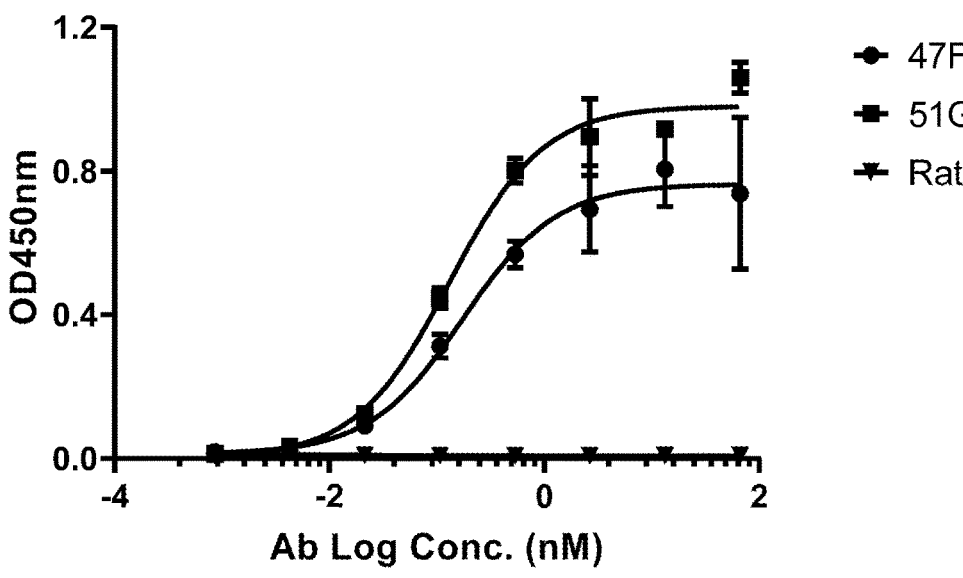
Figure 2E:
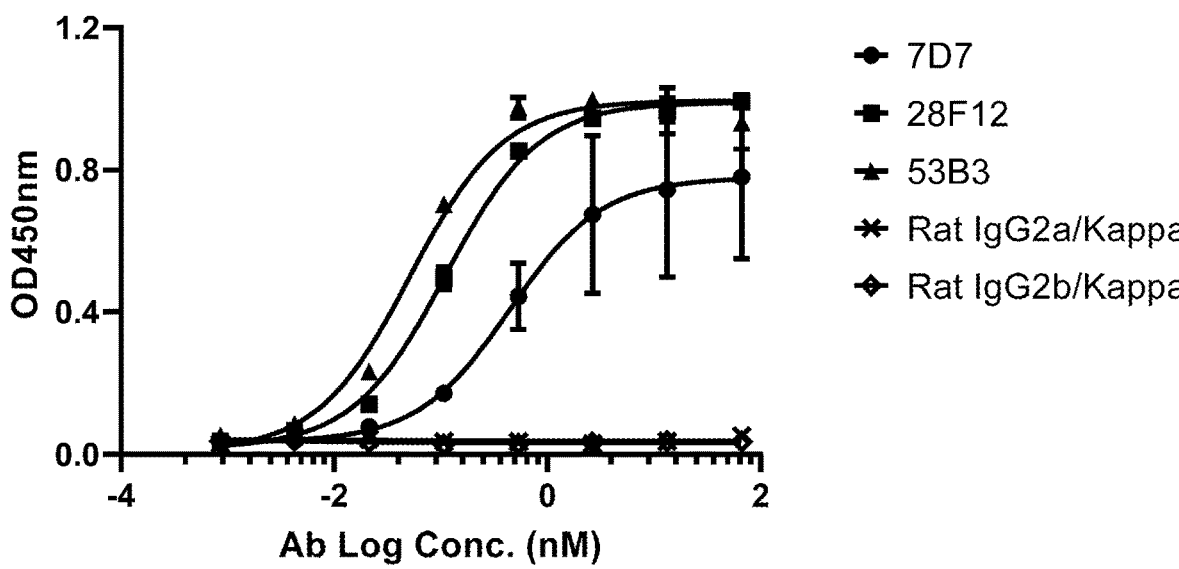
Figure 3:
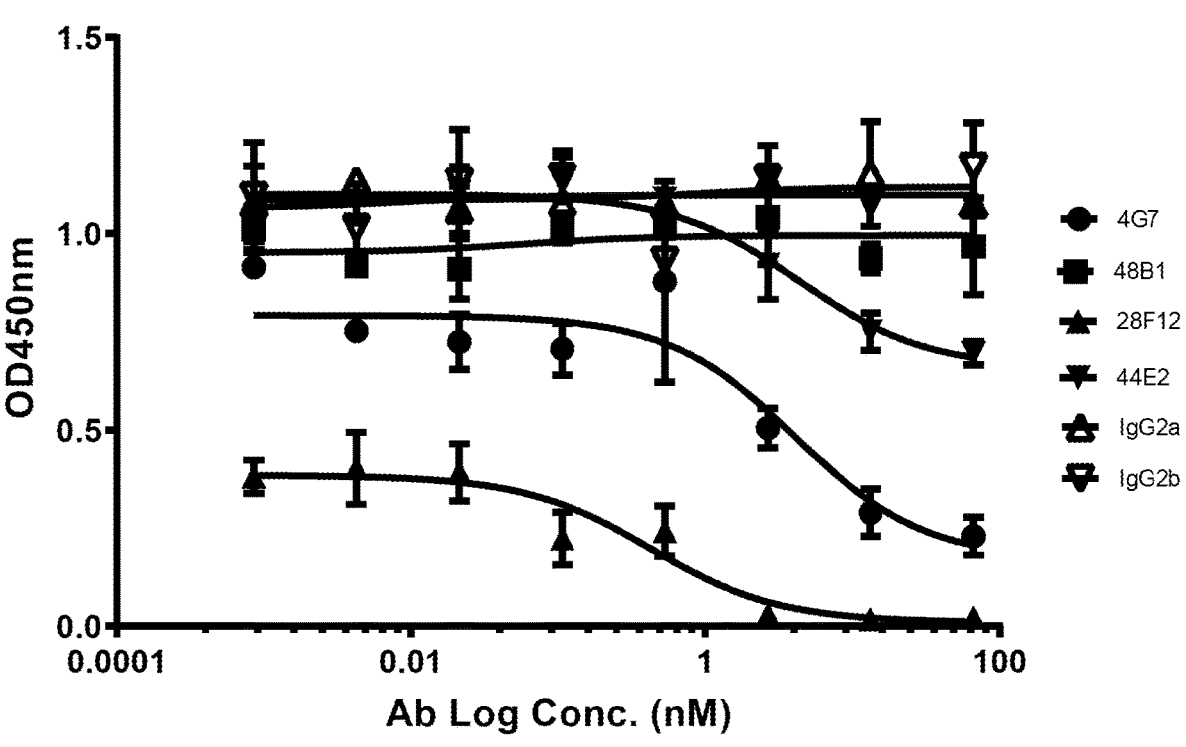
FIG. 3. The selected rat mAbs were tested for their ability to block the binding of canine IL-31 to canine IL-31RA by ELISA. The results indicated that some of the selected mAbs can block the binding of canine IL-31 to canine IL-31RA in a dose-dependent manner, whereas others could not.

Results:

Out of the approximately 260 clones that showed binding to IL-31RA, only 20 to 25 clones also showed potential blocking of canine IL-31 binding to canine IL-31RA. Of these, a particular group of three rat anti-canine IL-31RA antibodies (44E2, 4G7, and 28F12) that both bind IL-31RA and block the binding of IL-31 to IL-31RA were identified. See, FIG. 3, in which rat IgG2a and IgG2b was used as negative controls. These three antibodies appear to show some modest homology in the amino acid sequences of their respective CDRs. These amino acid sequences also are provided in Table 3 below.

| HEAVY CHAIN: | | | | |
|---|---|---|---|---|
| AB | HCDR1 | SEQ ID | HCDR2 | SEQ ID |
| 44E2 | SNGVS | NO: 13 | AISSGGST YYNSVLKS | NO: 14 |
| 4G7 | STEMH | NO: 19 | RIDPVNGN TIYSEKFKS | NO: 20 |
| 28F12 | DYYMA | NO: 25 | TISYDGSST YYRDSVRG | NO: 26 |

| AB | HCDR3 | SEQ ID |
|---|---|---|
| 44E2 | RLSGYNYV PFAY | NO: 15 |
| 4G7 | FNYAGHSGDY | NO: 21 |
| 28F12 | GPLTDWAP NWFAY | NO: 27 |

| LIGHT CHAIN: | | | | |
|---|---|---|---|---|
| AB | LCDR1 | SEQ ID | LCDR2 | SEQ ID |
| 44E2 | KASQNIYKHLA | NO: 16 | NANSLQT | NO: 17 |
| 4G7 | RASQDVGIYVN | NO: 22 | RATNLAD | NO: 23 |
| 28F12 | QTSEDIYSGLA | NO: 28 | GASRLED | NO: 29 |

| AB | LCDR3 | SEQ ID |
|---|---|---|
| 44E2 | QQYYSGDT | NO: 18 |
| 4G7 | LQYDEYPYT | NO: 24 |
| 28F12 | QQGLKYPNT | NO: 30 |

A second group of six rat anti-canine IL-31RA antibodies that both bind canine IL-31RA and block the binding of canine IL-31 to canine IL-31RA were identified as comprising sets of CDRs that have a striking amino acid sequence similarity. These amino acid sequences also are provided in Table 3 below.

| HEAVY CHAIN: | | | | |
|---|---|---|---|---|
| AB | HCDR1 | SEQ ID | HCDR2 | SEQ ID |
| 49D3 | NYYMA | NO: 31 | SISTGGGNTYYRDSVKG | NO: 32 |
| 10A12 | NYYMA | NO: 31 | SISTGGGNTYYRDSVKG | NO: 32 |
| 47F3 | NYYMA | NO: 31 | SISTGGGNTYYRDSVKG | NO: 32 |

-continued

| 27A10 | NYYMA | NO: 31 | SISTGGGNTYYRDSVKG | NO: 32 |
|---|---|---|---|---|
| 51G4 | NYYMA | NO: 31 | SISTGGGNTYYRDSVKG | NO: 32 |
| 53B3 | NYYMA | NO: 31 | SISTGGGNTFYRDSVKG | NO: 41 |

| AB | HCDR3 | SEQ ID | | |
|---|---|---|---|---|
| 49D3 | HGTLYFDY | NO: 33 | | |
| 10A12 | HGTLYFDY | NO: 33 | | |
| 47F3 | HGTLYFDY | NO: 33 | | |
| 27A10 | HTMGYFDY | NO: 43 | | |
| 51G4 | HGTIAAMDY | NO: 39 | | |
| 53B3 | HGTIAAMDY | NO: 39 | | |

LIGHT CHAIN:

| AB | LCDR1 | SEQ ID | LCDR2 | SEQ ID |
|---|---|---|---|---|
| 49D3 | ERSSGDIGDSYVS | NO: 34 | ADDQRPS | NO: 35 |
| 10A12 | ERSSGDIGDSYVS | NO: 34 | VDDQRPS | NO: 37 |
| 47F3 | ERSSGDIGNTYVS | NO: 38 | ADDQRPS | NO: 35 |
| 27A10 | ERSSGDIGDNYVS | NO: 44 | ADDQRPS | NO: 35 |
| 51G4 | ERNNGDIGDSYVS | NO: 40 | ADDQRPS | NO: 35 |
| 53B3 | ERTSGDIGDNYVS | NO: 42 | ADDQRPS | NO: 35 |

| AB | LCDR3 | SEQ ID | | |
|---|---|---|---|---|
| 49D3 | QSYDSNIDGPV | NO: 36 | | |
| 10A12 | QSYDSNIDGPV | NO: 36 | | |
| 47F3 | QSYDSNIDGPV | NO: 36 | | |
| 27A10 | QSYDGKIEIPV | NO: 45 | | |
| 51G4 | QSYDSNIDGPV | NO: 36 | | |
| 53B3 | QSYDSNIDGPV | NO: 36 | | |

Example 6

Caninized Antibodies

The overall process of producing caninized heavy and light chains that can be mixed in different combinations to produce caninized anti-canine IL-31 receptor alpha mAbs involves the following scheme:

i) Identify the DNA sequence of VH and VL domains comprising the CDRs of desired anti-IL-31 receptor alpha mAbs ii) Identify the H and L chain CDRs of desired anti-IL-31RA mAbs iii) Identify a suitable sequence for H and L chain of canine IgG iv) Identify the DNA sequence encoding the endogenous CDRs of canine IgG H and L chains of the above sequence.

v) Replace the DNA sequence encoding endogenous canine H and L chain CDRs with DNA sequences encoding the desired anti-IL-31RA CDRs. In addition, optionally replace some canine framework residues with selected residues from the desired anti-IL-31 receptor alpha mAb framework regions.

vi) Synthesize the DNA from step (v), clone it into a suitable expression plasmid, and transfect the plasmids containing desired caninized H and L chains into HEK 293 cells.

vii) Purify expressed caninized antibody from HEK 293 supernatant.

viii) Test purified caninized antibody for binding to canine IL-31 receptor alpha chain.

The application of the above outlined steps can result in a set of caninized H and L chain sequences provided below. The corresponding SEQ ID NOs. are listed in Table 5 below.

FIGS. 6A-6C show the binding of caninized anti-canine IL-31RA antibodies containing either lambda (L) or kappa (K) light chains as evaluated by ELISA. The results show that caninized anti-canine IL-31RA antibodies bind to canine IL-31RA.

FIGS. 7A-7C are plots showing the inhibition of cIL-31-mediated STAT-3 phosphorylation by cIL-31RA antibodies employing the assay described in Example 6 below. Three different caninized monoclonal anti-canine IL-31RA antibodies designated c10A12, c28F12, and c44E2 were evaluated for their ability to inhibit STAT-3 phosphorylation. The data show that all three antibodies result in a dose dependent inhibition of STAT-3 phosphorylation in the presence of IL-31.

```
Caninized Antibodies to Canine IL-31
Receptor alpha (cIL-31RA)
C10A12VL5-CCL
                                    [SEQ ID NO: 83]
QPVLTQPPSLSASLGTTARLTCERSSGDIGDSYVSWYQQK

PGSPPRDLLYVDDQRPSGVSKSFSGSKDTSANAGLLLISG

LQPEDEADYYCQSYDSNIDGPVFGGGTHLTVLGQPKASPS

VTLFPPSSEELGANKATLVCLISDFYPSGVTVAWKADGSP

VTQGVETTKPSKQSNNKYAASSYLSLTPDKWKSHSSFSCL

VTHEGSTVEKKVAPAECS

C10A12VH1-CIgGBm
                                    [SEQ ID NO: 84]
EVQLVESGGDLVKPGGSLRLSCVASGFTFSNYYMAWVRQA

PGKGLQWVASISTGGGNTYYRDSVKGRFTISRDNAKNTLY

LQMNSLRAEDTAMYYCAKHGTLYFDYWGQGTLVTVSSAST

TAPSVFPLAPSCGSTSGSTVALACLVSGYFPEPVTVSWNS

GSLTSGVHTFPSVLQSSGLYSLSSMVTVPSSRWPSETFTC

NVAHPASKTKVDKPVPKRENGRVPRPPDCPKCPAPEMLGG

PSVFIFPPPKPKDTLLIARTPEVTCVVVALDPEDPEVQISW

FVDGKQMQTAKTQPREEQFAGTYRVVSVLPIGHQDWLKGK

QFTCKVNNKALPSPIERTISKARGQAHQPSVYVLPPSREE

LSKNTVSLTCLIKDFFPPDIDVEWQSNGQQEPESKYRTTP

PQLDEDGSYFLYSKLSVDKSRWQRGDTFICAVMHEALHNH

YTQESLSHSPGK c10A12VH2-cIgGBm
                                    [SEQ ID NO: 85]
EVQLVESGGDLVKPGGSLRLSCAASGFTESNYYMAWVRQA

PGKGLQWVASISTGGGNTYYRDSVKGRFTISRDNAKNTLY

LQMNSLRAEDTAMYYCARHGTLYFDYWGQGTLVTVSSAST

TAPSVFPLAPSCGSTSGSTVALACLVSGYFPEPVTVSWNS

GSLTSGVHTFPSVLQSSGLYSLSSMVTVPSSRWPSETFTC

NVAHPASKTKVDKPVPKRENGRVPRPPDCPKCPAPEMLGG

PSVFIFPPPKPKDTLLIARTPEVTCVVVALDPEDPEVQISW

FVDGKQMQTAKTQPREEQFAGTYRVVSVLPIGHQDWLKGK

QFTCKVNNKALPSPIERTISKARGQAHQPSVYVLPPSREE

LSKNTVSLTCLIKDFFPPDIDVEWQSNGQQEPESKYRTTP

PQLDEDGSYFLYSKLSVDKSRWQRGDTFICAVMHEALHNH

YTQESLSHSPGK c10A12VL4-cCL
                                    [SEQ ID NO: 86]
QSVLTQPASVSGSLGQRVTISCERSSGDIGDSYVSWYQQL

PGKAPSLLIYVDDQRPSGVPERFSGSKSGSSNSATLTITG

LQAEDEADYYCQSYDSNIDGPVFGGGTHLTVLGQPKASPS
```

```
                       -continued
VTLFPPSSEELGANKATLVCLISDFYPSGVTVAWKADGSP

VTQGVETTKPSKQSNNKYAASSYLSLTPDKWKSHSSFSCL

VTHEGSTVEKKVAPAECS c10A12VL6-cCL
                                    [SEQ ID NO: 87]
QPVLTQPPSLSASLGTTARLTCERSSGDIGDSYVSWYQQK

PGSPPRDVIYVDDQRPSEVSKSFSGSKDTSANAGLLLISG

LQPEDEADYFCQSYDSNIDGPVFGGGTHLTVLGQPKASPS

VTLFPPSSEELGANKATLVCLISDFYPSGVTVAWKADGSP

VTQGVETTKPSKQSNNKYAASSYLSLTPDKWKSHSSFSCL

VTHEGSTVEKKVAPAECS c28F12VH1-cIgGBm
                                    [SEQ ID NO: 88]
EVQLVESGGDLVKPGGSLRLSCVASGFTFSDYYMAWVRQA

PGKGLQWVATISYDGSSTYYRDSVRGRFTISRDNAKNTLY

LQMNSLRAEDTAMYYCAKGPLTDWAPNWFAYWGQGTLVTV

SSASTTAPSVEPLAPSCGSTSGSTVALACLVSGYFPEPVT

VSWNSGSLTSGVHTFPSVLQSSGLYSLSSMVTVPSSRWPS

ETFTCNVAHPASKTKVDKPVPKRENGRVPRPPDCPKCPAP

EMLGGPSVFIFPPPKPKDTLLIARTPEVTCVVVALDPEDPE

VQISWFVDGKQMQTAKTQPREEQFAGTYRVVSVLPIGHQD

WLKGKQFTCKVNNKALPSPIERTISKARGQAHQPSVYVLP

PSREELSKNTVSLTCLIKDFFPPDIDVEWQSNGQQEPESK

YRTTPPQLDEDGSYFLYSKLSVDKSRWQRGDTFICAVMHE

ALHNHYTQESLSHSPGK c28F12VH2-cIgGBm
                                    [SEQ ID NO: 89]
EVQLVESGGDLVKPGGSLRLSCAASGFTFSDYYMAWVRQA

PGKGLQWVATISYDGSSTYYRDSVRGRFTISRDNAKNTLY

LQMNSLRAEDTAMYYCARGPLTDWAPNWFAYWGQGTLVTV

SSASTTAPSVFPLAPSCGSTSGSTVALACLVSGYFPEPVT

VSWNSGSLTSGVHTFPSVLQSSGLYSLSSMVTVPSSRWPS

ETFTCNVAHPASKTKVDKPVPKRENGRVPRPPDCPKCPAP

EMLGGPSVFIFPPPKPKDTLLIARTPEVTCVVVALDPEDPE

VQISWFVDGKQMQTAKTQPREEQFAGTYRVVSVLPIGHQD

WLKGKQFTCKVNNKALPSPIERTISKARGQAHQPSVYVLP

PSREELSKNTVSLTCLIKDFFPPDIDVEWQSNGQQEPESK

YRTTPPQLDEDGSYFLYSKLSVDKSRWQRGDTFICAVMHE

ALHNHYTQESLSHSPGK c28F12VK1-cCK
                                    [SEQ ID NO: 90]
DIVMTQTPLSLSVSPGETASISCQTSEDIYSGLAWFRQKP

GQSPQRLIYGASRLEDGVPDRESGSGSGTDFTLRISTVEA
```

-continued

```
DDTGVYYCQQGLKYPNTFGAGTKVELKRNDAQPAVYLFQP

SPDQLHTGSASVVCLLNSFYPKDINVKWKVDGVIQDTGIQ

ESVTEQDKDSTYSLSSTLTMSSTEYLSHELYSCEITHKSL

P
STLIKS FORSECORVD
``` c28F12VK2-cCK

[SEQ ID NO: 91]
```
EIVMTQSPASLSLSQEEKVTITCQTSEDIYSGLAWYQQKP

GQAPKLLIYGASRLEDGVPSRFSGSGSGTDFSFTISSLEP

EDVAVYYCQQGLKYPNTFGAGTKVELKRNDAQPAVYLFQP

SPDQLHTGSASVVCLLNSFYPKDINVKWKVDGVIQDTGIQ

ESVTEQDKDSTYSLSSTLTMSSTEYLSHELYSCEITHKSL

PSTLIKSFQRSECQRVD
``` c28F12VK3-cCK

[SEQ ID NO: 92]
```
DIVMTQSPASLSLSQEEKVTITCQTSEDIYSGLAWYQQKP

GQAPKLLIYGASRLEDGVPSRESGSGSGTDFSFTISSLEP

EDVAVYFCQQGLKYPNTFGAGTKVELKRNDAQPAVYLFQP

SPDQLHTGSASVVCLLNSFYPKDINVKWKVDGVIQDTGIQ

ESVTEQDKDSTYSLSSTLTMSSTEYLSHELYSCEITHKSL

PSTLIKSFQRSECQRVD
``` c28F12VK4-cCK

[SEQ ID NO: 93]
```
DIVMTQTPLSLSVSPGETASISCQTSEDIYSGLAWFRQKP

GQSPQLLIYGASRLEDGVPDRESGSGSGTDFTLRISTVEA

DDTGVYFCQQGLKYPNTFGAGTKVELKRNDAQPAVYLFQP

SPDQLHTGSASVVCLLNSFYPKDINVKWKVDGVIQDTGIQ

ESVTEQDKDSTYSLSSTLTMSSTEYLSHELYSCEITHKSL

PSTLIKSFQRSECQRVD
``` c44E2VH1-cIgGBm

[SEQ ID NO: 94]
```
EVQLVESGGDLVKPEGSLRLSCVVSGFTFSSNGVSWVRQA

PGKGLQWVAAISSGGSTYYNSVLKSRETISRDNAKNTLYL

QMNSLRTEDTAVYYCAKRLSGYNYVPFAYWGQGTLVTVSS

ASTTAPSVEPLAPSCGSTSGSTVALACLVSGYFPEPVTVS

WNSGSLTSGVHTFPSVLQSSGLYSLSSMVTVPSSRWPSET

FTCNVAHPASKTKVDKPVPKRENGRVPRPPDCPKCPAPEM

LGGPSVFIFPPKPKDTLLIARTPEVTCVVVALDPEDPEVQ

ISWFVDGKQMQTAKTQPREEQFAGTYRVVSVLPIGHQDWL

KGKQFTCKVNNKALPSPIERTISKARGQAHQPSVYVLPPS

REELSKNTVSLTCLIKDFFPPDIDVEWQSNGQQEPESKYR

TTPPQLDEDGSYFLYSKLSVDKSRWQRGDTFICAVMHEAL

HNHYTQESLSHSPGK
```

-continued c44E2VH4-cIgGBm

[SEQ ID NO: 95]
```
ELTLQESGPGLVKPSQTLSLTCVVSGGSVTSNGVSWIRQR

PGRGLEWMGAISSGGSTYYNSVLKSRISITADTAKNQFSL

QLSSMTTEDTAVYYCARRLSGYNYVPFAYWGQGTLVTVSS

ASTTAPSVFPLAPSCGSTSGSTVALACLVSGYFPEPVTVS

WNSGSLTSGVHTFPSVLQSSGLYSLSSMVTVPSSRWPSET

FTCNVAHPASKTKVDKPVPKRENGRVPRPPDCPKCPAPEM

LGGPSVFIFPPKPKDTLLIARTPEVTCVVVALDPEDPEVQ

ISWFVDGKQMQTAKTQPREEQFAGTYRVVSVLPIGHQDWL

KGKQFTCKVNNKALPSPIERTISKARGQAHQPSVYVLPPS

REELSKNTVSLTCLIKDFFPPDIDVEWQSNGQQEPESKYR

TTPPQLDEDGSYFLYSKLSVDKSRWQRGDTFICAVMHEAL

HNHYTQESLSHSPGK
``` c44E2VH5-cIgGBm

[SEQ ID NO: 96]
```
ELTLQESGPGLVKPSQTLSLTCTVSGFSLTSNGVSWIRQR

PGRGLEWMGAISSGGSTYYNSVLKSRISITADTAKNQFSL

QLSSMTTEDTAVYYCARRLSGYNYVPFAYWGQGTLVTVSS

ASTTAPSVEPLAPSCGSTSGSTVALACLVSGYFPEPVTVS

WNSGSLTSGVHTFPSVLQSSGLYSLSSMVTVPSSRWPSET

FTCNVAHPASKTKVDKPVPKRENGRVPRPPDCPKCPAPEM

LGGPSVFIFPPKPKDTLLIARTPEVTCVVVALDPEDPEVQ

ISWFVDGKQMQTAKTQPREEQFAGTYRVVSVLPIGHQDWL

KGKQFTCKVNNKALPSPIERTISKARGQAHQPSVYVLPPS

REELSKNTVSLTCLIKDFFPPDIDVEWQSNGQQEPESKYR

TTPPQLDEDGSYFLYSKLSVDKSRWQRGDTFICAVMHEAL

HNHYTQESLSHSPGK
``` c44E2VK1-cCK

[SEQ ID NO: 97]
```
EIVMTQSPASLSLSQEEKVTITCKASQNIYKHLAWYQQKP

GQAPKLLIYNANSLQTGVPSRESGSGSGTDFSFTISSLEP

EDVAVYYCQQYYSGDTFGAGTKVELKRNDAQPAVYLFQPS

PDQLHTGSASVVCLLNSFYPKDINVKWKVDGVIQDTGIQE

SVTEQDKDSTYSLSSTLTMSSTEYLSHELYSCEITHKSLP

STLIKSFQRSECQRVD
``` c44E2VK2-cCK

[SEQ ID NO: 98]
```
EIVMTQSPASLSLSQEEKVTITCKASQNIYKHLAWYQQKP

GQAPKLLIYNANSLQTGIPSRESGSGSGTDFSFTISSLEP

EDVAVYFCQQYYSGDTFGAGTKVELKRNDAQPAVYLFQPS
```

-continued

PDQLHTGSASVVCLLNSFYPKDINVKWKVDGVIQDTGIQE

SVTEQDKDSTYSLSSTLTMSSTEYLSHELYSCEITHKSLP

STLIKSFQRSECQRVD c44E2VK4-cCK

[SEQ ID NO: 99]
EIVMTQSPGSLAGSAGESVSINCKASQNIYKHLAWYQQKP

GERPKLLIYNANSLQTGVPARFSSSGSGTDFTLTINNLQA

EDVGDYYCQQYYSGDTFGAGTKVELKRNDAQPAVYLFQPS

PDQLHTGSASVVCLLNSFYPKDINVKWKVDGVIQDTGIQE

SVTEQDKDSTYSLSSTLTMSSTEYLSHELYSCEITHKSLP

STLIKSFQRSECQRVD c44E2VH2-cIgGBm

[SEQ ID NO: 100]
EVQLVESGGDLVKPEGSLRLSCVVSGFSLTSNGVSWVRQA

PGKGLQWIAAISSGGSTYYNSVLKSRLTISRDNAKNTLYL

QMNSLRTEDTAVYYCARRLSGYNYVPFAYWGQGTLVTVSS

ASTTAPSVEPLAPSCGSTSGSTVALACLVSGYFPEPVTVS

WNSGSLTSGVHTFPSVLQSSGLYSLSSMVTVPSSRWPSET

FTCNVAHPASKTKVDKPVPKRENGRVPRPPDCPKCPAPEM

LGGPSVFIFPPKPKDTLLIARTPEVTCVVVALDPEDPEVQ

ISWFVDGKQMQTAKTQPREEQFAGTYRVVSVLPIGHQDWL

KGKQFTCKVNNKALPSPIERTISKARGQAHQPSVYVLPPS

REELSKNTVSLTCLIKDFFPPDIDVEWQSNGQQEPESKYR

TTPPQLDEDGSYFLYSKLSVDKSRWQRGDTFICAVMHEAL

HNHYTQESLSHSPGK

Example 7

STAT-3 Assay

Stat-3 is known to be activated by IL-31 in cells comprising the heterodimeric receptor for IL-31. In order to develop an assay to assess the activation of STAT-3 by canine IL-31, the nucleotide sequences encoding IL-31RA and OSMR, respectively, were prepared by chemical synthesis and then cloned into expression vectors pcDNA3.1. The vectors containing the IL-31RA and OSMR nucleotide sequences, respectively, were co-transfected into Ba/f3 cells and the transfected cells, denoted as "Ba/f3-OI", were grown as a pool under antibiotic selection. The ability of canine IL-31 to induce STAT-3 activation was tested as follows.

Materials:

Cell line: Ba/f3-OI stable pool cells

Growth medium with mouse IL-3 or with canine IL-31 (cIL-31)

RPMI 1640 435 ml (ThermoFisher, 12633-020)

FBS 50 mL (SAFC cat #12003c-500 mL)

2-Mercaptoethanol (50 mM) 0.5 mL (Gibco 31350-010)

100X Pen Strep 5 mL (Gibco 15140-122 Lot1734040)

200 mM L-Glu 10 ml (Gibco 25030-081 Lot1677185)

500 ng/mL Geneticin G418 (from Gibco or Sigma)

ng/mL mIL-3 or 100 ng/mL cIL-31

Starvation medium: the growth medium without mIL-3 and cIL-31 p-STAT3 (Tyr705) Assay Kit: PerkinElmer, ALSU-PST3-A-HV

Procedure

Cell culture

1. Thaw a vial of the Ba/f3-OI cells, and grow the cells in the growth medium with mIL-3 in 37° C. CO2 shaker with 125 rpm.
2. Passage the cells 2-3 passages to have the cells with ≥90% viability before set a cell-based assay.
3. To setup assay, harvest and resuspend the cells in the starvation medium to $1 \times 10^7$ viable cells/mL.
4. Dispense cells into 96 well plate, 50 μL/well (about $5 \times 10^5$ cells/well).
5. Three-fold dilute cIL-31 in starvation medium in a dilution plate, and then transfer 50 μL of each of the serial diluted cIL-31 aliquots into the cell plate.
6. Incubate the cell plate for 15-30 min in 37° C. $CO_2$ shaker with 125 rpm for 1-2 hrs. AlphaLISA assay as per manufacturer's instruction:
7. Spin down the cells, aspirate the supernatant, and add 1× lysis buffer of 50-100 μL/well. Incubate at RT for 10 min with 1000 rpm shaking.
8. Remove 30 μL of the cell lysate into a ½ area plate or freeze and store at −80° C. for future test.
9. SureFire Assay: add 15 μL/well acceptor mix to the cell lysate. Seal and agitate plate for 2 min at 1000 rpm and then incubate for 1-2 hours at RT.
10. Add 15 μL/well donor mix to the cell lysate. Seal and agitate for 2 min at 1000 rpm, and then incubate for 1-2 hours at RT (the plate can be stored at 4° C. overnight. Incubate at room temp for 1 hr before reading the plate next day)
11. Read the plate on Alpha plate reader at 520-620 nm.

Figure 4:
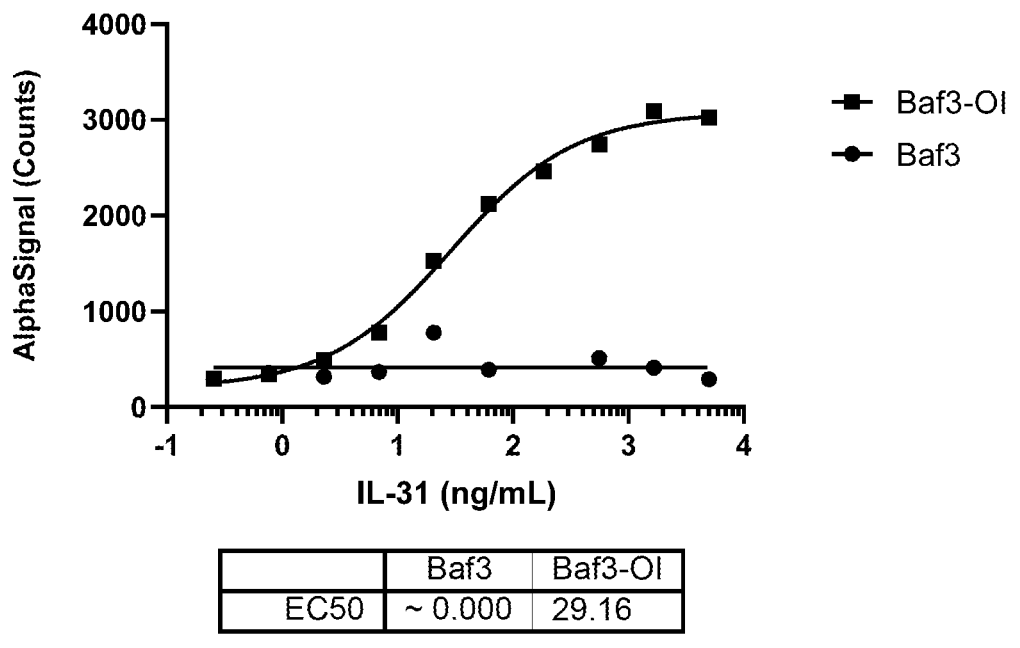
FIG. 4. Ba/f3-OI cells expressing the IL-31 receptor complex were tested for IL-31-induced STAT-3 phosphorylation. The results indicate that STAT-3 phosphorylation was induced by IL-31 in the Ba/f3-OI cells (⊙) in a dose-dependent manner, implying that: (i) the canine IL-31 receptor complex is successfully expressed on cell surface; (ii) that the binding of canine IL-31 to the IL-31 receptor can stimulate the endogenous STAT3 phosphorylation; and (iii) then initiate its downstream signaling pathway. Ba/f3 cells (•) were used as the control.

Results:

As shown in FIG. 4, canine IL-31 stimulates activation of STAT-3 in Ba/f3-OI cells in a dose dependent manner.

Example 8

Biological Activity of Anti-Canine IL-31RA Antibodies

The ability of the anti-canine IL-31RA mAbs to inhibit the activation of STAT-3 in Ba/f3-OI cells is assessed as follows:

1. Thaw a vial of the Ba/f3-OI cells, and grow the Ba/f3-OI cells in the growth medium with mIL-3 in 37° C. CO2 shaker with 125 rpm.
2. Passage the cells 2-3 passages to have the cells with >90% viability before set a cell-based assay.
3. To setup assay, harvest and resuspend the cells in the starvation medium to 1×10 7 viable cells/mL.
4. Dispense cells into 96 well plate, 50 μL/well (about 5×10 5 cells/well).
5. Three-fold dilute the antibody in starvation medium in a row on a 96 well plate, starting concentration at 200 μg/mL. Then add 5-10 μL cIL-31 in each well to get final concentration of 100 ng/mL.
6. Transfer 50 μL of the diluted antibody and cIL-31 mix into each well of the cell plate, gently mix.
7. Incubate the cell plate in 37° C. $CO_2$ shaker with 125 rpm for 1-2 hrs.

AlphaLISA assay as per manufacturer's instruction: (refer to Example 7)

Figure 5:
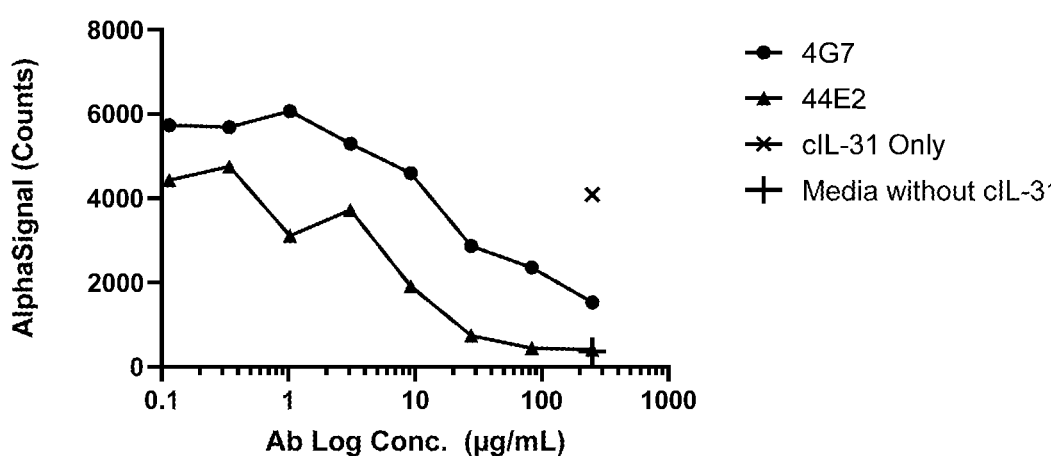
FIG. 5. Inhibition of IL-31-mediated STAT-3 phosphorylation in Ba/f3-OI cells. The results show the inhibition of IL-31-mediated STAT-3 phosphorylation by the antibodies 4G7(•) and 44E2(▲). The media with (✻) or without cIL-31 (+) were used as controls.

Results:

As exemplified in FIG. 5, both antibody 4G7 and 44E2 inhibit the ability of canine IL-31 to stimulate activation of STAT-3 in Ba/f3-OI cells.

Example 9

Mapping of Canine IL-31 Receptor alpha Epitopes using Mass Spectroscopy

A method based on chemical crosslinking and mass spectrometry detection was employed to identify epitopes recognized by anti-canine IL-31 receptor alpha mAbs [Co-valX Instrument Incorporated, located at 999 Broadway, Suite 305, Saugus, MA 01906-4510]. The application of this technology to epitope mapping of canine IL-31 receptor alpha chain resulted in identification of epitopes recognized by the mAbs listed in Table 6. The results from the epitope mapping of canine IL-31 receptor alpha with three antibodies disclosed herein indicates that the mAbs recognize specific peptide epitopes that are present within the extracellular domain of canine IL-31 receptor alpha (see, Table 6 below).

Notably, the epitopes identified for each of the three monoclonal antibodies (mAbs) tested were markedly different. As depicted in Table 6 below, the data indicates the 28F12 antibody binds to a single epitope comprising the amino acid sequence of SEQ ID NO: 101, where the antibody binds with arginine (R) residues at positions 215 and 225, and a lysine (K) residue at position 233 of the amino acid sequence SEQ ID NO: 2. The data further indicates the 44E2 antibody binds to two different epitopes: the first comprising the amino acid sequence of SEQ ID NO: 102, where the antibody binds with a threonine (T) residue at position 408 of the amino acid sequence SEQ ID NO: 2 and a second epitope comprising the amino acid sequence of SEQ ID NO: 103, which has two separate parts, one of which the antibody binds with serine (S) residues at positions 464 and 472, and a tyrosine (Y) residue at position 471 of the amino acid sequence SEQ ID NO: 2 and the other part, where the antibody binds with a threonine (T) residue at position 487 of the amino acid sequence SEQ ID NO: 2. The data further indicates the antibody binds to two different epitopes the first comprising the amino acid sequence of SEQ ID NO: 104, where the antibody binds with tyrosine (Y) residues at positions 31, 34, and 42, and a threonine (T) residue at position 39 of the amino acid sequence SEQ ID NO: 2 and a second epitope comprising the amino acid sequence of SEQ ID NO: 105, where the antibody binds with a lysine (K) residue at position 89, a serine (S) residue at position 90, a threonine (T) residue at position 93, and a tyrosine (Y) residue at position 94 of the amino acid sequence SEQ ID NO: 2.

Sequence Tables

TABLE 1

CANINE IL-31RA EXTRACELLULAR DOMAIN -HIS TAG

|  | SEQ ID NO: | Nucleic Acid | Amino Acid |
|---|---|---|---|
| canine IL-31RA ECD-10His | 1 | X |  |
| canine IL-31RA ECD-10His | 2 |  | X |

TABLE 2

CDRs of Non-BLOCKING ANTIBODIES

|  | Amino Acid Sequence | SEQ ID NO: | Amino Acid Sequence | SEQ ID NO: |
|---|---|---|---|---|
|  | 20B8 |  | 38A6 |  |
| HCDR1 | NYWMT | 3 | NYWMT | 3 |
| HCDR2 | SITNTGGST YYPDSVKG | 4 | SITNTGGST YYPDSVKG | 4 |
| HCDR3 | GPTTVVGGWFAY | 5 | GPTTVVGGWFAY | 5 |
| LCDR1 | KASQNVGSNVD | 6 | KASQNVGSNVD | 6 |
| LCDR2 | RPSNRYT | 7 | RASSRST | 9 |
| LCDR3 | MQSNSYPPT | 8 | MQSNSYPPT | 8 |
|  | 7D7 |  | 48B1 |  |
| HCDR1 | NYWMT | 3 | NYWMT | 3 |
| HCDR2 | SITNTGGS TFYPDSVKG | 10 | SITNTGGS TYYPDSVKG | 4 |
| HCDR3 | GPDYGGHLNWFAY | 11 | GPDYGGHLNWFVY | 46 |
| LCDR1 | KASQNVGSNVD | 6 | KASQNVGSNVD | 6 |
| LCDR2 | KASNRYT | 12 | KASNRYT | 12 |
| LCDR3 | MQSNSYPPT | 8 | MQSNSYPPT | 8 |
|  | 22B4 |  |  |  |
| HCDR1 | KYWMT | 47 |  |  |
| HCDR2 | SITNTGGSS YYSDSVKG | 48 |  |  |
| HCDR3 | GPDYGGHLNWFAY | 11 |  |  |
| LCDR1 | KASQNVGSNVD | 6 |  |  |
| LCDR2 | KASNRYT | 12 |  |  |
| LCDR3 | MQSNSYPPT | 8 |  |  |

TABLE 3

CDRs of BLOCKING ANTIBODIES

|  | Amino Acid Sequence | SEQ ID NO: | Amino Acid Sequence | SEQ ID NO: |
|---|---|---|---|---|
|  | 44E2 |  | 4G7 |  |
| HCDR1 | SNGVS | 13 | STEMH | 19 |
| HCDR2 | AISSGGSTY YNSVLKS | 14 | RIDPVNGNT IYSEKFKS | 20 |
| HCDR3 | RLSGYNYVPFAY | 15 | FNYAGHSGDY | 21 |
| LCDR1 | KASQNIYKHLA | 16 | RASQDVGIYVN | 22 |

TABLE 3-continued

CDRs of BLOCKING ANTIBODIES

| Amino Acid Sequence | SEQ ID NO: | Amino Acid Sequence | SEQ ID NO: |
|---|---|---|---|
| LCDR2 NANSLQT | 17 | RATNLAD | 23 |
| LCDR3 QQYYSGDT | 18 | LQYDEYPYT | 24 |
| 28F12 | | | |
| HCDR1 DYYMA | 25 | | |
| HCDR2 TISYDGSSTYYRDSVRG | 26 | | |
| HCDR3 GPLTDWAPNWFAY | 27 | | |
| LCDR1 QTSEDIYSGLA | 28 | | |
| LCDR2 GASRLED | 29 | | |
| LCDR3 QQGLKYPNT | 30 | | |
| 49D3 | | 10A12 | |
| HCDR1 NYYMA | 31 | NYYMA | 31 |
| HCDR2 SISTGGGNT YYRDSVKG | 32 | SISTGGGNT YYRDSVKG | 32 |
| HCDR3 HGTLYFDY | 33 | HGTLYFDY | 33 |
| LCDR1 ERSSGDIGDSYVS | 34 | ERSSGDIGDSYVS | 34 |
| LCDR2 ADDQRPS | 35 | VDDQRPS | 37 |
| LCDR3 QSYDSNIDGPV | 36 | QSYDSNIDGPV | 36 |
| 47F3 | | 51G4 | |
| HCDR1 NYYMA | 31 | NYYMA | 31 |
| HCDR2 SISTGGGNT YYRDSVKG | 32 | SISTGGGNT YYRDSVKG | 32 |
| HCDR3 HGTLYFDY | 33 | HGTIAAMDY | 39 |
| LCDR1 ERSSGDIGN TYVS | 38 | ERNNGDIGD SYVS | 40 |
| LCDR2 ADDQRPS | 35 | ADDQRPS | 35 |
| LCDR3 QSYDSNIDGPV | 36 | QSYDSNIDGPV | 36 |
| 53B3 | | 27A10 | |
| HCDR1 NYYMA | 31 | NYYMA | 31 |
| HCDR2 SISTGGGNT FYRDSVKG | 41 | SISTGGGNT YYRDSVKG | 32 |
| HCDR3 HGTIAAMDY | 39 | HTMGYFDY | 43 |
| LCDR1 ERTSGDIGD NYVS | 42 | ERSSGDIGD NYVS | 44 |
| LCDR2 ADDQRPS | 35 | ADDQRPS | 35 |
| LCDR3 QSYDSNIDGPV | 36 | QSYDGKIEIPV | 45 |

TABLE 4

RAT ANTI-CANINE IL-31RA VARIABLE REGIONS

| SEQ ID NO: | Heavy Chain | SEQ ID NO: | Light Chain |
|---|---|---|---|
| 49 | 49D3VH | 50 | 49D3VL |
| 51 | 10A12VH | 52 | 10A12VL |
| 53 | 47F3VH | 54 | 47F3VL |
| 55 | 51G4VH | 56 | 51G4VL |
| 57 | 53B3VH | 58 | 53B3VL |
| 59 | 27A10VH | 60 | 27A10VL |
| 61 | 44E2VH | 62 | 44E2VK |
| 63 | 4G7VH | 64 | 4G7VK |
| 65 | 28F12VH | 66 | 28F12VK |
| 67 | 38A6VH | 68 | 38A6VK |
| 69 | 20B8VH | 70 | 20B8VK |
| 71 | 7D7VH | 72 | 7D7VK |
| 73 | 22B4VH | 74 | 22B4VK |
| 75 | 48B1VH | 76 | 48B1VK |

TABLE 5

AMINO ACID SEQUENCES OF CANINIZED ANTIBODIES TO CANINE IL-31RA

| SEQ ID NO: | IL-31 Receptor alpha | Heavy Chain | Light Chain |
|---|---|---|---|
| 83 | c10A12VL5-cCL | | ✓ |
| 84 | c10A12VH1-cIgGBm | ✓ | |
| 85 | c10A12VH2-cIgGBm | ✓ | |
| 86 | c10A12VL4-cCL | | ✓ |
| 87 | c10A12VL6-cCL | | ✓ |
| 88 | c28F12VH1-cIgGBm | ✓ | |
| 89 | c28F12VH2-cIgGBm | ✓ | |
| 90 | c28F12VK1-cCK | | ✓ |
| 91 | c28F12VK2-cCK | | ✓ |
| 92 | c28F12VK3-cCK | | ✓ |
| 93 | c28F12VK4-cCK | | ✓ |
| 94 | c44E2VH1-cIgGBm | ✓ | |
| 95 | c44E2VH4-cIgGBm | ✓ | |
| 96 | c44E2VH5-cIgGBm | ✓ | |
| 97 | c44E2VK1-cCK | | ✓ |
| 98 | c44E2VK2-cCK | | ✓ |
| 99 | c44E2VK4-CcK | | ✓ |
| 100 | c44E2VH2-cIgGBm | ✓ | |

TABLE 6

Epitope Sequences

| Antibody | SEQ ID NO: | Amino Acid Sequences of Epitopes of cIL-31RA |
|---|---|---|
| 28F12 | 101 | GLDLWRVLKPAMVDGR RPVQLMWKKATGAPV |
| 44E2 | 102 | GIPSAGPVTQADSIG VKTVTITWKEI |
| 44E2 | 103 | SKTVNSNILQYRLES LTRRTSYSLQVMAST NAGGINGTKINEKTL SIS |
| 10A12 | 104 | SYTWYKVKRTYSYGY KSDICS |
| 10A12 | 105 | EAQNADGIMKSDITY WNLDAIMKIEPPEIF SVKSVLGIKRMLQIK WIRPVL |

We claim:

1. An isolated mammalian antibody or antigen binding fragment thereof that binds canine interleukin-31 receptor alpha (canine IL-31RA), wherein said antibody comprises a set of six complementary determining regions (CDRs), three of which are heavy chain CDRs: CDR heavy 1 (HCDR1), CDR heavy 2 (HCDR2) and CDR heavy 3 (HCDR3) and three of which are light chain CDRs: CDR light 1 (LCDR1), CDR light 2 (LCDR2), and CDR light 3 (LCDR3); and wherein the set of six CDRs are selected from the group of sets consisting of (i), (ii), and (iii); wherein for set (i):

HCDR1 comprises the amino acid sequence of SEQ ID NO: 13;

HCDR2 comprises the amino acid sequence of SEQ ID NO: 14;

HCDR3 comprises the amino acid sequence of SEQ ID NO: 15;

LCDR1 comprises the amino acid sequence of SEQ ID NO: 16;

LDR2 comprises the amino acid sequence of SEQ ID NO: 17; and

LCDR3 comprises the amino acid sequence of SEQ ID NO: 18;

wherein for set (ii):

HCDR1 comprises the amino acid sequence of SEQ ID NO: 19;

HCDR2 comprises the amino acid sequence of SEQ ID NO: 20;

HCDR3 comprises the amino acid sequence of SEQ ID NO: 21;

LCDR1 comprises the amino acid sequence of SEQ ID NO: 22;

LDR2 comprises the amino acid sequence of SEQ ID NO: 23; and

LCDR3 comprises the amino acid sequence of SEQ ID NO: 24; and wherein for set (iii)

HCDR1 comprises the amino acid sequence of SEQ ID NO: 25;

HCDR2 comprises the amino acid sequence of SEQ ID NO: 26;

HCDR3 comprises the amino acid sequence of SEQ ID NO: 27;

LCDR1 comprises the amino acid sequence of SEQ ID NO: 28;

LDR2 comprises the amino acid sequence of SEQ ID NO: 29; and

LCDR3 comprises the amino acid sequence of SEQ ID NO: 30.

2. The isolated mammalian antibody or antigen binding fragment thereof of claim 1, wherein HCDR1 comprises the amino acid sequence of SEQ ID NO: 13;

wherein HCDR2 comprises the amino acid sequence of SEQ ID NO: 14;

wherein HCDR3 comprises the amino acid sequence of SEQ ID NO: 15;

wherein LCDR1 comprises the amino acid sequence of SEQ ID NO: 16;

wherein LDR2 comprises the amino acid sequence of SEQ ID NO: 17; and wherein LCDR3 comprises the amino acid sequence of SEQ ID NO: 18.

3. The isolated mammalian antibody or antigen binding fragment thereof of claim 2, that when bound to canine IL-31RA the antibody binds to an epitope comprised by the amino acid sequence selected from the group consisting of SEQ ID NO: 102, SEQID NO: 103, and both SEQ ID NO: 102 and SEQID NO: 103.

4. The isolated mammalian antibody or antigen binding fragment thereof of claim 1, wherein HCDR1 comprises the amino acid sequence of SEQ ID NO: 19;

wherein HCDR2 comprises the amino acid sequence of SEQ ID NO: 20;

wherein HCDR3 comprises the amino acid sequence of SEQ ID NO: 21;

wherein LCDR1 comprises the amino acid sequence of SEQ ID NO: 22;

wherein LDR2 comprises the amino acid sequence of SEQ ID NO: 23; and wherein LCDR3 comprises the amino acid sequence of SEQ ID NO: 24.

5. The isolated mammalian antibody or antigen binding fragment thereof of claim 1, wherein HCDR1 comprises the amino acid sequence of SEQ ID NO: 25;

wherein HCDR2 comprises the amino acid sequence of SEQ ID NO: 26;

wherein HCDR3 comprises the amino acid sequence of SEQ ID NO: 27;

wherein LCDR1 comprises the amino acid sequence of SEQ ID NO: 28;

wherein LDR2 comprises the amino acid sequence of SEQ ID NO: 29; and wherein LCDR3 comprises the amino acid sequence of SEQ ID NO: 30.

6. The isolated mammalian antibody or antigen binding fragment thereof of claim 5, that when bound to canine IL-31RA the antibody binds to an epitope comprised by the amino acid sequence of SEQ ID NO: 101.

7. The isolated mammalian antibody or antigen binding fragment thereof of claim 1, wherein the antibody and antigen binding fragment thereof bind canine IL-31RA and block the binding of canine IL-31RA to canine interleukin-31.

8. The isolated mammalian antibody or antigen binding fragment thereof of claim 7, that is a caninized antibody or a caninized antigen binding fragment thereof.

9. The caninized antibody or antigen binding fragment thereof of claim 8, that comprises a hinge region that comprises the amino acid sequence selected from the group consisting of SEQ ID NO: 79, SEQ ID NO: 80, SEQ ID NO: 81, and SEQ ID NO: 82.

10. The caninized antibody or antigen binding fragment thereof of claim 8, that comprises a heavy chain comprising a modified canine IgG-B (IgG-Bm) comprising the amino acid sequence of SEQ ID NO: 78.

11. The caninized antibody or antigen binding fragment thereof of claim 8, wherein the caninized IL-31RA antibody comprises a light chain comprising the amino acid sequence selected from the group consisting of SEQ ID NO: 90, SEQ ID NO: 91, SEQ ID NO: 92, and SEQ ID NO: 93; and a heavy chain comprising the amino acid sequence selected from the group consisting of SEQ ID NO: 88 and SEQ ID NO: 89.

12. The caninized antibody or antigen binding fragment thereof of claim 11, wherein the caninized IL-31RA antibody comprises:

a light chain comprising the amino acid sequence of SEQ ID NO: 92 and a heavy chain comprising the amino acid sequence of SEQ ID NO: 88; or a light chain comprising the amino acid sequence of SEQ ID NO: 93 and a heavy chain comprising the amino acid sequence of SEQ ID NO: 88; or a light chain comprising the amino acid sequence of SEQ ID NO: 92 and a heavy chain comprising the amino acid sequence of SEQ ID NO: 89; or a light chain comprising the amino acid sequence of SEQ ID NO: 93 and a heavy chain comprising the amino acid sequence of SEQ ID NO: 89.

13. The caninized antibody or antigen binding fragment thereof of claim 8, wherein the caninized IL-31RA antibody comprises a light chain comprising the amino acid sequence selected from the group consisting of SEQ ID NO: 97, SEQ ID NO: 98, SEQ ID NO: 99; and SEQ ID NO: 100; and a heavy chain comprising the amino acid sequence selected from the group consisting of SEQ ID NO: 95 and SEQ ID NO: 96.

14. The caninized antibody or antigen binding fragment thereof of claim 13, wherein the caninized IL-31RA antibody comprises:

a light chain comprising the amino acid sequence of SEQ ID NO: 97 and a heavy chain comprising the amino acid sequence of SEQ ID NO: 95; or a light chain comprising the amino acid sequence of SEQ ID NO: 98 and a heavy chain comprising the amino acid sequence of SEQ ID NO: 95; or a light chain comprising the amino acid sequence of SEQ ID NO: 99 and a heavy chain comprising the amino acid sequence of SEQ ID NO: 95; or a light chain comprising the amino acid sequence of SEQ ID NO: 97 and a heavy chain comprising the amino acid sequence of SEQ ID NO: 96; or a light chain comprising the amino acid sequence of SEQ ID NO: 98 and a heavy chain comprising the amino acid sequence of SEQ ID NO: 96; or a light chain comprising the amino acid sequence of SEQ ID NO: 99 and a heavy chain comprising the amino acid sequence of SEQ ID NO: 96 or a light chain comprising the amino acid sequence of SEQ ID NO: 97 and a heavy chain comprising the amino acid sequence of SEQ ID NO: 100; or a light chain comprising the amino acid sequence of SEQ ID NO: 98 and a heavy chain comprising the amino acid sequence of SEQ ID NO: 100; or a light chain comprising the amino acid sequence of SEQ ID NO: 99 and a heavy chain comprising the amino acid sequence of SEQ ID NO: 100.

15. An isolated nucleic acid that encodes a chain of the caninized antibody of claim 8, selected from the group consisting of a heavy chain of the caninized antibody or antigen binding fragment thereof, a light chain of the caninized antibody or antigen binding fragment thereof, or both the heavy chain of the caninized antibody or antigen binding fragment thereof and the light chain of the caninized antibody or antigen binding fragment thereof.

16. An expression vector comprising the isolated nucleic acid of claim 15.

17. A host cell comprising the expression vector of Claim 16.

18. A pharmaceutical composition comprising the caninized antibody or antigen binding fragment thereof of claim 8, and a pharmaceutically acceptable carrier or diluent.

19. A method of aiding in the blocking the pruritus associated with atopic dermatitis, comprising administering to a subject in need thereof a therapeutically effective amount of the pharmaceutical composition of claim 18.

\* \* \* \* \*